US012753433B2

(12) United States Patent
Ricoult et al.

(10) Patent No.: US 12,753,433 B2
(45) Date of Patent: Oct. 6, 2026

(54) METHODS AND SYSTEMS FOR ENCAPSULATING LYOPHILISED MICROSPHERES

(71) Applicant: ILLUMINA, INC., San Diego, CA (US)

(72) Inventors: Sébastien Ricoult, Sawston (GB); Matthias Plitzko, Müllheim (DE); Bernhard Luy, Müllheim (DE)

(73) Assignee: Illumina, Inc., San Diego, CA (US)

( * ) Notice: Subject to any disclaimer, the term of this patent is extended or adjusted under 35 U.S.C. 154(b) by 624 days.

(21) Appl. No.: 18/307,376

(22) Filed: Apr. 26, 2023

(65) Prior Publication Data

US 2023/0348967 A1 Nov. 2, 2023

Related U.S. Application Data

(60) Provisional application No. 63/336,433, filed on Apr. 29, 2022.

(51) Int. Cl.
*C12Q 1/68* (2018.01)
*B01J 13/22* (2006.01)
(Continued)

(52) U.S. Cl.
CPC ............ *C12Q 1/6869* (2013.01); *B01J 13/22* (2013.01); *B05C 19/02* (2013.01)

(58) Field of Classification Search
CPC ......... C12Q 1/6869; B01J 13/22; B05C 19/02
See application file for complete search history.

(56) References Cited

U.S. PATENT DOCUMENTS 5,200,236 A 4/1993 Lang et al.
5,550,044 A 8/1996 Kosak et al.
(Continued)

FOREIGN PATENT DOCUMENTS

WO 2022072193 A1 4/2022

*Primary Examiner* — Jezia Riley
(74) *Attorney, Agent, or Firm* — Heslin Rothenberg Farley & Mesiti P.C.

(57) ABSTRACT

The present disclosure relates to a method, including providing one or more lyophilised microspheres in a mixing vessel at a first temperature and generating a fluidized bed of the one or more lyophilised microspheres in the mixing vessel, under conditions effective to encapsulate the one or more lyophilised microspheres with a coating formulation. In an example, the fluidized bed has a fluidization rate of between about 1 cubic meters per hour ($m^3/h$) and about 30 $m^3/h$. In another example, the fluidized bed has an environmental humidity of between about 10% and about 20%. In still another example, the coating formulation is applied at a spray rate of between about 1.5 grams per minute (g/min) and about 10 g/min. In yet another example, the coating formulation is applied at an atomizing rate of between about 0.5 bar and about 1.5 bar. In a further example, the fluidized bed is in a Wurster configuration, a top spray configuration, or a combination thereof. The present disclosure also relates to a system, including one or more lyophilised microspheres, a mixing vessel configured for holding the one or more lyophilised microspheres, a mixer for generating a fluidized bed of the one or more lyophilised microspheres in the mixing vessel at a location, and at least one spray nozzle configured to introduce a shell formulation into the mixing vessel at the location.

12 Claims, 48 Drawing Sheets

(51) Int. Cl.
*B05C 19/02* (2006.01)
*C12Q 1/6869* (2018.01)

(56) References Cited

U.S. PATENT DOCUMENTS

| | | | |
|---|---|---|---|
| 9,918,942 | B2 | 3/2018 | Freers et al. |
| 2019/0142753 | A1 | 5/2019 | Sun et al. |

*Poor Coating with Bottom Spray Process*

Rehydration test

Coated sugar spheres float, uncoated starting material immediately sinks

Cross section of coated particles pH 4 pH 10

Volume titration in water

*No coating*

*1% Mg Stearate (insoluble)*

*0.6% Gly Stearate (not anti-tacking)*

*3.5% PEG40 Stearate*

*7.9% PEG100 Stearate*

*Anti-foaming agents to be tested in sell to mitigate*

METHODS AND SYSTEMS FOR ENCAPSULATING LYOPHILISED MICROSPHERES

CROSS-REFERENCE TO RELATED APPLICATIONS

This application claims benefit of U.S. Provisional Patent Application Ser. No. 63/336,433, filed Apr. 29, 2022, which is hereby incorporated by reference in its entirety.

FIELD

The present disclosure relates generally methods and systems for encapsulating lyophilised microspheres.

BACKGROUND

Many current sequencing platforms use "sequencing by synthesis" ("SBS") technology and fluorescence based methods for detection. Alternative sequencing methods and improved sample preparation processes that allow for more cost effective, rapid, and convenient sequencing and nucleic acid detection are desirable as complements to SBS.

Current protocols for SBS technology routinely employ a sample preparation process that converts DNA or RNA into a library of fragmented, sequenceable templates. Sample preparation methods often involve multiple steps, material transfers, and expensive instruments to effect fragmentation, and, therefore, are often difficult, tedious, expensive, and inefficient.

Libraries including polynucleotides are generally prepared in any suitable manner to attach oligonucleotide adapters to target polynucleotides. Sequencing may result in determination of the sequence of the whole, or a part of the target polynucleotides. The number of steps involved to transform nucleic acids into adapter-modified templates in solution ready for cluster formation and sequencing can be reduced, or in some instances even minimized, by the use of transposase mediated fragmentation and tagging. This process, referred to as "tagmentation," involves the modification of nucleic acids by a transposome complex including transposase enzyme complexed with adapters including transposon end sequence, as described in, for example, WO 2016/130704. Methods for immobilizing and amplifying prior to sequencing are described in, for instance, U.S. Pat. No. 8,053,192, WO 2016/130704, U.S. Pat. Nos. 8,895,249, and 9,309,502. A library of templates may be used to prepare clustered arrays of nucleic acid colonies, as described in U.S. Pat. Publ. No. 2005/0100900, U.S. Pat. No. 7,115,400, WO 00/18957, and WO 98/44151, by solid-phase amplification and more particularly solid phase isothermal amplification.

Sequencing can be carried out using any suitable sequencing technique, and methods for determining the sequence of immobilized and amplified adapter-target-adapter molecules, including strand re-synthesis, are known in the art and are described in, for instance, U.S. Pat. No. 8,053,192, WO2016/130704, U.S. Pat. Nos. 8,895,249, and 9,309,502. SBS techniques generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. Exemplary SBS systems and methods are described in U.S. Pat. Publ. Nos. 2007/0166705, 2006/0188901, 2006/0240439, 2006/0281109, 2012/0270305, and 2013/0260372, U.S. Pat. No. 7,057,026, WO 05/065814, U.S. Pat. Publ. No. 2005/0100900, WO 06/064199, and WO 07/010,251, U.S. Pat. Publ. No. 2013/0079232.

The stability of the reagents involved with sample preparation including, for example, PCR, varies depending on a variety of factors. Historically, reagents have been wet thereby requiring freezing for ship and storage. Moving to dry reagents allows for ambient transport and storage, but dry reagents are more sensitive than wet reagents to environmental conditions. For example, if reagents are exposed to moisture on manufacture, transport, storage, or during library preparation, quality and efficiency of the resulting library may be affected. Likewise, pH of reagents like SBS buffers varies during sequencing and there is a need for improved stabilization of these buffers to increase SBS performance. Reagents involved with sample preparation may be highly sensitive to changes in humidity, light, and moisture and, as a result, are notoriously difficult to keep stable.

Moreover, lyophilised microspheres which may be used in sample preparation often degrade upon exposure to mechanical stress during transport and storage and may unfavorably shed their outer covering. The resulting powder may be problematic in clogging membranes used in sample preparation and might result in variations in the desired end concentration after rehydration has been achieved. Static charge is also a risk for dispensing and dry compounding microspheres.

Tribocharging is realized by (frictional) contact through particle— particle and/or particle—wall interaction. During contact, charge transfer occurs, and after parting two oppositely charged objects are obtained. Static is realized by the ability of the material (particle or wall) to dissipate electrostatic charge, which is associated with the conductivity of the material.

Lyophilized microspheres are typically manufactured from non-conductive materials (e.g., trehalose). The necessity to handle and store lyophilized microspheres in dry environment is attributed to limited tolerance of the microspheres against ambient humidity. Therefore, in dry environments, static behavior and tribocharging are expected in lyophilized microspheres, which are exhibited through adhesion of the microspheres onto the wall of the container. The risk associated with static is the difficulty to handle microspheres for dry filling into cartridges. Upon dry storage, microspheres tend to adhere onto the wall of cartridges, which lead to cross-contamination between cartridge wells and inaccuracy during rehydration.

Therefore, there is a need for improved sample preparation compositions and associated processes. In particular, there is a need for sequencing reagents with improved stability and associated methods that demonstrate improved efficiency of workflow and tagmented library production and, in turn, increased read enrichment for the resulting libraries. There is also a need for compositions and methods that will improve the read enrichment for the resulting libraries as well as simplify workflows.

The present disclosure is directed to overcoming these and other deficiencies in the art.

SUMMARY

In an aspect, provided is method, including providing one or more lyophilised microspheres in a mixing vessel at a first temperature, where the lyophilised microspheres comprise a nucleic acid sequencing reagent; and generating a fluidized bed of the one or more lyophilised microspheres in the mixing vessel, wherein the fluidized bed has a fluidization rate of between about 1 cubic meters per hour ($m^3/h$) and about 30 $m^3/h$, under conditions effective to encapsulate the one or more lyophilised microspheres with a coating formulation. In an example, the fluidized bed has an environmental humidity of between about 10% and about 20%. In another example, the coating formulation includes a water content of between about 0.1 wt. % and about 5 wt. %. In still another example, the encapsulated lyophilised microspheres include a water content of below about 5 wt. %. In yet another example, the coating formulation is applied by at least one spray nozzle.

In a further example, the at least one spray nozzle has a diameter of between about 0.1 mm and about 1.5 mm. In still a further example, the coating formulation is sprayed on the one or more lyophilised microspheres in the fluidized bed. In yet a further example, the coating formulation is applied at a spray rate of between about 1.5 grams per minute (g/min) and about 10 g/min. In another example, the coating formulation is applied at an atomizing rate of between about 0.5 bar and about 1.5 bar. In still another example, generating the fluidized bed includes elevating the first temperature in the mixing vessel to a second temperature; and supplying air in the mixing vessel under conditions effective to float the one or more lyophilised microspheres in the air. In yet another example, the mixing vessel includes a single open vessel.

In a further example, the mixing vessel includes one or more cylindrical draft tube which is disposed in the mixing vessel. In still a further example, the mixing vessel includes an outer circumference. In yet a further example, the one or more cylindrical draft tube is between about 25 mm and about 500 mm away from the outer circumference of the mixing vessel. In another example, the air is supplied by an air supply unit. In still another example, the fluidized bed is in a Wurster configuration, a top spray configuration, or a combination thereof. In yet another example, the fluidized bed is in a Wurster configuration. In a further example, the fluidized bed is in a top configuration.

In another example, the first temperature includes a temperature at or below about 30° C. In still another example, the second temperature includes a temperature above about 40° C. In yet another example, the mixing vessel has a diameter of between about 25 mm and about 500 mm. In a further example, at least two lyophilised microspheres are provided. In still a further example, the at least one lyophilised microsphere includes one or more reagent. In yet a further example, the one or more reagent includes at least a first reagent and a second reagent. In another example, the first reagent and the second reagent are different. In still another example, the at least one reagent is selected from one or more enzyme, salt, surfactant, buffering agent, enzyme inhibitor, primer, nucleotide, organic osmolite, magnetic bead, molecular probe, crowding agent, small molecule, labelled-nucleotide, a fluorophore, or any combination thereof. In yet another example, the at least one reagent is a polymerase.

In another aspect, provided is a method, including providing one or more lyophilised microspheres in a mixing vessel at a first temperature, where the lyophilised microspheres comprise a nucleic acid sequencing reagent; and generating a fluidized bed of the one or more lyophilised microspheres in the mixing vessel, wherein the fluidized bed has an environmental humidity of between about 10% and about 20%, under conditions effective to encapsulate the one or more lyophilised microspheres with a coating formulation. In another example, the fluidized bed has a fluidization rate of between about 1 cubic meters per hour ($m^3/h$) and about 30 $m^3/h$. In another example, the coating formulation includes a water content of between about 0.1 wt. % and about 5 wt. %. In still another example, the encapsulated lyophilised microspheres include a water content of below about 5 wt. %. In yet another example, the coating formulation is applied by at least one spray nozzle.

In a further example, the at least one spray nozzle has a diameter of between about 0.1 mm and about 1.5 mm. In still a further example, the coating formulation is sprayed on the one or more lyophilised microspheres in the fluidized bed. In yet a further example, the coating formulation is applied at a spray rate of between about 1.5 grams per minute (g/min) and about 10 g/min. In another example, the coating formulation is applied at an atomizing rate of between about 0.5 bar and about 1.5 bar. In still another example, generating the fluidized bed includes elevating the first temperature in the mixing vessel to a second temperature; and supplying air in the mixing vessel under conditions effective to float the one or more lyophilised microspheres in the air. In yet another example, the mixing vessel includes a single open vessel.

In a further example, the mixing vessel includes one or more cylindrical draft tube which is disposed in the mixing vessel. In still a further example, the mixing vessel includes an outer circumference. In yet a further example, the one or more cylindrical draft tube is between about 25 mm and about 500 mm away from the outer circumference of the mixing vessel. In another example, the air is supplied by an air supply unit. In still another example, the fluidized bed is in a Wurster configuration, a top spray configuration, or a combination thereof. In yet another example, the fluidized bed is in a Wurster configuration. In a further example, the fluidized bed is in a top configuration.

In another example, the first temperature includes a temperature at or below about 30° C. In still another example, the second temperature includes a temperature above about 40° C. In yet another example, the mixing vessel has a diameter of between about 25 mm and about 500 mm. In a further example, at least two lyophilised microspheres are provided. In still a further example, the at least one lyophilised microsphere includes one or more reagent. In yet a further example, the one or more reagent includes at least a first reagent and a second reagent. In another example, the first reagent and the second reagent are different. In still another example, the at least one reagent is selected from one or more enzyme, salt, surfactant, buffering agent, enzyme inhibitor, primer, nucleotide, organic osmolite, magnetic bead, molecular probe, crowding agent, small molecule, labelled-nucleotide, a fluorophore, or any combination thereof. In yet another example, the at least one reagent is a polymerase.

In still another aspect, provided is a method, including providing one or more lyophilised microspheres in a mixing vessel at a first temperature, where the lyophilised microspheres comprise a nucleic acid sequencing reagent; and generating a fluidized bed of the one or more lyophilised microspheres in the mixing vessel, wherein the coating formulation is applied at a spray rate of between about 1.5 grams per minute (g/min) and about 10 g/min, under conditions effective to encapsulate the one or more lyophilised microspheres with a coating formulation. In an example, the fluidized bed has a fluidization rate of between about 1 cubic meters per hour ($m^3/h$) and about 30 $m^3/h$. In still another example, the fluidized bed has an environmental humidity of between about 10% and about 20%. In another example, the coating formulation includes a water content of between about 0.1 wt. % and about 5 wt. %. In still another example, the encapsulated lyophilised microspheres include a water content of below about 5 wt. %. In yet another example, the coating formulation is applied by at least one spray nozzle.

In a further example, the at least one spray nozzle has a diameter of between about 0.1 mm and about 1.5 mm. In still a further example, the coating formulation is sprayed on the one or more lyophilised microspheres in the fluidized bed. In another example, the coating formulation is applied at an atomizing rate of between about 0.5 bar and about 1.5 bar. In still another example, generating the fluidized bed includes elevating the first temperature in the mixing vessel to a second temperature; and supplying air in the mixing vessel under conditions effective to float the one or more lyophilised microspheres in the air. In yet another example, the mixing vessel includes a single open vessel.

In a further example, the mixing vessel includes one or more cylindrical draft tube which is disposed in the mixing vessel. In still a further example, the mixing vessel includes an outer circumference. In yet a further example, the one or more cylindrical draft tube is between about 25 mm and about 500 mm away from the outer circumference of the mixing vessel. In another example, the air is supplied by an air supply unit. In still another example, the fluidized bed is in a Wurster configuration, a top spray configuration, or a combination thereof. In yet another example, the fluidized bed is in a Wurster configuration. In a further example, the fluidized bed is in a top configuration.

In another example, the first temperature includes a temperature at or below about 30° C. In still another example, the second temperature includes a temperature above about 40° C. In yet another example, the mixing vessel has a diameter of between about 25 mm and about 500 mm. In a further example, at least two lyophilised microspheres are provided. In still a further example, the at least one lyophilised microsphere includes one or more reagent. In yet a further example, the one or more reagent includes at least a first reagent and a second reagent. In another example, the first reagent and the second reagent are different. In still another example, the at least one reagent is selected from one or more enzyme, salt, surfactant, buffering agent, enzyme inhibitor, primer, nucleotide, organic osmolite, magnetic bead, molecular probe, crowding agent, small molecule, labelled-nucleotide, a fluorophore, or any combination thereof. In yet another example, the at least one reagent is a polymerase.

In yet another aspect, provided is a method, including providing one or more lyophilised microspheres in a mixing vessel at a first temperature, where the lyophilised microspheres comprise a nucleic acid sequencing reagent; and generating a fluidized bed of the one or more lyophilised microspheres in the mixing vessel, wherein the coating formulation is applied at an atomizing rate of between about 0.5 bar and about 1.5 bar, under conditions effective to encapsulate the one or more lyophilised microspheres with a coating formulation. In an example, the fluidized bed has a fluidization rate of between about 1 cubic meters per hour ($m^3/h$) and about 30 $m^3/h$. In an example, the fluidized bed has an environmental humidity of between about 10% and about 20%. In another example, the coating formulation includes a water content of between about 0.1 wt. % and about 5 wt. %. In still another example, the encapsulated lyophilised microspheres include a water content of below about 5 wt. %. In yet another example, the coating formulation is applied by at least one spray nozzle.

In a further example, the at least one spray nozzle has a diameter of between about 0.1 mm and about 1.5 mm. In still a further example, the coating formulation is sprayed on the one or more lyophilised microspheres in the fluidized bed. In yet a further example, the coating formulation is applied at a spray rate of between about 1.5 grams per minute (g/min) and about 10 g/min. In another example, the coating formulation is applied at an atomizing rate of between about 0.5 bar and about 1.5 bar. In still another example, generating the fluidized bed includes elevating the first temperature in the mixing vessel to a second temperature; and supplying air in the mixing vessel under conditions effective to float the one or more lyophilised microspheres in the air. In yet another example, the mixing vessel includes a single open vessel.

In a further example, the mixing vessel includes one or more cylindrical draft tube which is disposed in the mixing vessel. In still a further example, the mixing vessel includes an outer circumference. In yet a further example, the one or more cylindrical draft tube is between about 25 mm and about 500 mm away from the outer circumference of the mixing vessel. In another example, the air is supplied by an air supply unit. In still another example, the fluidized bed is in a Wurster configuration, a top spray configuration, or a combination thereof. In yet another example, the fluidized bed is in a Wurster configuration. In a further example, the fluidized bed is in a top configuration.

In another example, the first temperature includes a temperature at or below about 30° C. In still another example, the second temperature includes a temperature above about 40° C. In yet another example, the mixing vessel has a diameter of between about 25 mm and about 500 mm. In a further example, at least two lyophilised microspheres are provided. In still a further example, the at least one lyophilised microsphere includes one or more reagent. In yet a further example, the one or more reagent includes at least a first reagent and a second reagent. In another example, the first reagent and the second reagent are different. In still another example, the at least one reagent is selected from one or more enzyme, salt, surfactant, buffering agent, enzyme inhibitor, primer, nucleotide, organic osmolite, magnetic bead, molecular probe, crowding agent, small molecule, labelled-nucleotide, a fluorophore, or any combination thereof. In yet another example, the at least one reagent is a polymerase.

In a further aspect, provided is a method, including providing one or more lyophilised microspheres in a mixing vessel at a first temperature, where the lyophilised microspheres comprise a nucleic acid sequencing reagent; and generating a fluidized bed of the one or more lyophilised microspheres in the mixing vessel, wherein the fluidized bed is in a Wurster configuration, a top spray configuration, or a combination thereof, under conditions effective to encapsulate the one or more lyophilised microspheres with a coating formulation. In an example, the fluidized bed has a fluidization rate of between about 1 cubic meters per hour ($m^3/h$) and about 30 $m^3/h$.

In an example, the fluidized bed has an environmental humidity of between about 10% and about 20%. In another example, the coating formulation includes a water content of between about 0.1 wt. % and about 5 wt. %. In still another example, the encapsulated lyophilised microspheres include a water content of below about 5 wt. %. In yet another example, the coating formulation is applied by at least one spray nozzle.

In a further example, the at least one spray nozzle has a diameter of between about 0.1 mm and about 1.5 mm. In still a further example, the coating formulation is sprayed on the one or more lyophilised microspheres in the fluidized bed. In yet a further example, the coating formulation is applied at a spray rate of between about 1.5 grams per minute (g/min) and about 10 g/min. In another example, the coating formulation is applied at an atomizing rate of between about 0.5 bar and about 1.5 bar. In still another example, generating the fluidized bed includes elevating the first temperature in the mixing vessel to a second temperature; and supplying air in the mixing vessel under conditions effective to float the one or more lyophilised microspheres in the air. In yet another example, the mixing vessel includes a single open vessel.

In a further example, the mixing vessel includes one or more cylindrical draft tube which is disposed in the mixing vessel. In still a further example, the mixing vessel includes an outer circumference. In yet a further example, the one or more cylindrical draft tube is between about 25 mm and about 500 mm away from the outer circumference of the mixing vessel. In another example, the air is supplied by an air supply unit. In still another example, the fluidized bed is in a Wurster configuration, a top spray configuration, or a combination thereof. In yet another example, the coating formulation is applied at an atomizing rate of between about 0.5 bar and about 1.5 bar.

In still another example, the fluidized bed is in a Wurster configuration, a top spray configuration, or a combination thereof. In yet another example, the fluidized bed is in a Wurster configuration. In a further example, the fluidized bed is in a top configuration.

In another example, the first temperature includes a temperature at or below about 30° C. In still another example, the second temperature includes a temperature above about 40° C. In yet another example, the mixing vessel has a diameter of between about 25 mm and about 500 mm. In a further example, at least two lyophilised microspheres are provided. In still a further example, the at least one lyophilised microsphere includes one or more reagent. In yet a further example, the one or more reagent includes at least a first reagent and a second reagent. In another example, the first reagent and the second reagent are different. In still another example, the at least one reagent is selected from one or more enzyme, salt, surfactant, buffering agent, enzyme inhibitor, primer, nucleotide, organic osmolite, magnetic bead, molecular probe, crowding agent, small molecule, labelled-nucleotide, a fluorophore, or any combination thereof. In yet another example, the at least one reagent is a polymerase.

In an example, one or more of the fluidized bed has a fluidization rate of between about 1 cubic meters per hour ($m^3$/h) and about 30 $m^3$/h, the fluidized bed has an environmental humidity of between about 10% and about 20%, the coating formulation is applied at a spray rate of between about 1.5 grams per minute (g/min) and about 10 g/min, the coating formulation is applied at an atomizing rate of between about 0.5 bar and about 1.5 bar, and the fluidized bed is in a Wurster configuration, a top spray configuration, or a combination thereof, and any combination of two or more of the foregoing.

In still a further aspect, provided is a system, including one or more lyophilised microspheres, where the lyophilised microspheres comprise a nucleic acid sequencing reagent; a mixing vessel configured for holding the one or more lyophilised microspheres; a mixer for generating a fluidized bed of the one or more lyophilised microspheres in the mixing vessel at a location; and at least one spray nozzle configured to introduce a shell formulation into the mixing vessel at the location.

BRIEF DESCRIPTION OF THE DRAWINGS

FIG. 25A shows images of various encapsulated microspheres prepared in accordance with the methods described herein.

FIG. 25B shows water content measurements for encapsulated microspheres prepared in accordance with the methods described herein. The coating process may increases percent residual moisture.

FIGS. 28A and 28B show mechanical strength of microspheres that are encapsulated using the methods described herein. FIG. 28A shows modulus of strength. FIG. 28B shows max stress.

FIG. 29A shows D50 average versus diameter. FIG. 29B shows average span versus diameter.

Figure 1:
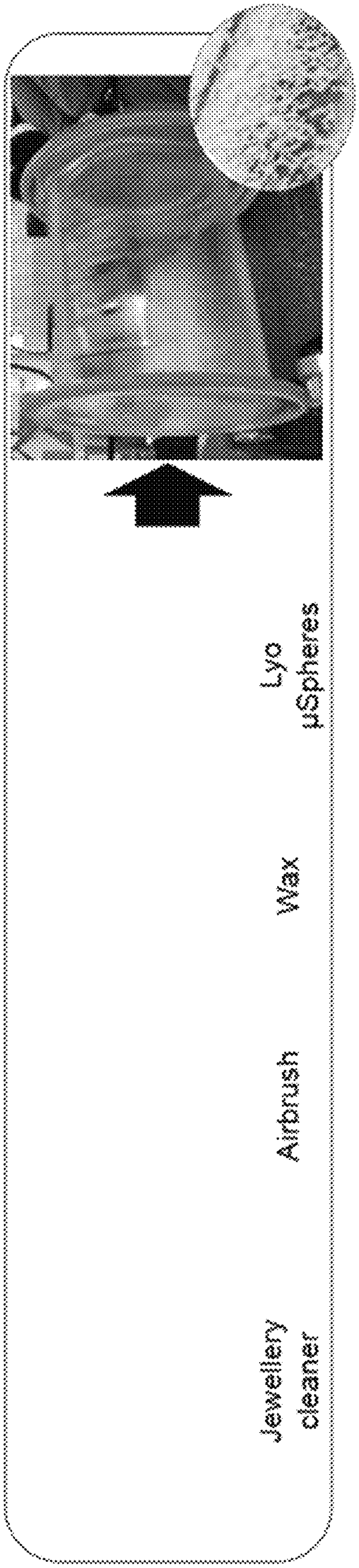
FIG. 1 illustrates one implementation of producing coated microspheres. Microspheres are inside a chamber and wax coating is applied to microspheres using an air brush. The air brush may generate significant air drafts in the chamber which results in some microspheres leaving the chamber. A filtration membrane is added to prevent the microspheres from leaving the chamber. An aerosolizer may be used instead of an air brush to generate less air flow.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits and advantages described herein.

DETAILED DESCRIPTION

In accordance with the present disclosure, methods and systems described herein have many benefits including, for example, increasing stability of microspheres, macroencapsulation to enable multi-run cartridges, and microencapsulation to enable simplified workflows and reduced number of reagent wells.

To increase the stability of sequencing reagents and to simplify workflows, there is great interest and an unmet need to encapsulate lyophilised microspheres. The present disclosure describes methods and systems relating to encapsulating lyophilised microspheres for eventual use in sequential release of lyophilised reagents.

There are numerous benefits to the methods and systems described herein. For example, the methods of encapsulating lyophilised microspheres provide anti-static protection, by neutralizing charge and decreasing tribocharging affinity, thereby decreasing metering and manufacturing handling complexity (e.g., mesoporous silica, ionic liquids, quaternary amines). Static charge has been identified as a significant risk for dispensing and dry compounding microspheres, as it has a significant impact on metering and mixing of dry microsphere powders during manufacturing. Encapsulating microspheres as described in the methods and systems described herein neutralizes the charge of microspheres by, for example, coating the particles with a neutral material with low tribocharging affinity, which greatly improves stability for sequencing.

Likewise, the methods and systems described herein provide oxygen protection through a low oxygen permeability polymer coating (e.g., polyvinyl alcohol and/or oxygen scavenger in coating). Similarly, the methods and systems described herein provide moisture protection through application of an amphiphilic coating (e.g., amino acids and/or PVP co-polymers). The methods and systems described herein further provide protection from mechanical stress, for example, by preventing fragmentation in manufacturing (e.g., by providing a 40% solute content shell). Such a protective coating increases the mechanical robustness of microspheres and their contents during manufacturing and shipping and eliminates shedding of powders from microspheres that may otherwise result in a powder that clogs membranes.

The methods and systems described herein may further provide protection from light exposure, as the reagents are protected from light exposure thereby decreasing manufacturing light constraints. Encapsulating lyophilised microspheres can improve sequencing quality, enable one-pot library prep, and simplify manufacturing.

The methods and systems described herein enable benefits in addition to those described above. For example, using lyophilised materials, and segregated lyophilised materials, means additional co-factors for the enzyme such as magnesium can be added to the microspheres themselves rather than having a separate additional rehydration buffer. This may enable all reagents of different concentrations, types of enzymes, all requiring different amounts of co-factors, salts, pHs, and more, to be rehydrated just with water alone, or even atmospheric water capture. This will lead to knock-on reductions in the amount of plastic used in sequencing processes as well as carbon footprint given the reduced weight of reagents when in concentrated and/or lyophilised form.

The encapsulation methodology described herein can be applied to enable an easy way to tune reagent concentrations. For example, a smaller capsule may contain a smaller quantity of lyophilised reagent as compared to a larger capsule, and multiples of this capsule can be placed in the well in line with the needs of the user. This promotes improved user flexibility in terms of throughput, without the potential errors made with dilution/concentration calculations. A unit-based approach, where X number of capsules=Y number of runs allows this flexibility in a more controlled fashion. Such an approach may also grant flexibility to the user in terms of depth of sequencing. An application that involves deep sequencing, for example, cancer screening, may use many capsules, whereas a superficial screening, for example, MRSA, may use fewer capsules.

The methods and systems described herein achieve an improved level of control over reagent release (e.g., rehydration of a first reagent, followed by delayed rehydration of one or more subsequent reagents after a period of time) as well as mechanical protection, buffer stabilization, charge control, combination of two or more different reagents in a single microsphere, single well, or single pot, and light protection.

It is to be appreciated that certain aspects, modes, implementations, variations, and features of the present disclosure are described below in various levels of detail in order to provide a substantial understanding of the present technology. Unless otherwise noted, all technical and scientific terms used herein generally have the same meaning as commonly understood by one of ordinary skill in the art. The use of the term "including" as well as other forms is not limiting. The use of the term "having" as well as other forms is not limiting. As used in this disclosure, whether in a transitional phrase or in the body of the claim, the terms "comprise(s)" and "comprising" are to be interpreted as having an open-ended meaning. That is, the terms are to be interpreted synonymously with the phrases "having at least" or "including at least."

The terms "substantially", "approximately", "about", "relatively", or other such similar terms that may be used throughout this disclosure, including the claims, are used to describe and account for small fluctuations, such as due to variations in processing, from a reference or parameter. Such small fluctuations include a zero fluctuation from the reference or parameter as well. For example, fluctuations can refer to less than or equal to ±10%, such as less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

It is further appreciated that certain features described herein, which are, for clarity, described in the context of separate implementations, can also be provided in combination in a single implementation. Conversely, various features which are, for brevity, described in the context of a single implementation, can also be provided separately or in any suitable sub-combination.

The terms "connect", "contact", and/or "coupled" include a variety of arrangements and assemblies. These arrangements and techniques include, but are not limited to, (1) the direct joining of one component and another component with no intervening components therebetween (i.e., the components are in direct physical contact); and (2) the joining of one component and another component with one or more components therebetween, provided that the one component being "connected to" or "contacting" or "coupled to" the other component is somehow in operative communication (e.g., electrically, fluidly, physically, optically, etc.) with the other component (optionally with the presence of one or more additional components therebetween). Components that are in direct physical contact with one another may or may not be in electrical contact and/or fluid contact with one another. Moreover, two components that are electrically connected, electrically coupled, optically connected, optically coupled, fluidly connected, or fluidly coupled may or may not be in direct physical contact, and one or more other components may be positioned between those two connected components.

As described herein, the term "array" may include a population of conductive channels or molecules that may attach to one or more solid-phase substrates such that the conductive channels or molecules can be differentiated from one another based on their location. An array as described herein may include different molecules that are each located at a different identifiable location (e.g., at different conductive channels) on a solid-phase substrate. Alternatively, an array may include separate solid-phase substrates each bearing a different molecule, where the different probe molecules can be identified according to the locations of the solid-phase substrates on a surface to which the solid-phase substrates attach or based on the locations of the solid-phase substrates in a liquid such as a fluid stream. Examples of arrays where separate substrates are located on a surface include wells having beads as described in U.S. Pat. No. 6,355,431, U.S. Pat. Publ. No. 2002/0102578, and WO 00/63437, all of which are hereby incorporated by reference in their entirety. Molecules of the array can be nucleic acid primers, nucleic acid probes, nucleic acid templates, or nucleic acid enzymes such as polymerases and exonucleases.

As described herein, the term "attached" may include when two things are joined, fastened, adhered, connected, or bound to one another. A reaction component, like a polymerase, can be attached to a solid phase component, like a conductive channel, by a covalent or a non-covalent bond. As described herein, the phrase "covalently attached" or "covalently bonded" refers to forming one or more chemical bonds that are characterized by the sharing of pairs of electrons between atoms. A non-covalent bond is one that does not involve the sharing of pairs of electrons and may include, for example, hydrogen bonds, ionic bonds, van der Waals forces, hydrophilic interactions, and hydrophobic interactions.

As described herein, the terms "polynucleotide" or "nucleic acids" refer to deoxyribonucleic acid (DNA), ribonucleic acid (RNA), or analogs of either DNA or RNA made from nucleotide analogs. The terms as used herein also encompasses cDNA, that is complementary, or copy DNA produced from an RNA template, for example by the action of reverse transcriptase. In one implementation, the nucleic acid to be analyzed, for example by sequencing through use of the described systems, is immobilized on a substrate (e.g., a substrate within a flow cell or one or more beads upon a substrate such as a flow cell, etc.). The term immobilized as used herein is intended to encompass direct or indirect, covalent, or non-covalent attachment, unless indicated otherwise, either explicitly or by context. The analytes (e.g., nucleic acids) may remain immobilized or attached to the support under conditions in which it is intended to use the support, such as in applications requiring nucleic acid sequencing. In one implementation, the template polynucleotide is one of a plurality of template polynucleotides attached to a substrate. In one implementation, the plurality of template polynucleotides attached to the substrate include a cluster of copies of a library polynucleotide as described herein.

The term "fluidized bed" refers to a physical phenomenon wherein particles, such as lyophilised microspheres or other particles in accordance with aspects of the present disclosure, are subjected to a process whereby they exhibit characteristics of a fluid (i.e., fluidization), such as able to be moved via pumping mechanisms suitable for moving fluids, or flowing freely in response to gravitational forces, etc. In accordance with aspects of the present disclosure, lyophilised microspheres or other particles may be subjected to conditions for inducing a fluidized bed state thereby rendering them able to receive a coating or other layer disposed thereupon, such as by introducing compositions or components intended to be deposited on the lyophilised microspheres or other particles for the purpose of coating them therewith. As disclosed herein, various vessels, containers, and manufactures may be used, in various applicable configurations, for inducing lyophilized microspheres or other particles in accordance with aspects of the present disclosure to adopt a fluidized bed structure and receive a coating or other substance or composition disposed thereon.

Non-limiting examples of fluidized beds include a stationary or particulate fluidized bed, a bubbling or aggregative fluidized bed, a circulating fluidized bed, a vibratory fluidized bed, a transport or flash reactor fluidized bed, an annular fluidized bed, a mechanically fluidized reactor fluidized bed, and a narrow fluidized bed. Likewise, in accordance with aspects of the present disclosure, various manufactures of vessels disposed in various configurations may be adopted for inducing formation of fluidized beds and applying a coating to lyophilized microspheres and other particles. Non-limiting examples include top-spray coating, bottom-spray coating, tangential spray coating. An example includes Wurster coating.

Nucleic acids include naturally occurring nucleic acids or functional analogs thereof. Particularly useful functional analogs are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art such as peptide nucleic acid (PNA) or locked nucleic acid (LNA). Naturally occurring nucleic acids generally have a deoxyribose sugar (e.g. found in deoxyribonucleic acid (DNA)) or a ribose sugar (e.g. found in ribonucleic acid (RNA)).

In RNA, the sugar is a ribose, and in DNA a deoxyribose, i.e., a sugar lacking a hydroxyl group that is present in ribose. The nitrogen containing heterocyclic base can be purine or pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose may be bonded to N-1 of a pyrimidine or N-9 of a purine.

A nucleic acid can contain any of a variety of analogs of these sugar moieties that are known in the art. A nucleic acid can include native or non-native bases. A native deoxyribonucleic acid can have one or more bases selected from the group consisting of adenine, thymine, cytosine, or guanine and a ribonucleic acid can have one or more bases selected from the group consisting of uracil, adenine, cytosine or guanine. Useful non-native bases that can be included in a nucleic acid are known in the art.

The term nucleotide as described herein may include natural nucleotides, analogs thereof, ribonucleotides, deoxyribonucleotides, dideoxyribonucleotides and other molecules known as nucleotides. As described herein, a nucleotide may include a nitrogen containing heterocyclic base, a sugar, and one or more phosphate groups. Nucleotides may be monomeric units of a nucleic acid sequence, for example to identify a subunit present in a DNA or RNA strand. A nucleotide may also include a molecule that is not necessarily present in a polymer, for example, a molecule that is capable of being incorporated into a polynucleotide in a template dependent manner by a polymerase. A nucleotide may include a nucleoside unit having, for example, 0, 1, 2, 3 or more phosphates on the 5' carbon. Tetraphosphate nucleotides, pentaphosphate nucleotides, and hexaphosphate nucleotides may be useful, as may be nucleotides with more than 6 phosphates, such as 7, 8, 9, 10, or more phosphates, on the 5' carbon. Examples of naturally occurring nucleotides include, without limitation, ATP, UTP, CTP, GTP, ADP, UDP, CDP, GDP, AMP, UMP, CMP, GMP, dATP, dTTP, dCTP, dGTP, dADP, dTDP, dCDP, dGDP, dAMP, dTMP, dCMP, and dGMP.

Non-natural nucleotides include nucleotide analogs, such as those that are not present in a natural biological system or not substantially incorporated into polynucleotides by a polymerase in its natural milieu, for example, in a non-recombinant cell that expresses the polymerase. Non-natural nucleotides include those that are incorporated into a polynucleotide strand by a polymerase at a rate that is substantially faster or slower than the rate at which another nucleotide, such as a natural nucleotide that base-pairs with the same Watson-Crick complementary base, is incorporated into the strand by the polymerase. For example, a non-natural nucleotide may be incorporated at a rate that is at least 2 fold different, 5 fold different, 10 fold different, 25 fold different, 50 fold different, 100 fold different, 1000 fold different, 10000 fold different, or more when compared to the incorporation rate of a natural nucleotide. A non-natural nucleotide can be capable of being further extended after being incorporated into a polynucleotide. Examples include, nucleotide analogs having a 3' hydroxyl or nucleotide analogs having a reversible terminator moiety at the 3' position that can be removed to allow further extension of a polynucleotide that has incorporated the nucleotide analog. Examples of reversible terminator moieties are described, for example, in U.S. Pat. Nos. 7,427,673, 7,414,116, and 7,057,026, as well as WO 91/06678 and WO 07/123744, each of which is hereby incorporated by reference in its entirety. It will be understood that in some examples a nucleotide analog having a 3' terminator moiety or lacking a 3' hydroxyl (such as a dideoxynucleotide analog) can be used under conditions where the polynucleotide that has incorporated the nucleotide analog is not further extended. In some examples, nucleotide(s) may not include a reversible terminator moiety, or the nucleotides(s) will not include a non-reversible terminator moiety or the nucleotide(s) will not include any terminator moiety at all.

This disclosure encompasses nucleotides including a fluorescent label (or any other detection tag) that may be used in any method disclosed herein, on its own or incorporated into or associated with a larger molecular structure or conjugate.

The fluorescent label can include compounds selected from any known fluorescent species, for example rhodamines or cyanines. A fluorescent label as disclosed herein may be attached to any position on a nucleotide base, and may optionally include a linker. The function of the linker is generally to aid chemical attachment of the fluorescent label to the nucleotide. In particular implementations Watson-Crick base pairing can still be carried out for the resulting analogue. A linker group may be used to covalently attach a dye to the nucleoside or nucleotide. A linker moiety may be of sufficient length to connect a nucleotide to a compound such that the compound does not significantly interfere with the overall binding and recognition of the nucleotide by a nucleic acid replication enzyme. Thus, the linker can also include a spacer unit. The spacer distances, for example, the nucleotide base from a cleavage site or label.

As used herein, a "nucleoside" is structurally similar to a nucleotide, but is missing the phosphate moieties. An example of a nucleoside analogue is one in which the label is linked to the base and there is no phosphate group attached to the sugar molecule. The term "nucleoside" is used herein in its ordinary sense as understood by those skilled in the art. Examples include, but are not limited to, a ribonucleoside including a ribose moiety and a deoxyribonucleoside including a deoxyribose moiety. A modified pentose moiety is a pentose moiety in which an oxygen atom has been replaced with a carbon and/or a carbon has been replaced with a sulfur or an oxygen atom. A "nucleoside" is a monomer that may have a substituted base and/or sugar moiety.

The term "purine base" is used herein in its ordinary sense as understood by those skilled in the art, and includes its tautomers. Similarly, the term "pyrimidine base" is used herein in its ordinary sense as understood by those skilled in the art, and includes its tautomers. A non-limiting list of optionally substituted purine-bases includes purine, adenine, guanine, hypoxanthine, xanthine, alloxanthine, 7-alkylguanine (e.g. 7-methylguanine), theobromine, caffeine, uric acid and isoguanine. Examples of pyrimidine bases include, but are not limited to, cytosine, thymine, uracil, 5,6-dihydrouracil and 5-alkylcytosine (e.g., 5-methylcytosine).

The term substrate (or solid support), as described herein, may include any inert substrate or matrix to which nucleic acids can be attached, such as for example glass surfaces, plastic surfaces, latex, dextran, polystyrene surfaces, polypropylene surfaces, polyacrylamide gels, gold surfaces, and silicon wafers. For example, a substrate may be a glass surface (e.g., a planar surface of a flow cell channel). In one implementation, a substrate may include an inert substrate or matrix which has been "functionalized," such as by applying a layer or coating of an intermediate material including reactive groups which permit covalent attachment to molecules such as polynucleotides. Supports may include polyacrylamide hydrogel supported on an inert substrate such as glass. Molecules (e.g., polynucleotides) may be directly covalently attached to an intermediate material (e.g., a hydrogel). A support may include a plurality of particles or beads each having a different attached analyte.

As used herein, "derivative" or "analogue" means a synthetic nucleotide or nucleoside derivative having modified base moieties and/or modified sugar moieties. Such derivatives and analogs are discussed in, for example, Bucher, NUCLEOTIDE ANALOGS (John Wiley & Son, 1980) and Uhlmann et al., "Anti sense Oligonucleotides: A New Therapeutic Principle," Chemical Reviews 90:543-584 (1990), both of which are hereby incorporated by reference in their entirety. Nucleotide analogs may also include modified phosphodiester linkages, including phosphorothioate, phosphorodithioate, alkyl-phosphonate, phosphoranilidate and phosphoramidate linkages. "Derivative", "analog", and "modified" as used herein, may be used interchangeably, and are encompassed by the terms "nucleotide" and "nucleoside" as described herein.

As described herein, "encapsulate", "encapsulated", and "encapsulation" include the enclosing of one or more microspheres as described herein. Microencapsulation as described herein refers to the embedding of at least one ingredient, for example, an active agent, into at least one other material, for example, a shell material. Encapsulation in accordance with the present disclosure includes, but is not limited to, bulk encapsulation, macroencapsulation, microencapsulation, nano encapsulation, single molecule, and ionic encapsulation. In accordance with the present disclosure, the methods and systems described herein have many benefits including, for example, increasing stability of microspheres, use of macroencapsulation to enable multi-run cartridges, and use of microencapsulation to enable simplified workflows and reduced number of reagent wells. The methods and systems described herein use encapsulation of particles that would otherwise be responsive to pH changes to stabilize these buffers and increase SBS performance. The methods and systems described herein also use encapsulation to reduce the risk of static charge that otherwise presents difficulty for dispensing and dry compounding microspheres during manufacturing. The methods and systems may further include modifications to pH and humidity to further control stability of one or more encapsulated microspheres and the reagent(s) contained therein.

As used herein, "microsphere" includes spherical particles that include a shell and a core and have a diameter of 0.1 μm to 1,000 μm. For example, a microsphere may have a diameter of about 0.1 μm, 0.5 μm, 1 μm, 10 μm, 20 μm, 30 μm, 40 μm, 50 μm, 60 μm, 70 μm, 80 μm, 90 μm, 100 μm, 150 μm, 200 μm, 300 μm, 400 μm, 500 μm, 600 μm, 700 μm, 800 μm, 900 μm, 1000 μm, or any diameter between about 0.1 μm and about 1,000 μm. In one implementation, the encapsulated microsphere has a diameter between about 100 μm and 1000 μm.

Microspheres are generally comprised of a polymer shell, for example, biodegradable polymers. Microspheres in accordance with the present disclosure include those prepared by conventional techniques, which are known to those skilled in the art. For example, microspheres may be prepared by freezing a liquid into frozen pellets, followed by placing frozen microspheres in a dryer, for example, a rotational dryer.

As described herein, "macrosphere" may include a plurality of microspheres. Macrospheres are generally of a bigger diameter than microspheres, for example, between 0.1 mm and 1,000 mm. Macrospheres described herein may, for example, have a diameter of about 0.1 mm, 1 mm, 2 mm, 3 mm, 4 mm, 5 mm, 6 mm, 7 mm, 8 mm, 9 mm, 10 mm, 50 mm, 100 mm, 200 mm, 300 mm, 400 mm 500 mm, 600 mm, 700 mm, 800 mm, 900 mm, 1,000 mm, or any diameter between about 0.1 mm and about 1,000 mm. In one implementation, macrospheres (e.g., macrocapsules) will have a dimension ranging between about 5 mm×5 mm×9 mm to about 7 cm×7 cm×2 cm.

Macrospheres in accordance with the present disclosure include those prepared by conventional techniques, which are known to those skilled in the art. The methods and systems described herein may produce a single lyophilised microsphere, or may include a plurality of lyophilised microspheres and may thereby form a macrosphere. For example, the composition described herein may include anywhere between 1 and over 1,000,000 lyophilised microspheres. In one implementation, the composition includes 1 lyophilised microsphere, or less than 100 lyophilised microspheres, or less than 500 lyophilised microspheres, or any number of microspheres between about 1 and about 1,000,000. In one implementation, when the shell surrounds more than one lyophilised microsphere, the reagents in the core of the lyophilised microspheres are different.

Various processes and configurations for fluidization may be used in accordance with the methods and systems described herein. In one implementation, fluidization may be generated in a fluidized bed that is in a Wurster configuration, a top spray configuration, or a combination thereof. In a particular implementation, the fluidized bed is in a Wurster configuration. In another implementation, the fluidized bed is in a top configuration. A Wurster configuration as described herein may include a bottom spray through a tube to control the flow. A Top Spray configuration as described herein may include spraying from the top while fluidizing from the bottom. Alternatively configurations for fluidization are also contemplated to be useful in accordance with the methods and systems described herein, including, a bottom spray, which includes spraying from the bottom while fluidizing from the bottom; a tangential spray, which includes spraying from the side while fluidizing from the bottom; and/or a Pan Coater spray configuration, which includes a rotational drum while spraying from the center.

A mixing vessel as described herein includes any vessel or container that is suitable for generating an appropriate fluidized bed to encapsulate and/or coat the lyophilised microspheres described herein. In one implementation, the mixing vessel has a diameter of between about 25 mm and about 250 mm. For example, the mixing vessel may have a diameter of about 25 mm, about 30 mm, about 35 mm, about 40 mm, about 45 mm, about 50 mm, about 55 mm, about 60 mm, about 65 mm, about 70 mm, about 75 mm, about 80 mm, about 85 mm, about 90 mm, about 95 mm, about 100 mm, about 105 mm, about 110 mm, about 115 mm, about 120 mm, about 125 mm, about 130 mm, about 135 mm, about 140 mm, about 145 mm, about 150 mm, about 155 mm, about 160 mm, about 165 mm, about 170 mm, about 175 mm, about 180 mm, about 185 mm, about 190 mm, about 195 mm, about 200 mm, about 205 mm, about 210 mm, about 215 mm, about 220 mm, about 225 mm, about 230 mm, about 235 mm, about 240 mm, about 245 mm, about 250 mm, or any diameter therebetween.

In one implementation, the mixing vessel comprises a single open vessel. Such an implementation may be particularly useful in a top spray configuration. In one implementation, the mixing vessel comprises one or more cylindrical draft tube which is disposed in the mixing vessel. Such an implementation may be particularly useful in a Wurster configuration. In one implementation, the mixing vessel comprises an outer circumference. And, in one further implementation, the one or more cylindrical draft tube is between about 25 mm and about 500 mm away from the outer circumference of the mixing vessel. For example the one or more cylindrical draft tube may be about 25 mm, about 30 mm, about 35 mm, about 40 mm, about 45 mm, about 50 mm, about 55 mm, about 60 mm, about 65 mm, about 70 mm, about 75 mm, about 80 mm, about 85 mm, about 90 mm, about 95 mm, about 100 mm, about 125 mm, about 150 mm, about 175 mm, about 200 mm, about 225 mm, about 250 mm, about 275 mm, about 300 mm, about 325 mm, about 350 mm, about 375 mm, about 400 mm, about 425 mm, about 450 mm, about 475 mm, about 500 mm, or any amount therebetween, away from the outer circumference of the mixing vessel.

In generating the fluidized bed in accordance with the methods and systems described herein, the air is supplied by an air supply unit in one implementation. The air supplied may be supplied from the bottom, middle, or top of the mixing vessel, or placed in any suitable position to effectively carry out the systems and methods described herein. In one implementation, the coating formulation is applied by at least one spray nozzle. The spray nozzle may similarly be placed in any suitable position to effectively carry out the systems and methods described herein. In one implementation, the at least one spray nozzle has a diameter of between about 0.1 mm and about 1.5 mm. For example, the at least one spray nozzle may have a diameter of about 0.1 mm, about 0.2 mm, about 0.3 mm, about 0.4 mm, about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, or any diameter size therebetween.

The first temperature provided in the mixing vessel may, in one implementation, be elevated to a second temperature, and air may be supplied in the mixing vessel under conditions effective to float the one or more lyophilised microspheres in the air. The elevation in temperature may be used to optimize conditions to promote improved encapsulation and/or coating of lyophilised microspheres, as described herein. In one implementation, the first temperature comprises a temperature at or below about 20° C. For example, the first temperature may be about 20° C., about 15° C., about 10° C., about 5° C., about 0° C., about −5° C., about −10° C., about −15° C., about −20° C., about −25° C., about −30° C., or any temperate therebetween. In one implementation, the first temperature may be between about 20° C. and about 10° C., or between about 20° C. and about 5° C., or between 20° C. and about 0° C. In one implementation, the second temperature may be above about 20° C. For example, the temperature may be about 21° C., about 22° C., about 23° C., about 24° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., or any temperature therebetween. In one implementation, the first temperature is lower than the second temperature. Substrate material needs to be heated for solvents in coating solution to evaporate in process. The material generally cannot be fluidized to achieve this as in the absence of spraying coating solution static charges will build up. Spraying may not be initiated without heat for fear of nozzle clogging. The solution discovered herein includes preheating the instrument before adding substrate from a first temperature to a second temperature, then adding substrate rapidly keeping heat and immediately initiating spraying.

The methods and systems described herein may be optimized to establish improved and useful conditions for encapsulating and/or coating the lyophilised microspheres described herein. There are various challenges that need to be addressed when encapsulating and/or coating lyophilised microspheres, including, but not limited to the physical characteristics of the lyophilised microsphere including their charge density, size, hygroscopic nature, and core sensitivity to high temperatures. Accordingly, various parameters and conditions in fluidization where optimized to overcome such challenges. In one implementation, for example, the fluidized bed may have a fluidization rate between 0.1 cubic meters per hour ($m^3$/h) and 50 $m^3$/h, and may in one implementation, may be further optimized to a fluidization rate between 1 $m^3$/h and 30 $m^3$/h. For example, the fluidization rate may be about 0.1 $m^3$/h, about 0.2 $m^3$/h, about 0.3 $m^3$/h, about 0.4 $m^3$/h, about 0.5 $m^3$/h, about 0.6 $m^3$/h, about 0.7 $m^3$/h, about 0.8 $m^3$/h, about 0.9 $m^3$/h, about 1 $m^3$/h, 1.5 $m^3$/h, about 2 $m^3$/h, about 3 $m^3$/h, about 4 $m^3$/h, about 5 $m^3$/h, about 6 $m^3$/h, about 7 $m^3$/h, about 8 $m^3$/h, about 9 $m^3$/h, about 10 $m^3$/h, about 11 $m^3$/h, about 12 $m^3$/h, about 13 $m^3$/h, about 14 $m^3$/h, about 15 $m^3$/h, about 16 $m^3$/h, about 17 $m^3$/h, about 18 $m^3$/h, about 19 $m^3$/h, about 20 $m^3$/h, about 21 $m^3$/h, about 22 $m^3$/h, about 23 $m^3$/h, about 24 $m^3$/h, about 25 $m^3$/h, about 26 $m^3$/h, about 27 $m^3$/h, about 28 $m^3$/h, about 29 $m^3$/h, about 30 $m^3$/h, about 35 $m^3$/h, about 35 $m^3$/h, about 40 $m^3$/h, about 45 $m^3$/h, about 50 $m^3$/h, or any amount therebetween. In one implementation, the fluidization rate is between 1.5 $m^3$/h to 30 $m^3$/h.

In one implementation, the coating formation is sprayed on the one or more lyophilised microspheres in the fluidized bed using the methods and systems described herein. The spraying parameters may likewise be optimized to improve results of encapsulation and/or coating of the lyophilised microspheres described herein. In one implementation, the coating formulation is applied at a spray between about 0.5 grams per minute (g/min) and about 15 g/min, or more particularly optimized to between about 1.5 g/min and about 10 g/min. For example, the spray rate may be about 1.5 g/min, about 2.0 g/min, 2.5 g/min, 3.0 g/min, 3.5 g/min, 4.0 g/min, 4.5 g/min, 5.0 g/min, 5.5 g/min, 6.0 g/min, 6.5 g/min, 7.0 g/min, 7.5 g/min, 8.0 g/min, 8.5 g/min, 9.0 g/min, 9.5 g/min, 10.0 g/min, or any spray rate therebetween. Likewise, the atomizing rate may be optimized in one implementation to between about 0.1 bar and about 5 bar, or more particularly, between about 0.5 bar and about 1.5 bar. For example, the atomization rate may be about 0.5 bar, about 0.6 bar, about 0.7 bar, about 0.8 bar, about 0.9 bar, about 1.0 bar, about 1.1 bar, about 1.2 bar, about 1.3 bar, about 1.4 bar, about 1.5 bar, or any atomizing rate therebetween. In one implementation, the environmental humidity is optimized to between about 5% and about 50%, and more particularly, to between 10% and 20%. For example, the environmental humidity of the fluidized bed may be about 5%, about 6,%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, or any environmental humidity therebetween. The fluidization configuration may be Wurster, top, bottom, or tangential, but may be particularly optimized to a Wurster or top configuration. In one implementation, the fluidization bed has an optimized fluid rate of between about 1 cubic meters per hour ($m^3$/h) and about 30 $m^3$/h. In one particular implementation, the conditions are optimized to have a fluidization rate of between 1 $m^3$/h and 30 $m^3$/h, a spray rate of between 1.5 g/min and 10 g/min, an atomizing rate of between 0.5 bar and 1.5 bar, an environmental humidity of between 10% and 20%, and a Wurster or top spray fluidization configuration.

Modifications to standard microsphere production are used to carry out the methods and systems described herein to manufacture the compositions described herein. For example, one or more additional feed buffer tanks and one or more suitable nozzles and/or nozzle plates may be added to standard microsphere production equipment. Other modifications may be made, in particular, to a solidification system, to produce various types of shells and include compounds such as hydrocolloids, alginate, and pectin among others as described herein.

In one implementation, two liquid solutions are prepared: one liquid solution for the core and one liquid solution for the shell. A double nozzle system may be installed (i.e., a single or multi-nozzle system with annular gap nozzles) which allows for production to begin. Additional factors are important and adjustable based on size and type of compositions sought to be prepared. For example, interfacial tension, viscosities of core and shell, nozzle diameter ratio of inner and outer nozzle, and pressure ratio of core and shell may all be considered and adjusted.

In one implementation, an air brush is used to generate encapsulated lyophilised microspheres. In one implementation, a filtration membrane may be added and may reduce quantity of lyophilised microspheres exiting the chamber during air brushing. In another implementation, an aerosolizer is used.

In accordance with the methods and systems described herein, liquid is formed, followed by storage at ambient conditions for between one and two days, then microspheres are spray frozen and may be stored at −80° C. Lyophilised microspheres may be placed in a tray or rotary dryer, followed by dry dispensing microspheres into consumables and/or capsules, and, lastly, may be heat sealed with foil on plastic consumables.

The composition (e.g., encapsulated lyophilised microspheres) produced using the methods and systems disclosed herein may be coated with one or more additional compositions to provide enhanced control of microsphere release. In one implementation, the method further includes covering the shell with an outer layer, under conditions effective to surround the encapsulated microsphere with the outer layer.

In one implementation, the outer layer includes one or more of carrageenan, shellac, trehalose, paraffin wax, gelatin, hydroxypropyl methylcellulose (HPMC), fullalin, oxygen scavenger, alginate, chitosan, starch film, benzoxaborole-poly(vinyl alcohol) (benzoxaborole-PVA), pectin, polyvinylpyrrolidone (PVP), polyvinyl alcohol, or any combination thereof.

As described herein, the coating formulation that is applied to the one or more lyophilised microspheres to form a "shell" includes a composition that surrounds a core. In one implementation, a shell includes an outer layer of a microsphere and, or in the alternative, an outer layer of a macrosphere. In one implementation, the shell includes, for example, a shell material selected from the group consisting of carrageenan, shellac, trehalose, paraffin wax, gelatin, hydroxypropyl methylcellulose (HPMC), fullalin, oxygen scavenger, alginate, chitosan, starch film, benzoxaborole-poly(vinyl alcohol) (benzoxaborole-PVA), pectin, polyvinylpyrrolidone (PVP), polyvinyl alcohol, or any combination thereof. In one example, the shell may include, but is not limited to starch, cellulose, hydrocolloid, alginate, collagen, and any combination thereof. The amount of shell material includes, for example, any amount suitable to produce a desired shell result. In one implementation, the shell material is present in an amount between about 1 wt % and about 100 wt % of the shell. For example, the shell material may be present in about 1 wt %, 2 wt %, 3 wt %, 4 wt %, 5 wt %, 6 wt %, 7 wt %, 8 wt %, 9 wt %, 10 wt %, 15 wt %, 20 wt %, 25 wt %, 30 wt %, 35 wt %, 40 wt %, 45 wt %, 50 wt %, 60 wt %, 70 wt %, 80 wt %, 90 wt %, 100 wt %, of the shell, or any amount therebetween. In one implementation, the shell material is present in an amount between about 10 wt % and about 90 wt %, or between about 10 wt % and about 80 wt %, or between about 10 wt % and about 70 wt %, or between about 10 wt % and about 60 wt %, or between about 10 wt % and about 50 wt %, of the shell.

The shell, as described herein, may include one layer or a plurality of layers of varying compositions. For example, the shell may include one layer, two layers, three layers, four layers, five layers, six layers, seven layers, eight layers, nine layers, ten layers, or more than ten layers. Each of the layers may include the same or different materials from the other layers that are present in the shell.

The shell as described herein, may, in one implementation, include a shell additive. The shell additive may be present in an amount between about 0.01% w/w of the shell and about 99% w/w of the shell. In one implementation, the shell additive is present in an amount between about 10% w/w and about 90% w/w of the shell. In one implementation, the shell additive is present in an amount between about 10% w/w and about 40% w/w. In one implementation, the shell additive is a static mitigation material present in an amount no more than 40% w/w concentration of the shell. In one implementation, the shell additive is a moisture barrier material present in an amount no more than 90% w/w of the shell. In one implementation, the shell additive is present in an amount of at least 10% w/w concentration of the shell. For example, the shell additive may, in one implementation, be present in an amount between 0.1% w/w of the shell and about 15.0% w/w of the shell. For example, the shell additive may be present in an amount of about 0.01% w/w, 0.05% w/w, 0.1% w/w, 0.5% w/w, 1.0% w/w, 1.5% w/w, 2.0% w/w, 2.5% w/w, 3.0% w/w, 3.5% w/w, 4.0% w/w, 4.5% w/w, 5.0% w/w, 5.5% w/w, 6.0% w/w, 6.5% w/w, 7.0% w/w, 7.5% w/w, 8.0% w/w, 8.5% w/w, 9.0% w/w, 9.5% w/w, 10.0% w/w, 10.5% w/w, 11.0% w/w, 11.5% w/w, 12.0% w/w, 12.5% w/w, 13.0% w/w, 13.5% w/w, 14.0% w/w, 14.5% w/w, 15% w/w, or any amount therebetween. The amount of shell additive may be any suitable amount to, for example, reduce tribocharging of the compositions described herein and/or provide a suitable moisture barrier. The amount of the shell additive may be adjusted to accommodate a particular reagent or combination of reagents, or to accommodate a particular microsphere composition.

In one implementation, the shell additive comprises a static mitigation material, a moisture barrier material, or a combination thereof. In one implementation, the shell additive is a static mitigation material present in an amount no more than 40% w/w concentration of the shell. In one implementation, the shell additive is a moisture barrier material present in an amount no more than 90% w/w concentration of the shell. In one implementation, the shell additive is present in an amount of at least 10% w/w concentration of the shell. In one implementation, the shell additive is in an amount between about 10% w/w and about 90% w/w of the shell. In one implementation, the shell additive is a water-insoluble additive, a water-soluble additive, an entero-soluble additive, or any combination thereof. In one implementation, the shell additive comprises one or more of a polymer, a copolymer, a block copolymer, a second polyvinyl alcohol (PVA), an ammonium salt, a conductivity promoter, a stearate derivative, an oleate derivative, a laurate derivative, a polyether compound, an amino acid, tocopherol acetate, piperidyl sebacate, sodium salt, a buffer, a chelating agent, imidazolium salt, polyaniline, or any combination thereof. In one implementation, the polyether compound is selected from polyethylene glycol, polypropylene glycol, a block copolymer derived from ethylene oxide (EO) and propylene oxide (PO), or any combination thereof. In one implementation, the stearate derivative or oleate derivative is selected from magnesium stearate, triglycerol stearate, Span® 60, Tween® 60, glycerol trioleate, Tween® 80, or any combination thereof. In one implementation, the amino acid is selected from one or more of leucine, isoleucine, phenylalanine, or any combination thereof. In one implementation, the polymer is neutral, cationic, or anionic. In one implementation, the sodium salt is selected from one or more of sodium chloride, sodium bisulfite, sodium citrate, or any combination thereof. In one implementation, the buffer is Trizma, Tris.HCl, or a combination thereof. In one implementation, the ammonium salt is selected from tetraalkyl ammonium chloride, tris(hydroxyethyl) alkylammonium chloride, or a combination thereof. In one implementation, the imidazolium salt is selected from 1-ethyl-3-methyl-imidazolium salt or polyquaternium or Luviquat® (copolymer of vinyl pyrrolidone and quaternized vinylimidazole) or a combination thereof. In one implementation, the shell additive comprises ammonium salt, copolymer, polyvinyl alcohol graft polyethylene glycol copolymer, polyvinyl alcohol (PVA), or any combination thereof. The shell may be comprised of polymers, and the maximum concentration of the polymer in the shell may be about 90% (in dry format). One or more static mitigating additive may be added into the polymer coating, and a range between about 10% and about 40% of the shell additive may be present in the shell in dry format.

In various implementations, the shell additive may include a beneficial combination of compounds for improved and unexpected compatibility with SBS reagents. For example, the shell additive may include a polyether compound and a polymer and/or copolymer, or alternatively, a polyether compound, a PVA, and/or a polymer and/or copolymer. In one implementation, the shell additive includes polyethylene glycol, Kollidon® VA64, and Efka® IO 6783, or their chemical equivalent. In another implementation, the shell additive includes polyethylene glycol and Kollidon® VA64, or their chemical equivalent. In another implementation, the shell additive includes polyethylene glycol, Kollicoat® Protect, and Efka® IO 6783®, or their chemical equivalent. In yet another implementation, the shell additive includes polyethylene glycol and Kollicoat® Protect, or their chemical equivalent. In one implementation, the ammonium salt acts as a conductivity promoter. In one implementation, the imidazolium salt acts as a conductivity promoter.

As described herein, the one or more lyophilised microspheres include a "core" or "core region" that includes any material within the surrounding shell (i.e., the encapsulated portion). A core in accordance with the present disclosure comprises one or more lyophilised microspheres. In one implementation, at least two lyophilised microspheres are provided.

As used herein, the term "compatible" means able to exist or occur together without conflict, that is for example, without substantially degrading the performance or activity of one or more substances that exist or occur together. Likewise, as used herein, the term "incompatible" means unable to exist or occur together without conflict, that is for example, without substantially degrading the performance or activity of one or more substances that exist or occur together.

Lyophilisation in accordance with the present disclosure includes methods in accordance with conventional techniques, which are known to those skilled in the art. Lyophilisation is also referred to herein as freeze-drying. In the present disclosure, the term "lyophilize" or "lyophilizate" will be used as equivalent terms of "lyophilised", "lyophilizate", or "freeze-dried" e.g., with respect to the methods or systems described herein.

Lyophilisable formulations can be reconstituted into solutions, suspensions, emulsions, or any other suitable form for administration or use. Lyophilisable formulations are typically first prepared as liquids, then frozen and lyophilised. The total liquid volume before lyophilisation can be less than, equal to, or more than, the final reconstituted volume of the lyophilised formulation. Preferably, the final reconstituted volume of the lyophilised formulation is less than the total liquid volume before lyophilisation. The lyophilisation process is known to those of ordinary skill in the art, and typically includes sublimation of water from a frozen formulation under controlled conditions.

Lyophilised formulations can be stored at a wide range of temperatures. Lyophilised formulations may be stored below 25° C., for example, refrigerated at 2-8° C., or at room temperature (e.g., approximately 25° C.). Preferably, lyophilised formulations are stored below about 25° C., more preferably, at about 4-20° C.; below about 4° C.; below about −20° C.; about −40° C.; about −70° C., or about −80° C. Stability of the lyophilised formulation may be determined in a number of ways known in the art, for example, by visual appearance of the microsphere and/or cake and/or by moisture content. The methods and systems of the present disclosure can produce encapsulated lyophilised microspheres that withstand temperature excursions that might occur during shipping, for example, up to 70° C., for brief periods of time.

Lyophilised formulations are typically rehydrated (interchangeably referred to herein as "reconstituted") for use by addition of an aqueous solution to dissolve the lyophilised formulation. A wide variety of aqueous solutions can be used to reconstitute a lyophilised formulation including water, saline, or another electrolyte or non-electrolyte diluent. Preferably, the lyophilised microspheres described herein are reconstituted using water. Lyophilised formulations may be rehydrated with a solution comprising water (e.g., USP WFI, or water for injection) or bacteriostatic water (e.g., USP WFI with 0.9% benzyl alcohol). However, solutions comprising additives, buffers, excipients, and/or carriers can also be used and are described herein.

Freeze-dried or lyophilised formulations are typically prepared from liquids, that is, from solutions, suspensions, emulsions, and the like. Thus, the liquid that is to undergo freeze-drying or lyophilisation preferably comprises all components desired in a final reconstituted liquid formulation. As a result, when rehydrated or reconstituted, the freeze-dried or lyophilised formulation will render a desired liquid formulation upon reconstitution.

In one implementation, the core includes, but is not limited to, one or more reagents, for example, one or more enzyme, salt, surfactant, buffering agent, enzyme inhibitor, primer, nucleotide, organic osmolite, magnetic bead, molecular probe, crowding agent, small molecule, labelled-nucleotide, or any combination thereof. In a preferred implementation, the core is not an aqueous medium.

As used herein, the term "reagent" describes a single agent or a mixture of two or more agents useful for reacting with, interacting with, diluting, or adding to a sample, and may include agents used in nucleic acid reactions, including, for example buffers, chemicals, enzymes, polymerase, primers including those having a size of less than 50 base pairs, template nucleic acids, nucleotides, labels, dyes, or nucleases. A reagent as described herein may, in certain implementations, include enzymes such as polymerases, ligases, recombinases, or transposases; binding partners such as antibodies, epitopes, streptavidin, avidin, biotin, lectins or carbohydrates; or other biochemically active molecules. Other examples reagents include reagents for a biochemical protocol, such as a nucleic acid amplification protocol, an affinity-based assay protocol, an enzymatic assay protocol, a sequencing protocol, and/or a protocol for analyses of biological fluids. According to some of implementations disclosed herein, a reagent may include one or more beads, in particular magnetic beads, depending on specific workflows and/or downstream applications. In one implementation, the at least one lyophilised microsphere comprises one or more reagent. In one implementation, the one or more reagent comprises at least a first reagent and a second reagent. In one implementation, the first reagent and the second reagent are different.

In one implementation, a reagent in accordance with the present disclosure is a polymerase. Polymerase in accordance with the present disclosure may include any polymerase that can tolerate incorporation of a phosphate-labeled nucleotide. Examples of polymerases that may be useful in accordance with the present disclosure include but are not limited to phi29 polymerase, a klenow fragment, DNA polymerase I, DNA polymerase III, GA-1, PZA, phi15, Nf, G1, PZE, PRD1, B103, GA-1, 9oN polymerase, Bst, Bsu, T4, T5, T7, Taq, Vent, RT, pol beta, and pol gamma. Polymerases engineered to have specific properties may be used. In one example, the core region may include, but is not limited to, polishing microspheres, sequencing microspheres, and any combination thereof. Polishing microspheres as described herein may include, but are not limited to, ffNs, polymerase useful for polishing ("polishing polymerase"), oligo useful for polishing ("polishing oligo"), magnesium enzyme co-factor, and any combination thereof. In another example, sequencing microspheres may include, but are not limited to, polymerase useful for sequencing ("sequencing polymerase").

A primer as disclosed herein includes a nucleic acid molecule that can hybridize to a target sequence of interest. In several implementations, a primer may function as a substrate onto which nucleotides can be polymerized by a polymerase. However, in some examples, the primer can become incorporated into the synthesized nucleic acid strand and provide a site to which another primer can hybridize to prime synthesis of a new strand that is complementary to the synthesized nucleic acid molecule. The primer can include any combination of nucleotides or analogs thereof. In some examples, the primer is a single-stranded oligonucleotide or polynucleotide.

Non-limiting examples of nucleic acid molecules that may be encapsulated within the microsphere include those described above, for example, DNA, such as genomic or cDNA; RNA, such as mRNA, sRNA or rRNA; or a hybrid of DNA and RNA. The core may further comprise a labelled-nucleotide.

The term "salt" may include salts prepared from toxic or non-toxic acids or bases including inorganic acids and bases and organic acids and bases. Salts may be prepared from, for example, pharmaceutically acceptable non-toxic acids including inorganic and organic acids.

Any surfactant known to one skilled in the art may be used as a reagent in the core. The surfactant may be non-ionic or ionic (specifically cationic or anionic) or may be zwitterionic. Examples of suitable surfactants include but are not limited to polyacrylate surfactants, silicone surfactants, and/or other commercially available surfactants or detergents. Examples of cationic surfactants are cetyldimethylammonium acetamide, octadecyl-dimethylammonium acetamide, tetradecyl-dimethylammonium acetamide, dodecyl-dimethylammonium acetamide, cetyltrimethylammonium, octadcecyl-trimethylammonium, tetradecyl-trimethylammonium, dodecyl-trimethylammonium, dimethyl-dioctadecylammonium, dioctadecyldimethylammonium, and mixtures thereof. Suitable sources of these cations of the cationic surfactant include, but are not limited to, alkyltrimethylammonium salts: such as cetyl trimethylammonium bromide (CTAB) or cetyl trimethylammonium chloride (CTAC); cetylpyridinium chloride (CPC); dimethyldioctadecylammonium chloride; dioctadecyldimethylammonium bromide (DODAB); cetyldimethylammonium acetamide bromide; or other cationic surfactant alike, including lipids. Alternatively, the surfactant may be benzyl hexadecyl dimethyl ammonium chloride (BHDC). The core may include an anionic surfactant which contains an anionic functional group at one end, such as a sulfate, sulfonate, phosphate, and carboxylate functional group. One example of an anionic surfactant is sodium dodecyl sulfate. The core may comprise a neutral surfactant, for example, a polyethelene glycol lauryl ether.

The core may further, or in the alternative, include an enzyme inhibitor, a molecular probe, a crowding agent, organic osmolite, cyclodextrin, adenosine triphosphate (ATP), ethylenediaminetetraacetic acid (EDTA), creatine kinase, creatine phosphate, palladium, lipoic acid, hexaethylene glycol, trihydroxypropanephosphine, sodium ascorbate, or any combination thereof. An enzyme inhibitor as described herein includes any a molecule that binds to an enzyme and decreases its activity. A molecular probe as described herein includes, for example, digoxigenin, 8-Anilinonaphthalene-1-sulfonic acid ("ANS"), porphyrin, BODIPY, cyanine, or any combination thereof. A crowding agent as described herein includes any crowding agent known to those skilled in the art. Examples include, but are not limited to, polyethylene glycol, ficoll, dextran, and serum albumin.

Those skilled in the art of sequencing technologies will appreciate there are additional reagents that may be useful in the methods and systems of the present disclosure that are not explicitly described herein.

The core as described herein may, in one implementation, further include one or more additional agents. The one or more additional agent in the core improves the ability to control the release of one or more lyophilised microspheres. In one implementation, the additional agent is selected from one or more sugars, amino acids, polymers, mesoporous silica, quaternary amines, or any combination thereof. In one implementation, when the additional agent comprises sugar, the sugar is selected from trehalose, mannitol, cyclodextrin, dextran, or any combination thereof. In another implementation, when the additional agent comprises an amino acid, the amino acid has a hydrophobic side chain. In another implementation, when the additional agent comprises a polymer, the polymer is selected from polyvinylpyrrolidone, polyvinyl alcohol, or a combination thereof. In some implementations, the additional agent may be, for example, one or more co-polymers, ionic liquids, or any combination thereof. The additional agent may be added in any amount suitable to produce a desired effect, for example, between about 0.1 wt % and about 50 wt % of the core. In one implementation, the concentration of the additional agent in the core is about 0.1 wt %, 0.5 wt %, 1 wt %, 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 20 wt %, 25 wt %, 30 wt %, 35 wt %, 40 wt %, 45 wt %, or any amount therebetween.

In one implementation, the core further includes a core additive. The core additive may be present in an amount between about 0.01% w/w of the core and about 100% w/w of the core. For example, the core additive may, in one implementation, be present in an amount between 0.1% w/w of the core and about 20.0% w/w of the core. In one implementation, the core additive may be between about 2% w/w and about 10% w/w of the core. For example, the core additive may be present in an amount of about 0.01% w/w, 0.05% w/w, 0.1% w/w, 0.5% w/w, 1.0% w/w, 1.5% w/w, 2.0% w/w, 2.5% w/w, 3.0% w/w, 3.5% w/w, 4.0% w/w, 4.5% w/w, 5.0% w/w, 5.5% w/w, 6.0% w/w, 6.5% w/w, 7.0% w/w, 7.5% w/w, 8.0% w/w, 8.5% w/w, 9.0% w/w, 9.5% w/w, 10.0% w/w, 10.5% w/w, 11.0% w/w, 11.5% w/w, 12.0% w/w, 12.5% w/w, 13.0% w/w, 13.5% w/w, 14.0% w/w, 14.5% w/w, 15.0% w/w, 15.5% w/w, 16.0% w/w, 16.5% w/w, 17.0% w/w, 17.5% w/w, 18.0% w/w, 18.5% w/w, 19.0% w/w, 19.5% w/w, 20.0% w/w or any amount therebetween. The amount of core additive may be any suitable amount to reduce tribocharging of the compositions described herein. The amount of the core additive may be adjusted to accommodate a particular reagent or combination of reagents, or to accommodate a particular microsphere composition.

In one implementation, the core additive comprises a static mitigation material. In one implementation, the core additive is a static mitigation material present in an amount no more than 25% w/w concentration of the core. In one implementation, the core additive is present in an amount of at least 0.5% w/w concentration of the core. In one implementation, the core additive is in an amount between about 2% w/w and about 10% w/w of the core. In one implementation, the core additive is a water-insoluble additive, a water-soluble additive, an entero-soluble additive, or any combination thereof. In one implementation, the core additive comprises one or more of a polymer, a copolymer, a block copolymer, a second polyvinyl alcohol (PVA), a conductivity promoter, an ammonium salt, an imidazolium salt, a polyether compound, or any combination thereof. In one implementation, the polyether compound is selected from polyethylene glycol, polypropylene glycol, a block copolymer derived from ethylene oxide (E0) and propylene oxide (PO), or any combination thereof. In one implementation, the polymer is neutral, cationic, or anionic. In one implementation, the buffer is Trizma, Tris.HCl, or a combination thereof. In one implementation, the ammonium salt is selected from tetraalkyl ammonium chloride, tris(hydroxyethyl) alkylammonium chloride, or a combination thereof. In one implementation, the imidazolium salt is selected from 1-ethyl-3-methyl-imidazolium salt or polyquaternium or Luviquat® (copolymer of vinyl pyrrolidone and quaternized vinylimidazole) or a combination thereof. In one implementation, the compositions produced by the methods and systems described herein may be manufactured from about 20% lyophilized formulation (i.e., the formulation contains 20% lyophilised excipient, such as trehalose and other additives). Therefore, the additive (static mitigating or moisture protection) may be incorporated and/or spiked into the lyophilised formulation, followed by drying to give an appropriate concentration in dry format. In one implementation, the ammonium salt acts as a conductivity promoter. In one implementation, the imidazolium salt acts as a conductivity promoter.

The core additive described herein may, in one implementation, include a water-insoluble additive, a water-soluble additive, an entero-soluble additive, or any combination thereof. In one implementation, the core additive may include one or more of a sodium salt, a buffer, a chelating agent, an ammonium salt, imidazolium salt, polyaniline, or any combination thereof. In one implementation, one or more water-soluble core additives are added to the core. In one implementation, the sodium salt is selected from one or more of sodium chloride, sodium bisulfite, sodium citrate, or any combination thereof. In another implementation, the buffer is Trizma (Tris.HCl). In one implementation, the ammonium salt is selected from tetraalkyl ammonium chloride, tris(hydroxyethyl) alkylammonium chloride, or any combination of thereof. In one implementation, the imidazolium salt is selected from 1-ethyl-3-methyl-imidazolium salt or polyquaternium or Luviquat® (copolymer of vinyl pyrrolidone and quaternized vinylimidazole) or a combination thereof. In another implementation, one or more water-soluble additive such as Efka® IO 6783, Efka® IO 6786, Tween® 80, Makon® 17R4, lauric acid diethanolamide, or any combination of one or more of these additives may be included in the core additive composition. In another implementation, one or more water-insoluble additive such as trioleate glycerol, polyaniline, piperidyl sebacate, an amino acid, vitamin E (tocopherol acetate), Span® 60, or any combination of one or more of these additives may be included in the core additive composition. In one implementation, Efka® IO 6783 is used as a core additive in an amount suitable to reduce tribocharging behavior of the composition (for example, an amount of about 5% w/w of the core).

The composition (i.e., encapsulated lyophilised microsphere) produced by the methods and systems described herein may be any appropriate size or volume that is able to encapsulate one or more reagents and suitable for use in library preparation for sequencing. In one implementation, the composition has a volume of reagent in the core region of between about 0.1 μL and about 50 μL. For example, the composition (i.e., encapsulated lyophilised microsphere) may have an active reagent volume of about 0.1 μL, 0.5 μL, 1 μL, 2 μL, 3 μL, 4 μL, 5 μL, 6 μL, 7 μL, 8 μL, 9 μL, 10 μL, 15 μL, 20 μL, 25 μL, 30 μL, 35 μL, 40 μL, 45 μL, 50 μL, or any volume between about 0.1 μL and about 50 μL. In one implementation, the active reagent volume is between about 10 μL and about 40 μL. The composition (i.e., encapsulated lyophilised microsphere) may have a diameter of, for example, about 2 μm to about 120 μm, such as, for example, 2, 3, 4, 5, 6, 7, 8, 9, 10, 15, 20, 25, 30, 35, 40, 45, 50, 60, 70, 80, 90, 100, 110, or 120 μm in diameter, or a diameter within a range defined by any two of the aforementioned values.

The composition produced using the methods and systems described herein may include an additional reagent in the shell of the microsphere. In one implementation, the encapsulated microsphere includes a reagent or additive in the microsphere shell. The reagent in the shell may include, for example, any of the foregoing reagents or additives. In one implementation, the shell contains no nucleic acid molecules, for example, the shell contains no DNA. In one implementation, the shell contains more than one reagent and, or in the alternative, more than one additive.

Likewise, the composition (e.g., encapsulated lyophilised microsphere) produced using the methods and systems described herein may include a low oxygen permeability polymer coating, for example, polyvinyl alcohol and/or oxygen scavenger. Similarly, the composition (e.g., encapsulated lyophilised microspheres) produced by the methods and systems described herein may include amphiphilic coating, for example, amino acids and/or PVP co-polymers. The encapsulated lyophilised microspheres described herein may further provide protection from mechanical stress, for example, by preventing fragmentation in manufacturing, for example, with a 40% solute content shell. The compositions (e.g., encapsulated lyophilised microspheres) produced by the methods and systems described herein may further provide protection from light exposure, as the reagents may be protected from light exposure thereby decreasing manufacturing light constraints.

The compositions produced by the methods and systems described herein may be used for multiple sequential co-assays comprising lysis, DNA analysis, RNA analysis, protein analysis, tagmentation, nucleic acid amplification, nucleic acid sequencing, DNA library preparation, SBS technology, assay for transposase accessible chromatic using sequencing (ATAC-seq), contiguity-preserving transposition (CPT-seq), single cell combinatorial indexed sequencing (SCI-seq), or single cell genome amplification, or any combination thereof performed sequentially. In one implementation, the composition is used for performing multiple co-assay reactions. The methods and systems described herein (e.g., encapsulation of lyophilised microspheres) may, in one implementation, be used to produce compositions that improve sequencing quality, enable one-pot library prep, and simplify manufacturing. As used herein, the term "one-pot reaction" may also be referred to as "transfer-free reaction."

The methods and systems described herein may be used to prepare compositions for various stages of sequencing including, but not limited to, sample extraction, library preparation, enrichment, clustering, and sequencing. In sample extraction compositions, the core may include enzymes, salt, surfactants, buffering agents, and any combination thereof. The sample extraction may occur at a pH of about 7.5 with a reaction volume of between about 1 mL and about 5 mL. In library preparation compositions, the core may include enzyme inhibitors, salts, primers, enzymes, nucleotides, organic osmolites, magnetic beads, and any combination thereof. Library preparation may occur at a pH of about 7 with a reaction volume of about 0.05 mL. In enrichment compositions, the core may include nucleotides, molecular probes, enzymes, magnetic beads, crowding agents, and any combination thereof. Enrichment may occur at a pH of about 8.5 with a reaction volume of between about 0.1 mL and about 0.2 mL. In clustering compositions, the core may include salts, enzymes, one or more nucleotides, small molecules, surfactants, primers, and any combination thereof. Clustering may occur at a pH of about 8.6 with a reaction volume of between about 1 mL and about 5 mL. In sequencing compositions, the core may include labelled-nucleotides, a fluorophore, surfactants, salts, enzymes, small molecules, and any combination thereof. Sequencing may occur at a pH of between about 7 and about 10 with a reaction volume of about 30 mL to about 100 mL.

In one implementation, the shell may rehydrate under a pH between 1 and 14. In one implementation, the shell may include one or more shell layers and each layer may rehydrate under the same or different conditions. For example, the shell may include a plurality of layers that rehydrate under different conditions. In one implementation, the shell may include two or more layers (e.g., three or more layers) that release at different pH levels, for example, one layer may release at a pH of 5, one layer may release at a pH of 5.5, one layer may release at a pH of 6, one layer may release at a pH of 6.5, one layer may release at a pH of 7, one layer may release at a pH of 7.5, and/or one layer may release at a pH of 8.

The core may include any number of different reagents from those described herein or any reagent that may be useful in promoting utility of sequencing systems, for example, SBS technology.

The water content of the coating formulation (i.e., composition that forms a shell) may be optimized to improve results of the methods and systems described herein. In one implementation, the coating formulation comprises a water content of between about 0.1 wt. % and about 25 wt. %. For example, the coating formation may include a water content of about 0.1 wt. %, 0.2 wt. %, 0.3 wt. %, 0.4 wt. %, 0.5 wt. %, 0.6 wt. %, 0.7 wt. %, 0.8 wt. %, 0.9 wt. %, 1 wt. %, 1.5 wt. %, 2 wt. %, 2.5 wt. %, 3 wt. %, 3.5 wt. %, 4 wt. %, 4.5 wt. %, 5 wt. %, 5.5 wt. %, 6 wt. %, 6.5 wt. %, 7 wt. %, 7.5 wt. %, 8 wt. %, 8.5 wt. %, 9 wt. %, 9.5 wt. %, 10 wt. %, 10.5 wt. %, 11 wt. %, 11.5 wt. %, 12 wt. %, 12.5 wt. %, 13 wt.

%, 13.5 wt. %, 14 wt. %, 14.5 wt. %, 15 wt. %, 15.5 wt. %, 16 wt. %, 16.5 wt. %, 17 wt. %, 17.5 wt. %, 18 wt. %, 18.5 wt. %, 19 wt. %, 19.5 wt. %, 20 wt. %, 20.5 wt. %, 21 wt. %, 21.5 wt. %, 22 wt. %, 22.5 wt. %, 23 wt. %, 23.5 wt. %, 24 wt. %, 24.5 wt. %, 25 wt. %, or any amount therebetween.

Similarly, the water content of the encapsulated lyophilised microspheres (i.e., composition that forms a core) may be optimized to improve results of the methods and systems described herein. In one implementation the encapsulated lyophilised microspheres comprise a water content of below about 10 wt. %. For example, the water content of the encapsulated lyophilised microspheres may be about 0.9 wt. %, about 0.8 wt. %, about 0.7 wt. %, about 0.6 wt. %, about 0.5 wt. %, about 0.4 wt. %, about 0.3 wt. %, about 0.2 wt. %, about 0.1 wt. %, below 0.1 wt. %, or any amount therebetween.

In one implementation, a biological sample contacts the composition. A biological sample, may include, for example, whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, liquids containing multi-celled organisms, biological swabs and biological washes. A biological sample can include nucleic acids, such as DNA, genomic DNA, RNA, mRNA or analogs thereof; nucleotides such as deoxyribonucleotides, ribonucleotides or analogs thereof such as analogs having terminator moieties such as those described in Bentley et al., "Accurate Whole Human Genome Sequencing Using Reversible Terminator Chemistry," Nature 456:53-59 (2008); WO/2013/131962; U.S. Pat. No. 7,057,026; WO/2008/042067; WO/2013/117595; U.S. Pat. Nos. 7,329,492; 7,211,414; 7,315,019; 7,405,281; and U.S. Patent Pub. No. 20080108082, all of which are hereby incorporated by reference in their entirety.

Any suitable method can be used to form microspheres. Standard microsphere manufacturing techniques will be known to those skilled in the art, and include, preparing frozen pellets and placing those pellets in a dryer as described herein. A variety of microspheres are contemplated in accordance with the methods and systems of the present disclosure and include, for example, time sustained release, immediate pulse, timed pulsative release, organic acid Diffucaps® Bead, and alkaline buffer Diffucaps® Bead microspheres. There are also a variety of types of encapsulation encompassed by the methods and systems described herein, including, but not limited to, bulk-, micro-, nano-, single molecule, and ionic encapsulation.

A second aspect relates to encapsulating lyophilised microspheres in accordance with aspects of the present disclosure, in particular with regard to the characteristics of the one or more lyophilised microspheres and their coating, shell, core, and encapsulation. Lyophilised microspheres may include one or more reagent, such as, for example, one or more enzyme, salt, surfactant, buffering agent, enzyme inhibitor, primer, nucleotide, organic osmolite, magnetic bead, molecular probe, crowding agent, small molecule, labelled-nucleotide, a fluorophore, or any combination thereof. A nucleotide may include a typical or atypical natural nucleotide or synthetic nucleotide that includes one or more covalently attached modification (e.g., tags for visualization, blocking moieties to prevent polymerization, etc.). An enzyme or protein may include, as non-limiting examples, a polymerases such as a DNA polymerase or RNA polymerase, a transposase (e.g., bead-linked transposases, such as Tn5, or bead-linked transposomes), a proteinase such as proteinase K, a recombinase enzyme, a nucleotide binding protein such as a single-stranded polynucleotide binding protein, or any combination of two or more of the foregoing.

It should be appreciated that all combinations of the foregoing concepts and additional concepts discussed in greater detail herein (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

In the present disclosure, reference is made to the accompanying drawings that form a part hereof, and in which is shown by way of illustration specific implementations which may be practiced. These implementations are described in detail to enable those skilled in the art to practice the disclosure, and it is to be understood that other implementations may be utilized and that structural, logical and electrical changes may be made without departing from the scope of the present disclosure. The following description of example implementations is, therefore, not to be taken in a limited sense.

The present disclosure may be further illustrated by reference to the following examples.

EXAMPLES

The following examples are intended to illustrate, but by no means are intended to limit, the scope of the present disclosure as set forth in the appended claims.

Example 1— Encapsulated Lyophilised Microsphere Production

Here, encapsulated lyophilised microspheres are produced.

A workflow for production of encapsulated lyophilised microspheres described herein is shown in FIG. 1. FIG. 1 shows examples of spray freezing, freeze drying, and fluid bed encapsulation to produce an encapsulated lyophilised microsphere. One implementation of producing coated microspheres is depicted in FIG. 1. Microspheres are inside a chamber and coating is applied to microspheres using an air brush. The air brush may generate significant air drafts in the chamber which results in some microspheres leaving the chamber. A filtration membrane is added to prevent the microspheres from leaving the chamber. An aerosolizer may be used instead of an air brush to generate less air flow.

Figure 2:
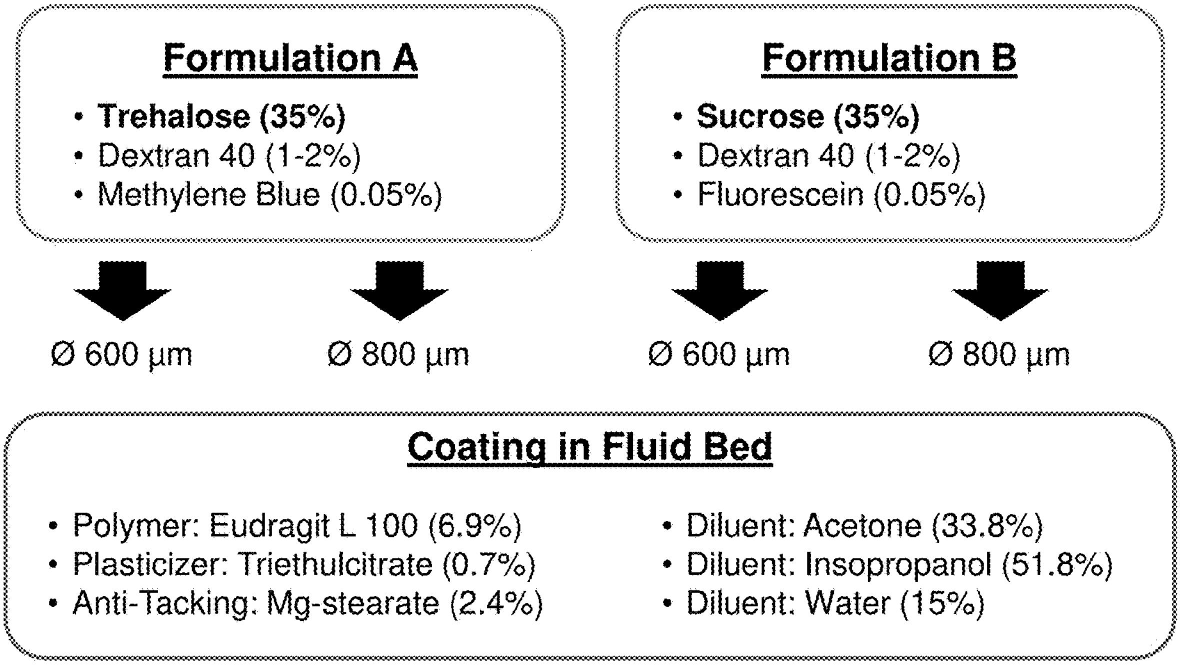
FIG. 2 shows exemplary formulations for fluid bed encapsulation.
Figure 3:
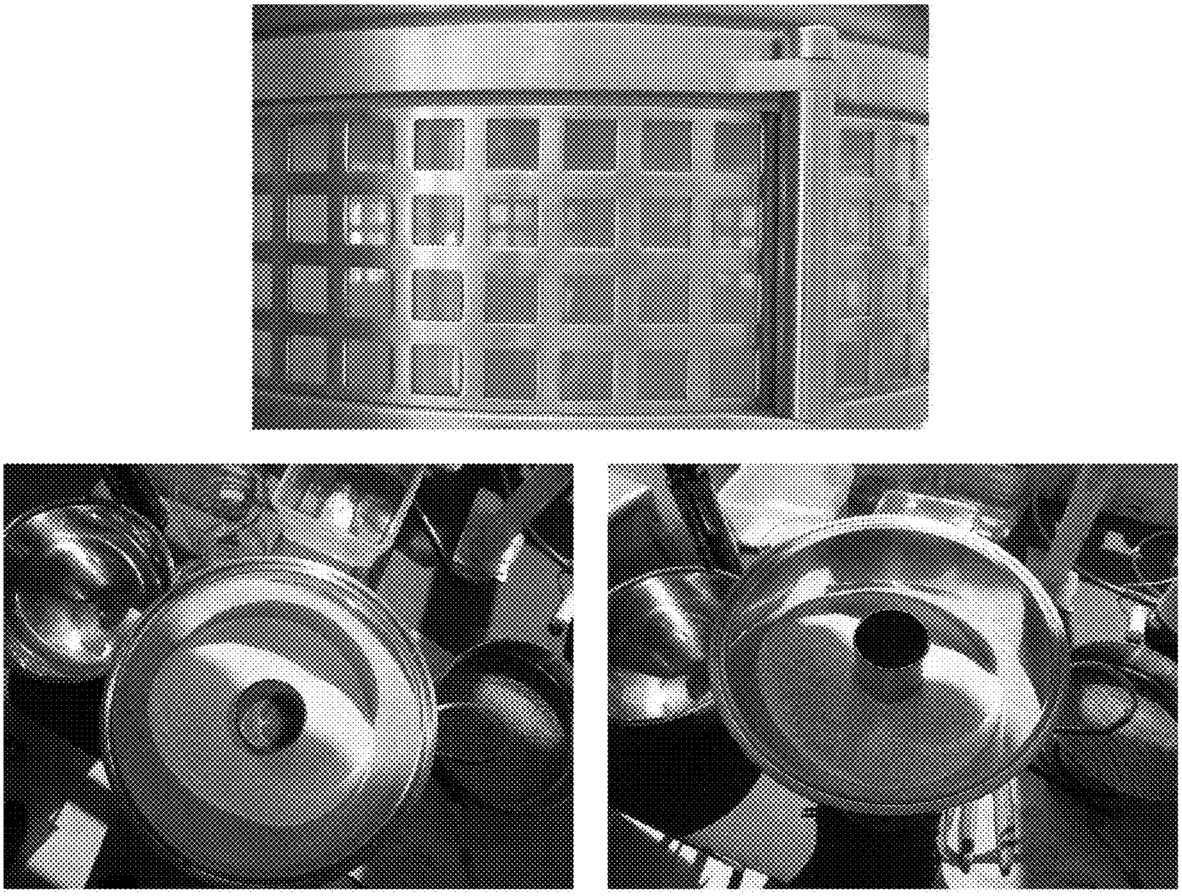
FIG. 3 depicts microspheres in a fluid bed.
Figure 20:
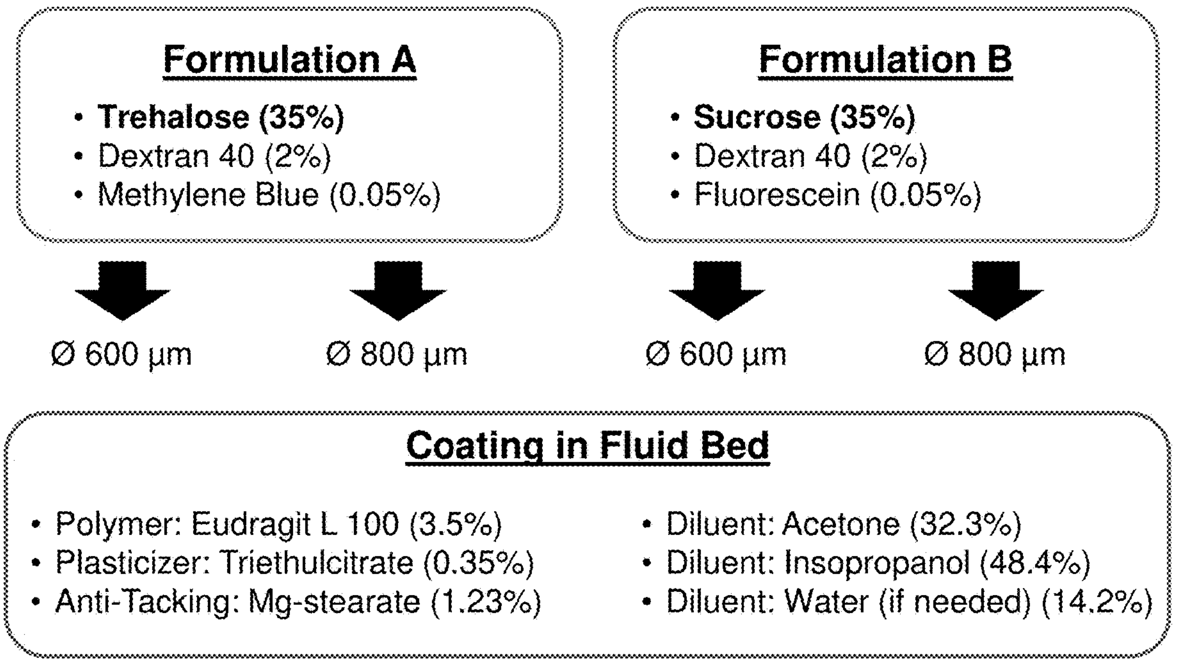
FIG. 20 shows further exemplary formulations for fluid bed encapsulation.

Exemplary formulations for fluid bed encapsulation are shown in FIG. 2. In one implementation, a first formulation may include trehalose (35%), dextran 40 (1-2%), methylene blue (0.05%); a second formulation may include sucrose (35%) dextran 40 (1-2%), and fluorescein (0.05%). The first and second formulations may be coated in a fluid bed using a coating composition that includes, for example, a polymer (Eudragit L 100 (6.9%)), a plasticizer (triethylcitrate (0.7%)), an anti-tacking composition Mg-stearate (2.4%), and one or more diluent (acetone (33.8%) and isopropanol (51.8%) and water (15%)). Further exemplary formulations for fluid bed encapsulation are shown in FIG. 20. In one implementation, a first formulation may include trehalose (33%), dextran 40 (2%), methylene blue (0.05%); a second formulation may include sucrose (33%) dextran 40 (2%), and fluorescein (0.05%). The first and second formulations may be coated in a fluid bed using a coating composition that includes, for example, a polymer (Eudragit L 100 (3.5%)), a plasticizer (triethylcitrate (0.35%)), an anti-tacking composition Mg-stearate (1.23%), and one or more diluent (acetone (32.3%) and isopropanol (48.4%) and optionally water (14.2%)). An example of microspheres in a fluid bed is depicted in FIG. 3.

An important factor in preparing encapsulated microspheres is wetness of solution. If too much wetness is present in the lyophilised microspheres, agglomeration will occur. It too little wetness is present in the lyophilised microspheres, static charge will occur and the lyophilised microspheres will irregularly stick to the fluid bed making it difficult to evenly coat and/or encapsulate the lyophilised microspheres.

Figure 4:
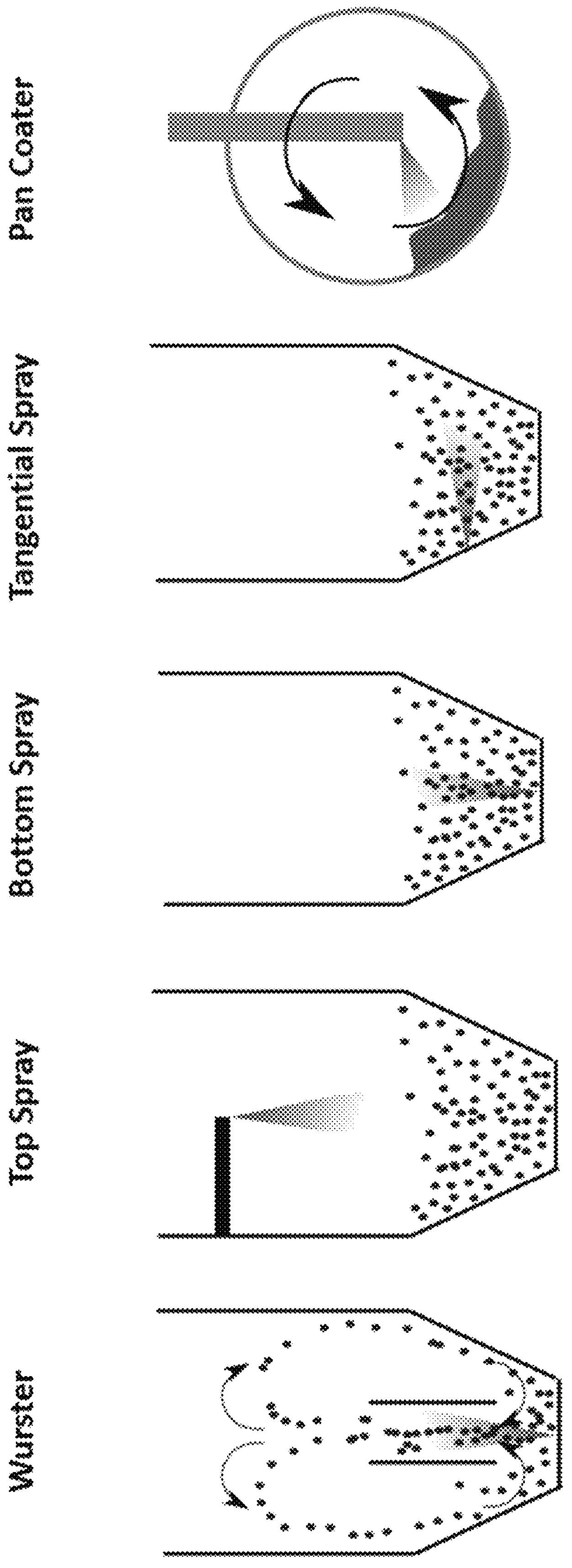
FIG. 4 shows five configurations for encapsulating lyophilised microspheres as described herein.

Various processes and configurations were tested for encapsulating lyophilised microspheres as described herein. See FIG. 4. For example a Wurster configuration was tested, which includes a bottom spray through a tube to control the flow. A Top Spray configuration was also tested, which includes spraying from the top while fluidizing from the bottom. A bottom spray was similarly tested, which includes spraying from the bottom while fluidizing from the bottom. A tangential spray was tested as well, which includes spraying from the side while fluidizing from the bottom. A Pan Coater configuration was likewise tested, which includes a rotational drum while spraying from the center.

Figure 5:
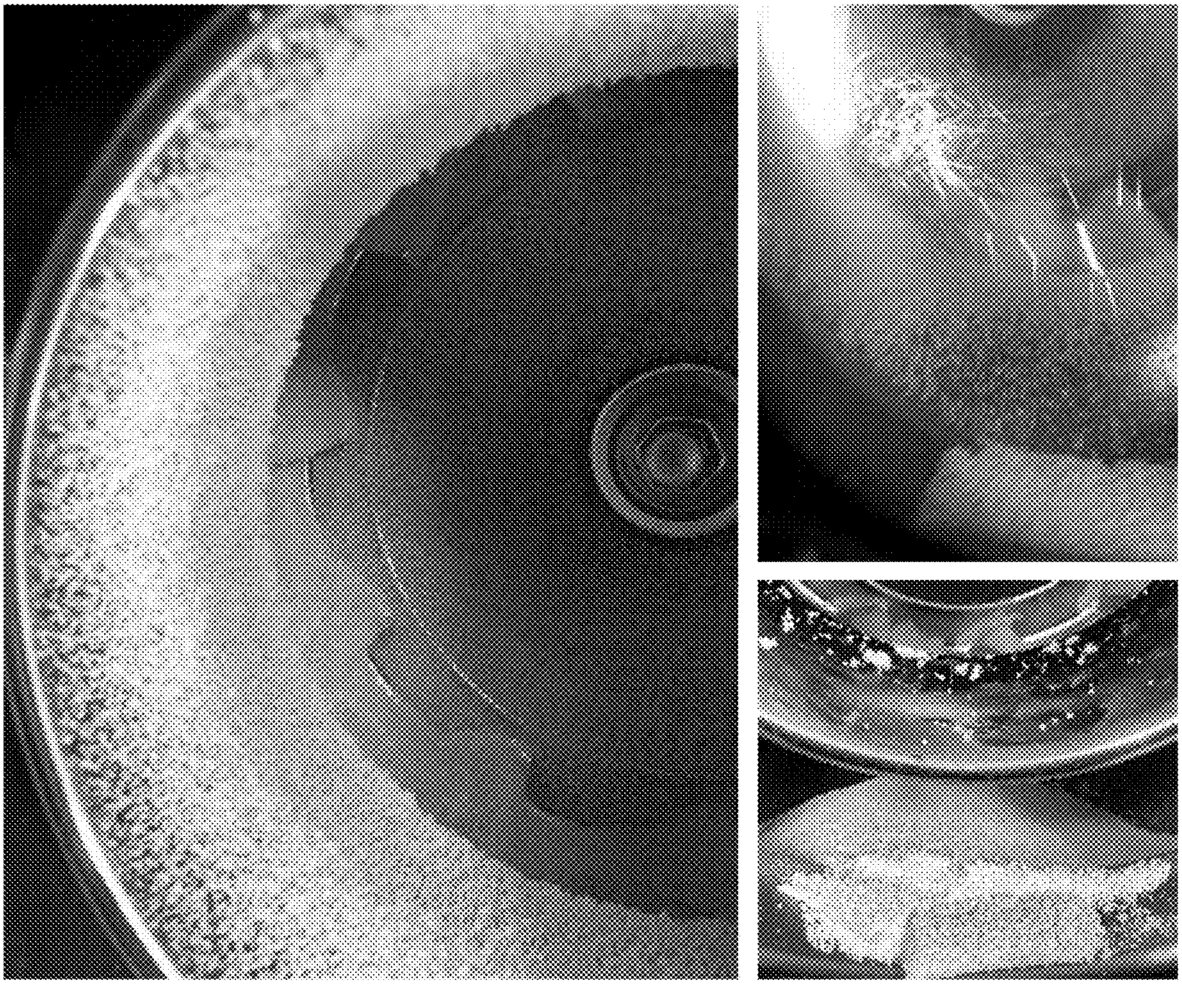
FIG. 5 shows a pan coater configuration in accordance with the methods described herein.

The Pan Coater configuration, as shown in FIG. 5, present concerns, including spraying at lowest setting blows away microspheres, product leaks through holes of the drum, and particles stick to the back and front of the drum where they create a thick film. Potential mitigations include designing a new drum with rubber stoppers and use of a higher density material.

Figure 6:
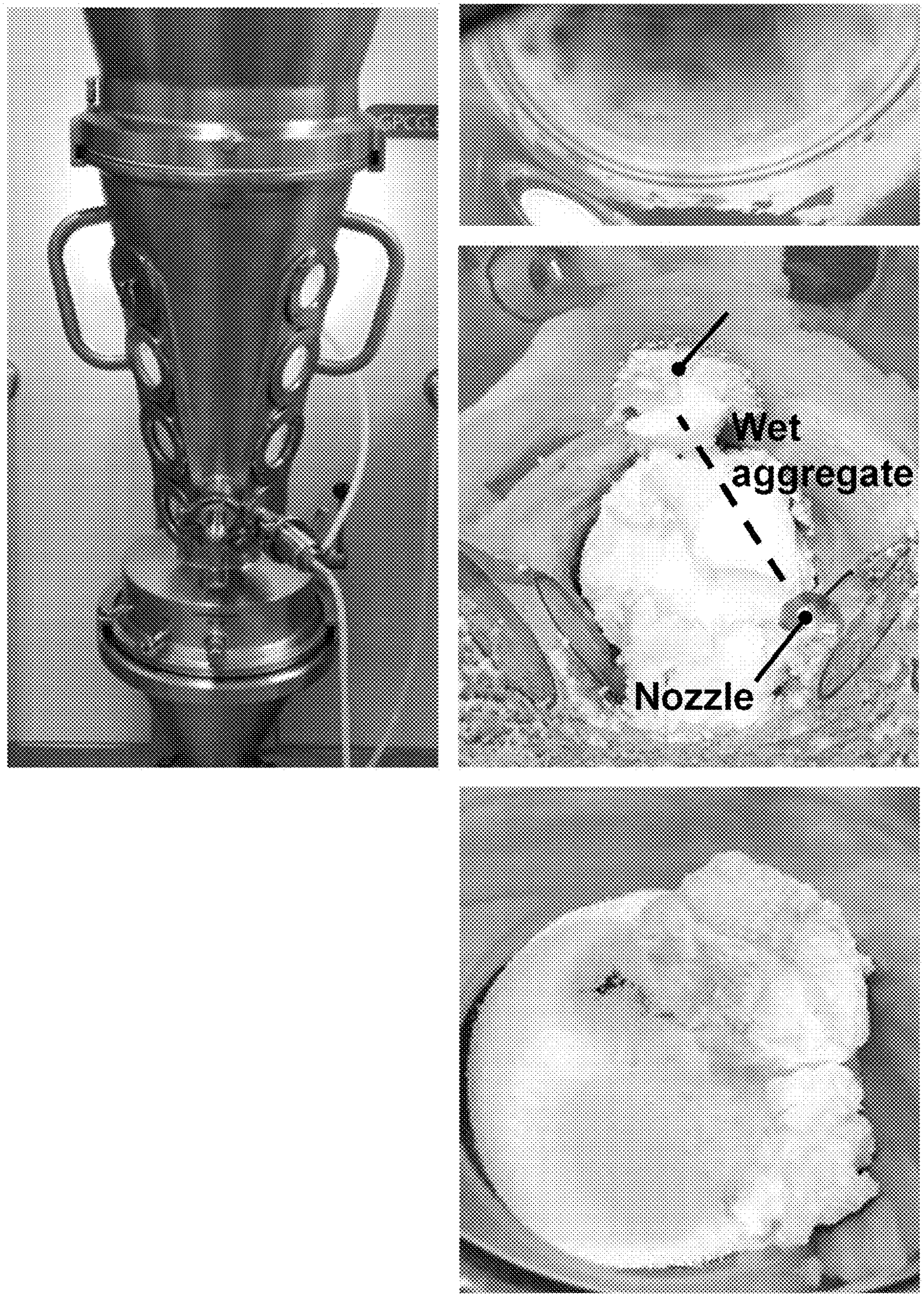
FIG. 6 shows a fluidized bed, tangential spray, configuration in accordance with the methods described herein.

A fluidized bed with Tangential Spray, which is exemplified in FIG. 6 presented various concerns including material that was wet due to spraying into material, about ⅓ material loss due to mechanical stress, wet aggregate where spray hits the wall, and wet microsphere cakes formed. Potential mitigations include increasing the distance between nozzle and drum wall and/or increasing batch size.

Figure 7:
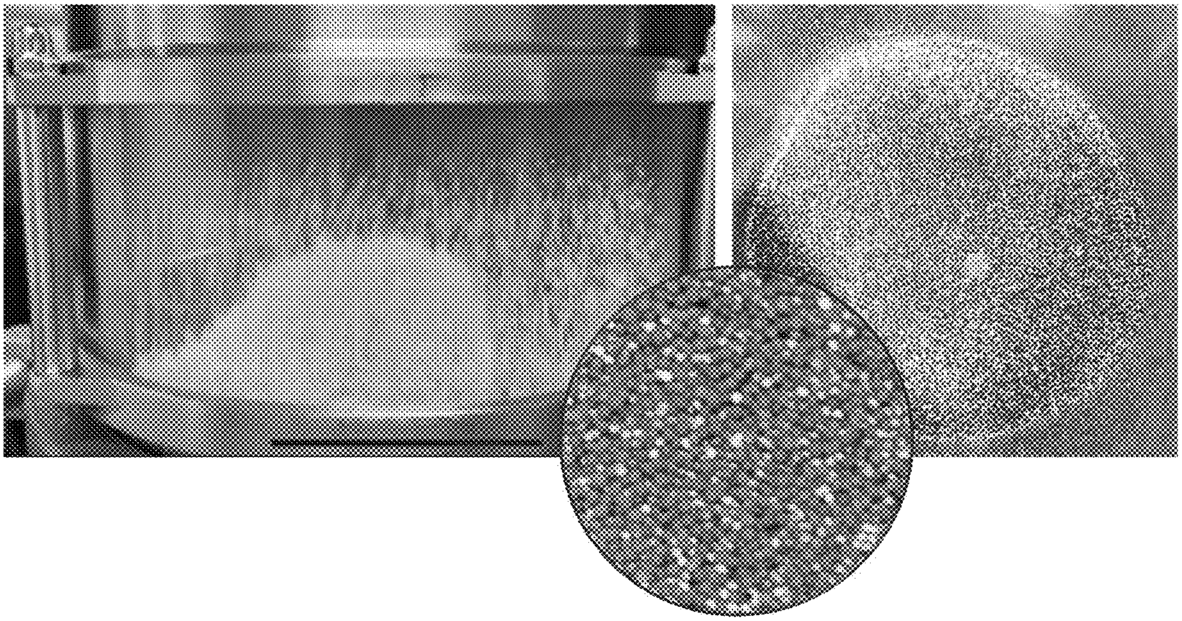
FIG. 7 shows a fluidized bed, bottom spray, configuration in accordance with the methods described herein.

A fluidized bed, bottom spray, configuration, as shown in FIG. 7, presented concerns including poor homogeneity and static build-up. Potential mitigations include use in Wurster configuration to guide the trajectory of microspheres and increase homogeneity. If a bottom spray is used, the Wurster configuration may be preferable.

Figure 8:
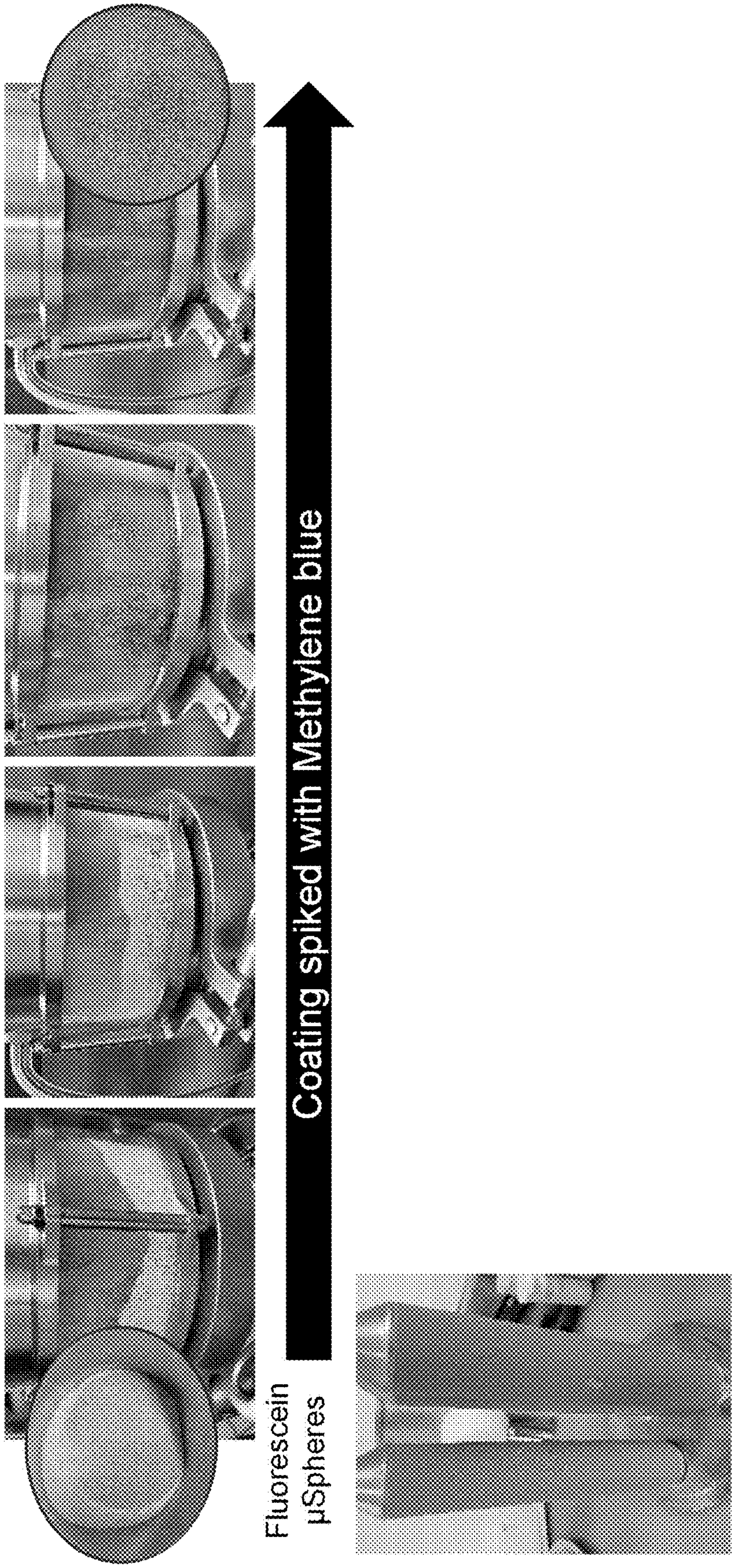
FIG. 8 shows a fluidized bed, top spray, configuration in accordance with the methods described herein.

A fluidized bed, top spray, as shown in FIG. 8, presented concerns such as static and attrition with powder deposition on filter. Potential mitigation for attrition may include, for example, altering core formulation or lower fluidization settings. Potential mitigation for static may include increasing spray rate or increasing water content in coating formulation. The fluidized bed, top spray, appears to be suitable for encapsulating and/or coating the lyophilised microspheres described herein.

Figure 9:
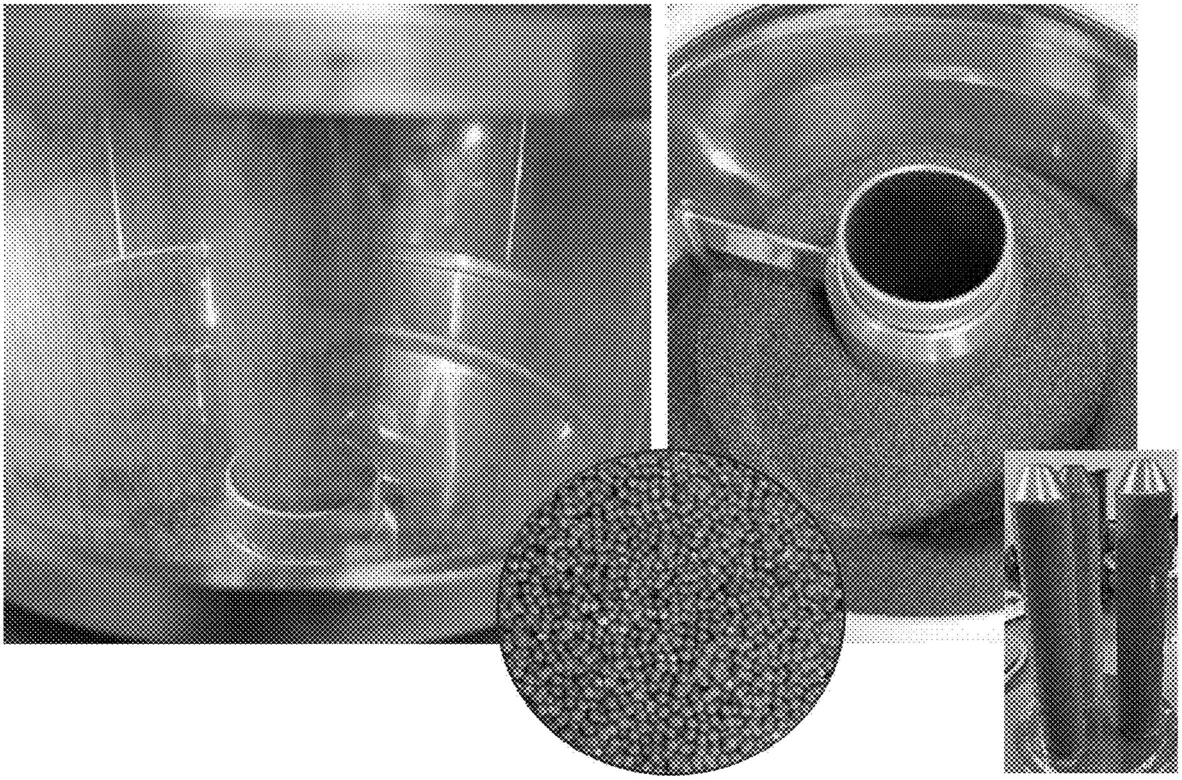
FIG. 9 shows a fluidized bed, Wurster spray, configuration in accordance with the methods described herein.
Figure 10:
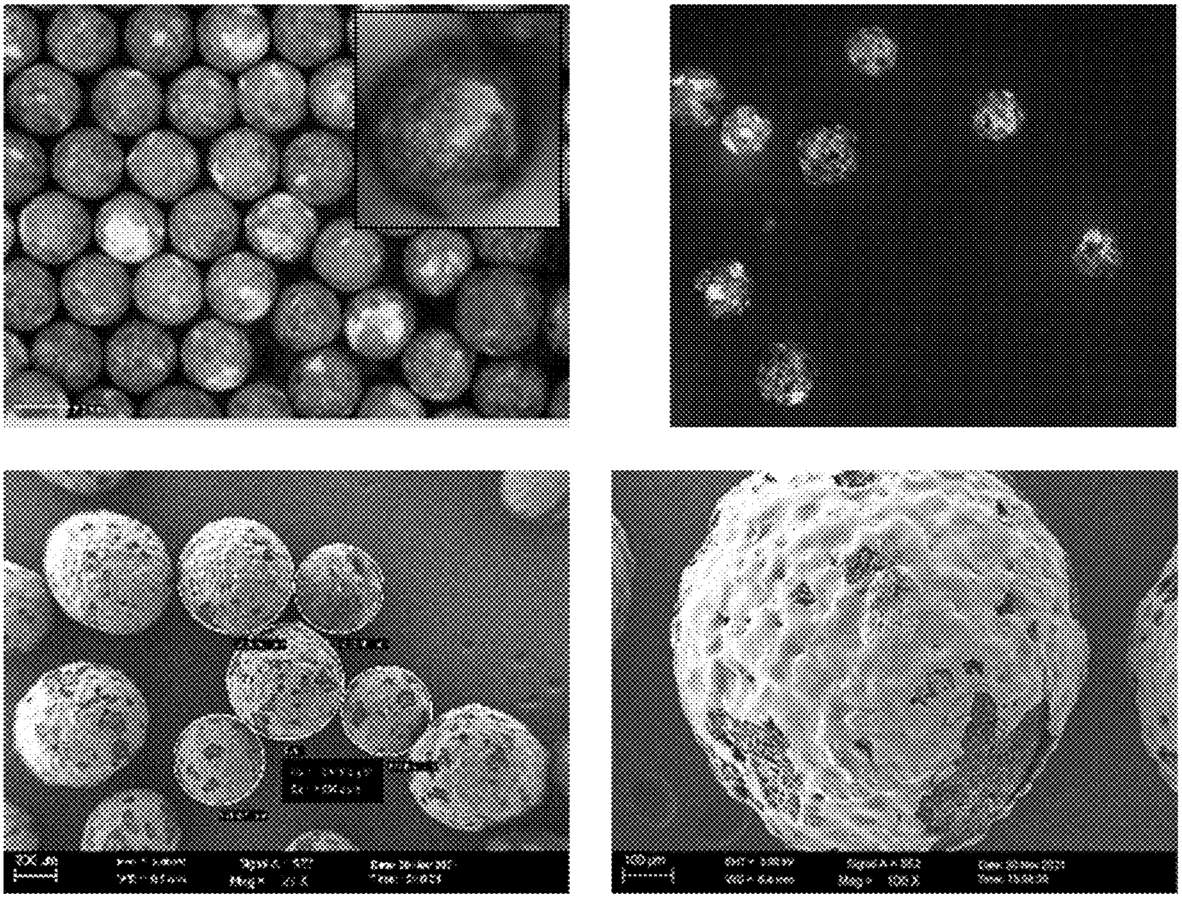
FIG. 10 shows metrology, in particular, optical coating evaluation in accordance with the methods described herein. A good coating may be achieved with Wurster process.
Figure 11:
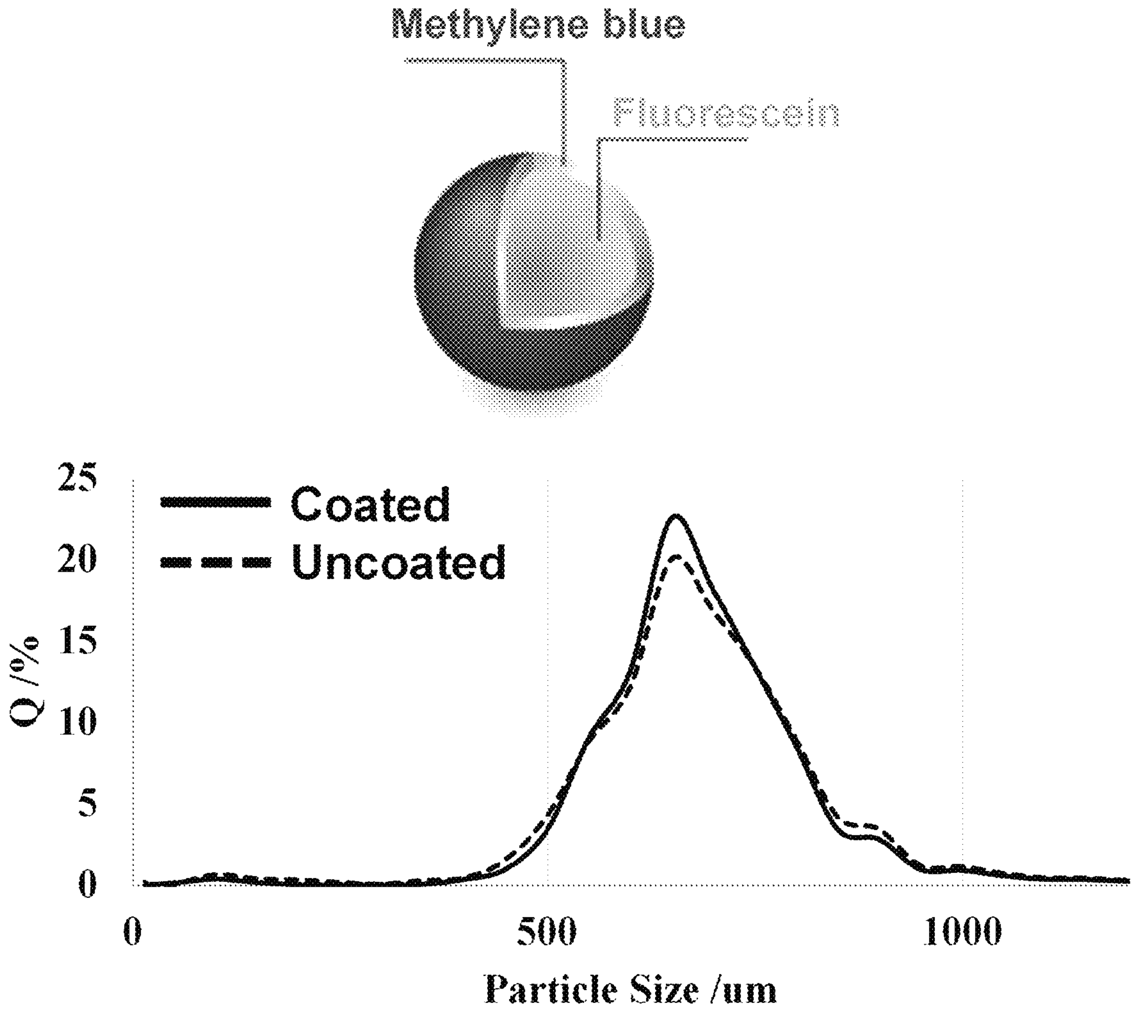
FIG. 11 shows an encapsulated microsphere and particle size results of encapsulated lyophilized microsphere and an uncoated lyophilised microsphere prepared in accordance with the methods described herein.
Figure 12:
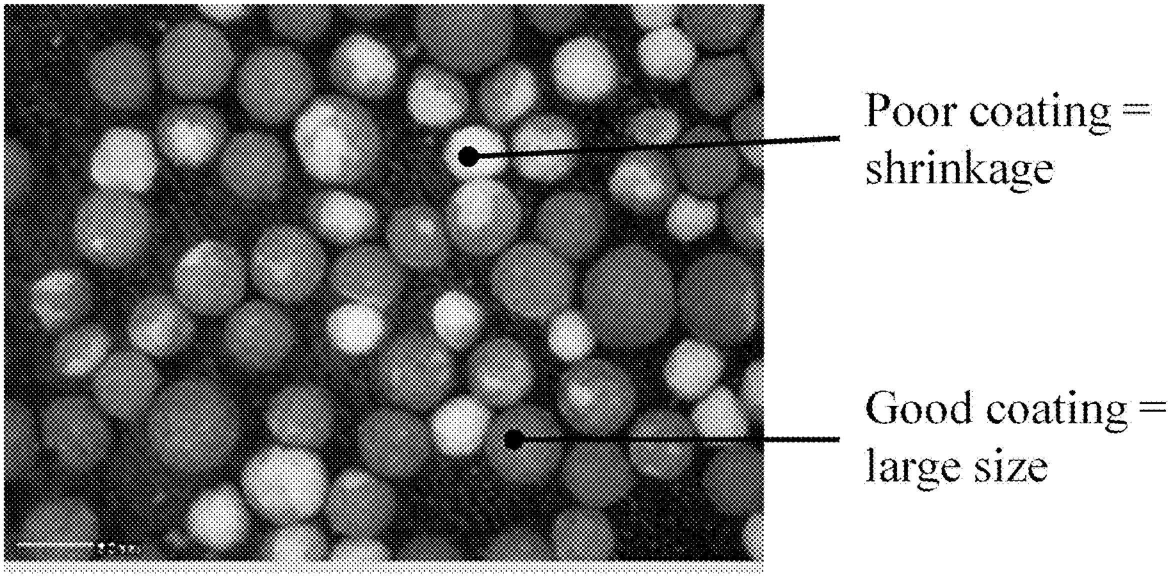
FIG. 12 shows encapsulated microspheres prepared with a bottom spray process.
Figure 13:
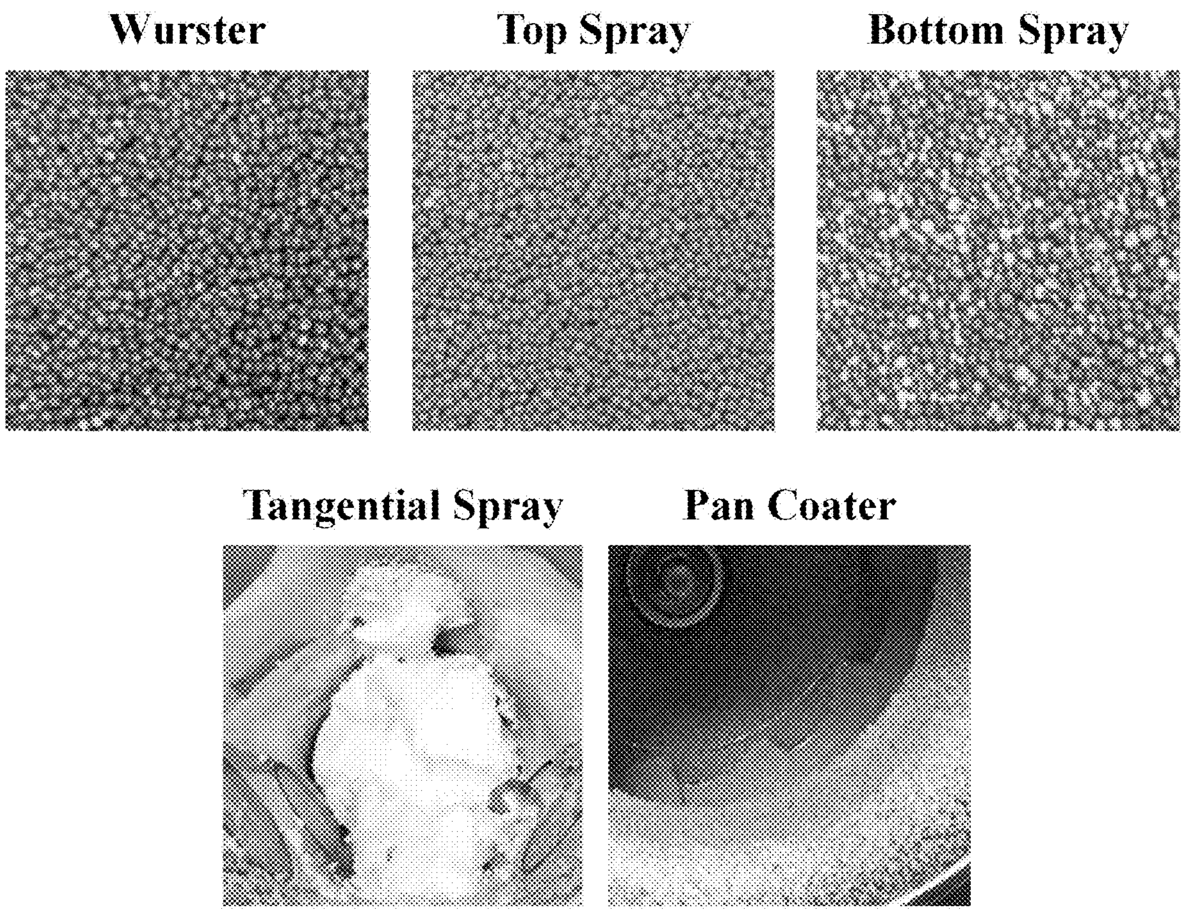
FIG. 13 shows characterization of the results of various methods described herein to encapsulate microspheres.
Figure 14:
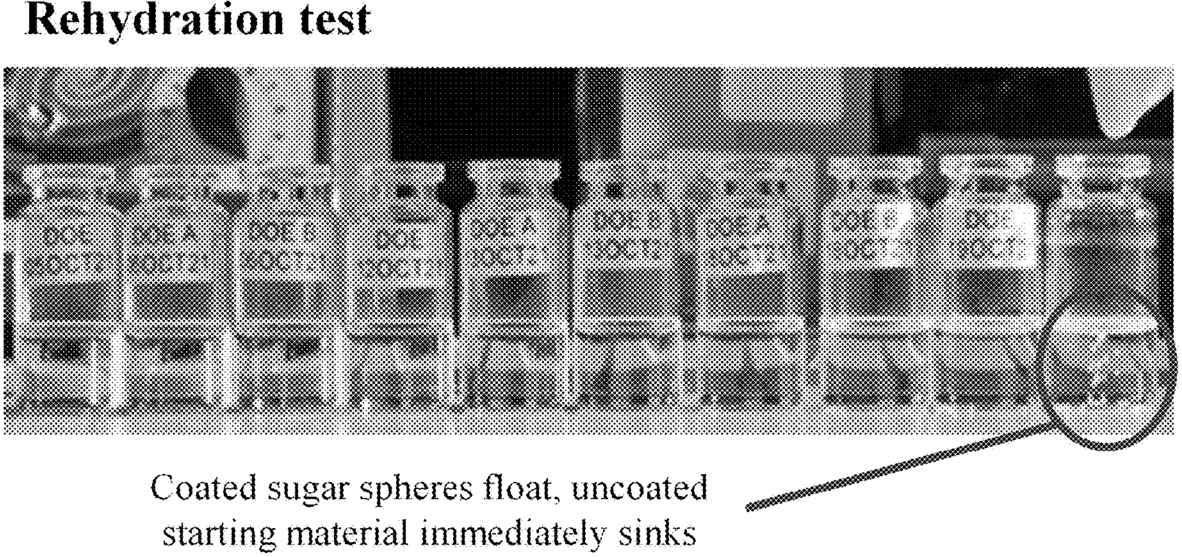
FIG. 14 shows results of a rehydration test. Coated sugar spheres floated; uncoated starting materials immediately sunk.
Figure 15:
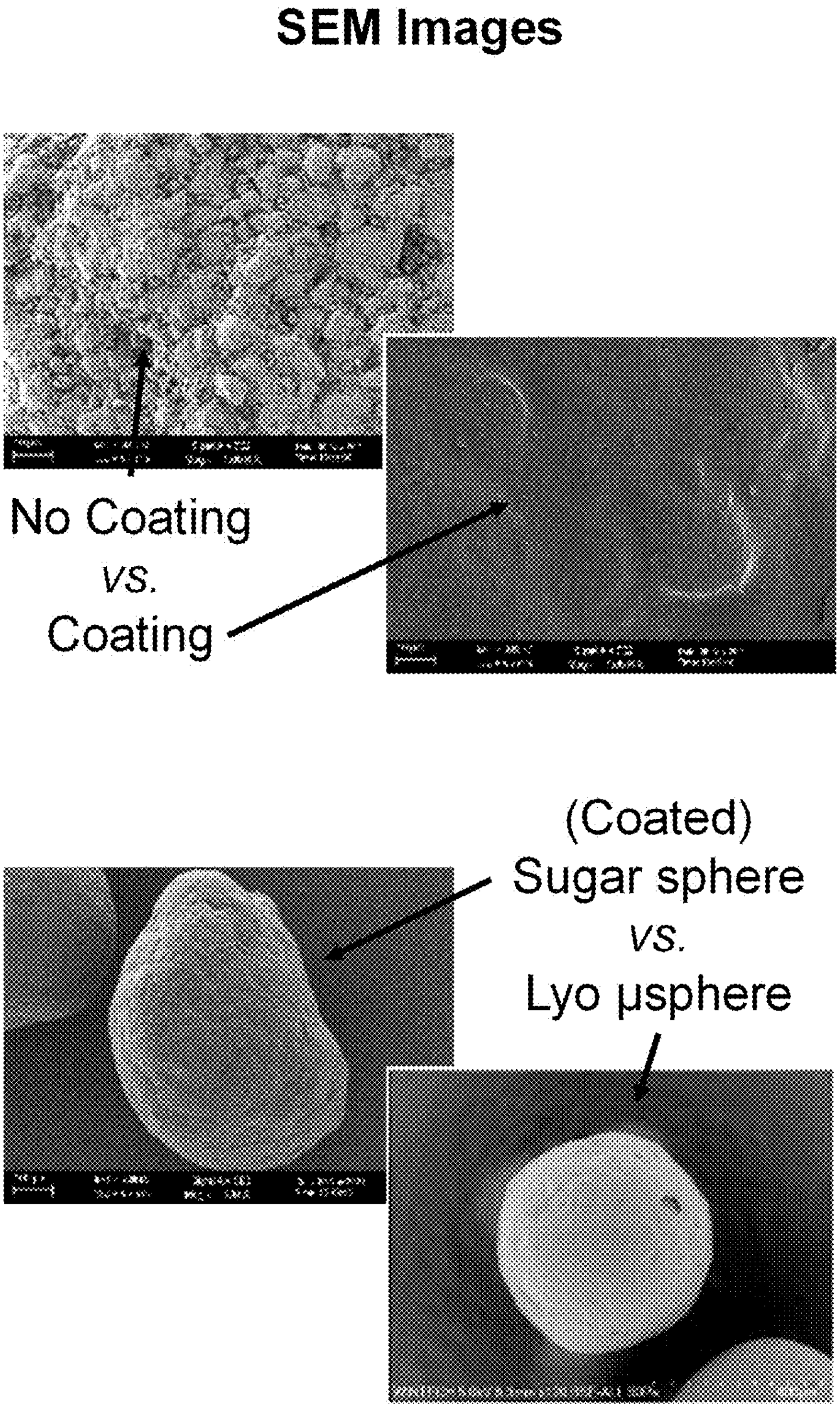
FIG. 15 shows scanning electron microscope (SEM) images of coated and uncoated microspheres.

A fluidized bed, Wurster spray configuration, as shown in FIG. 9, is suitable for encapsulating and/or coating the lyophilised microspheres described herein. While there are concerns including static, excessive spray rate causing aggregation, and attrition with powder deposition on filter, there are various useful mitigations including increasing drying temperature, adjusting spray rate, and changing formulations. A good coating may be achieved with a Wurster process (see FIGS. 10-12, 14, and 15). The results of various methods described herein to encapsulate microspheres are characterized in FIG. 13 and Table 1.

TABLE 1

| | Wurster | Top Spray | Bottom Spray | Tangential Spray | Pan Coater |
|---|---|---|---|---|---|
| Yield | 90-88% | 94% | 67% | 15% | 0% |
| Loss on Drying | 3.41 | 4.11 | 2.89 | 3.90 | — |
| Moisture content (% RH) | 0.64 | 1.49 | 0.30 | 1.60 | — |
| Size distribution (0.5, μm) | 648.34 | 507.26 | 488.35 | 532.21 | — |
| Rehydration | Instant | Instant | Instant | 4 mins | — |
| Foam | Yes, dissipates by 2 min | Yes, dissipates by 1 min | Yes, dissipates by 1 min | No | — |
| Precipitates | No | No | No | Yes | — |

Further results of various methods described herein to encapsulate microspheres are characterized in Tables 2A and 2B.

TABLE 2A

| | Wurster cylinder height (cm) | | Spray rate (g/min) | | |
|---|---|---|---|---|---|
| | 21 | 25 | 2 | 3 | Ctrl |
| Yield (%) | 98.73 | 99.00 | 98.60 | 99.13 | — |
| Rehydration | Floats | Floats | Floats | Floats | Sinks |
| Particle size d10 (μm) | 491.75 | 487.93 | 488.43 | 491.24 | 508.4 |
| Particle size d90 (μm) | 796.45 | 793.42 | 611.46 | 616.99 | 812.5 |
| % RM | 0.57 | 0.56 | 0.55 | 0.58 | 0.85 |

TABLE 2B

| | Atomising airflow (Bar) | | Inlet airflow (L/hr) | | |
|---|---|---|---|---|---|
| | 0.9 | 1.2 | 13.9 | 16.0 | Ctrl |
| Yield (%) | 98.73 | 99.01 | 99.07 | 98.66 | — |
| Rehydration | Floats | Floats | Floats | Floats | Sinks |
| Particle size d10 (μm) | 490.71 | 488.96 | 491.25 | 488.42 | 508.4 |
| Particle size d90 (μm) | 798.26 | 791.60 | 800.06 | 789.81 | 812.5 |
| % RM | 0.56 | 0.57 | 0.58 | 0.54 | 0.85 |

Figure 16:
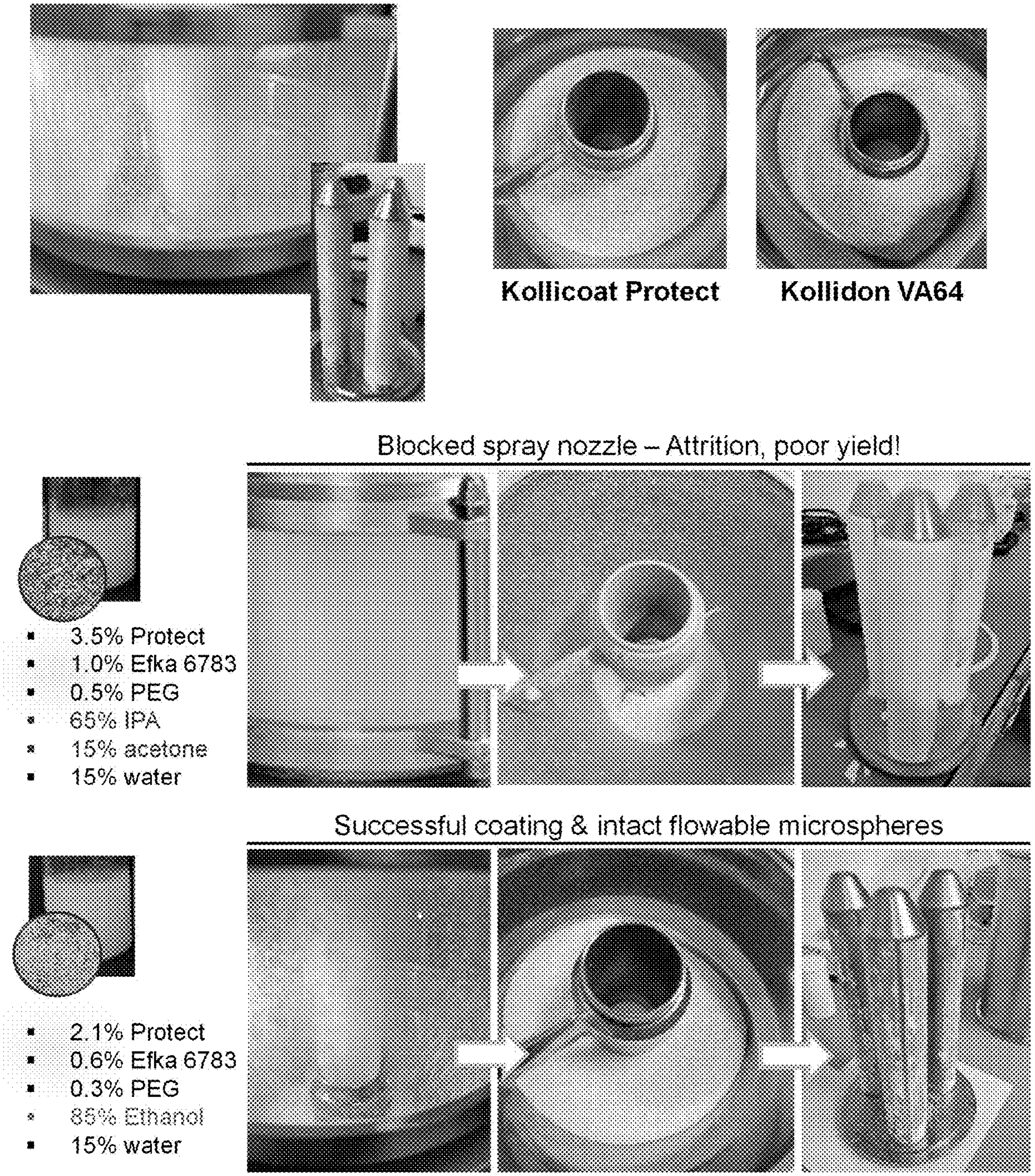
FIG. 16 depicts results of spraying SBS-relevant microspheres in Wurster configuration.
Figure 17:
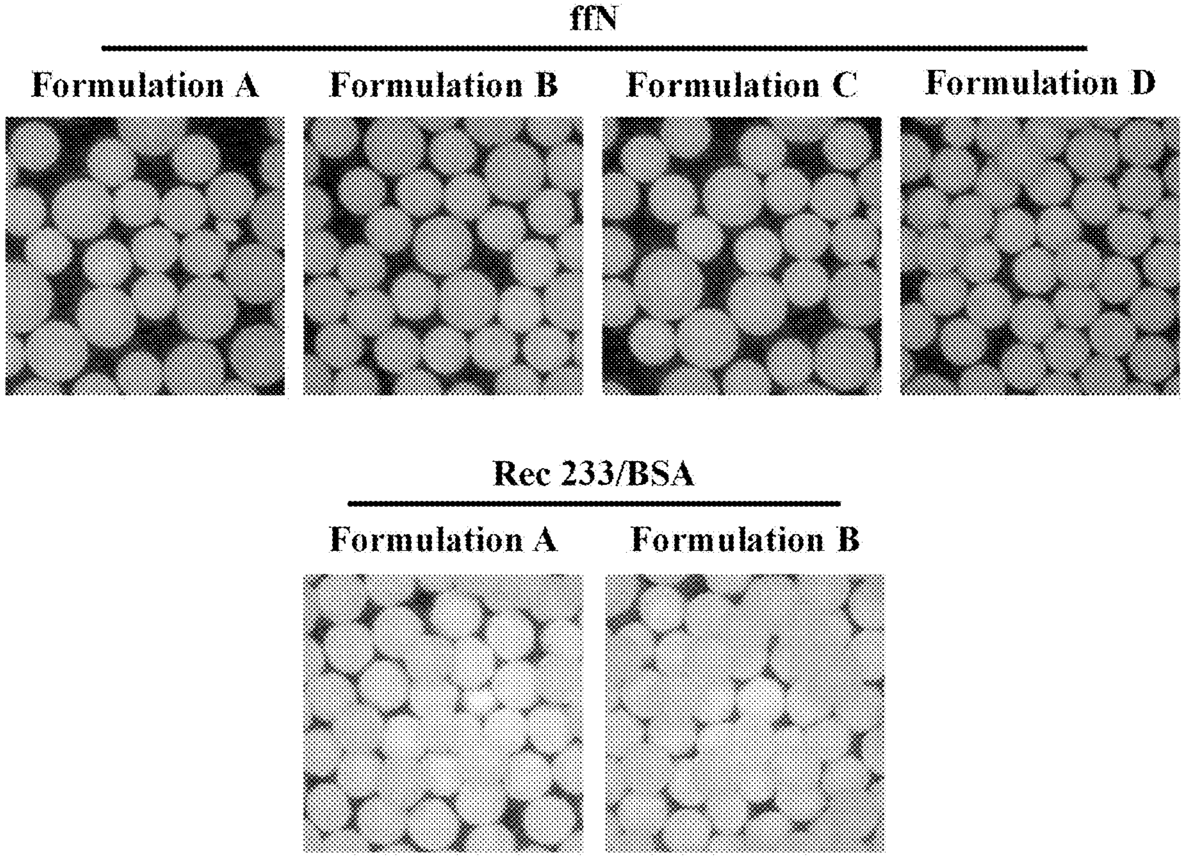
FIG. 17 demonstrates physical data for various encapsulated microspheres that were encapsulated using the methods described herein.
Figure 18A:
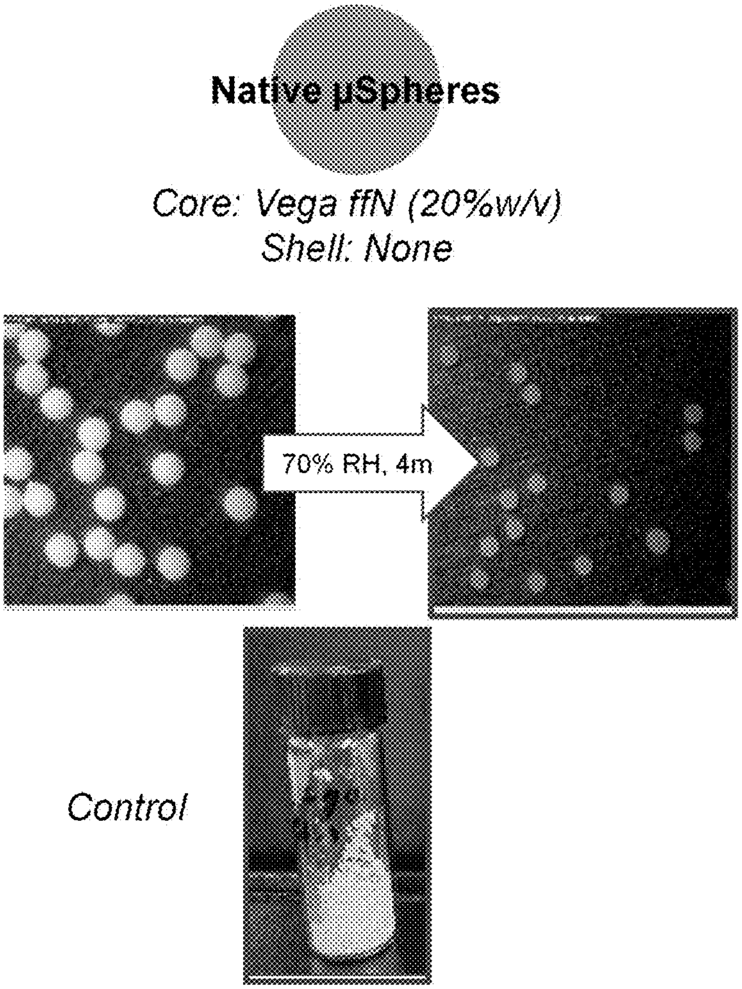
FIGS. 18A-18C shows that shell encapsulation using the methods described herein improves moisture barrier and mitigates static. Matrix encapsulation is often for static mitigation, whereas core shells often address both.
Figure 18B:
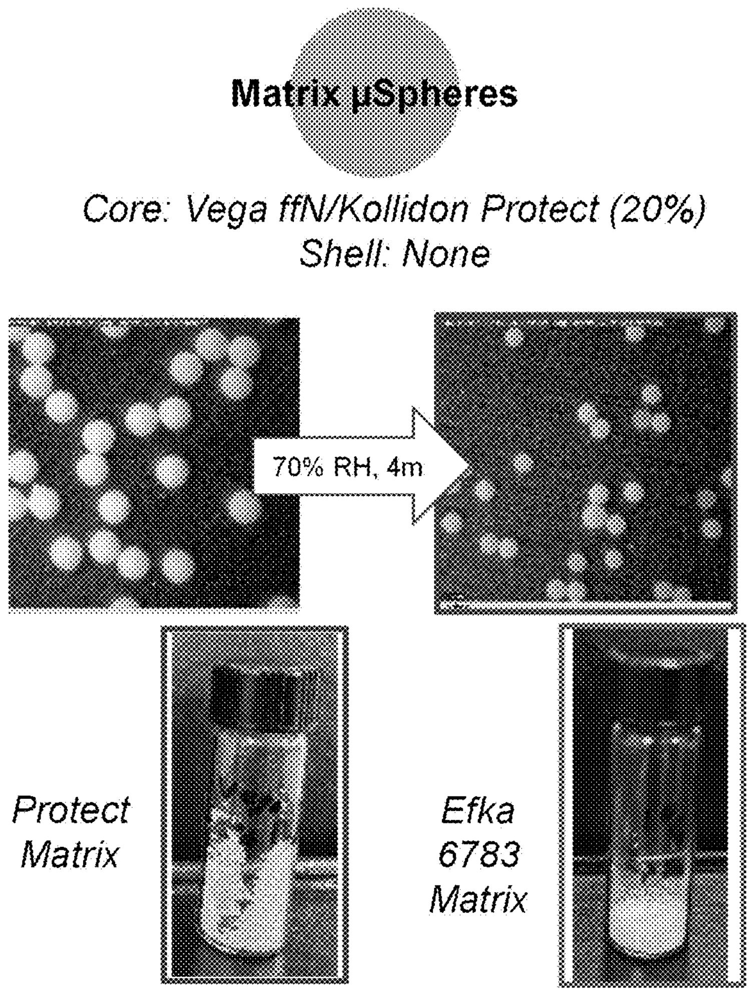
Figure 18C:
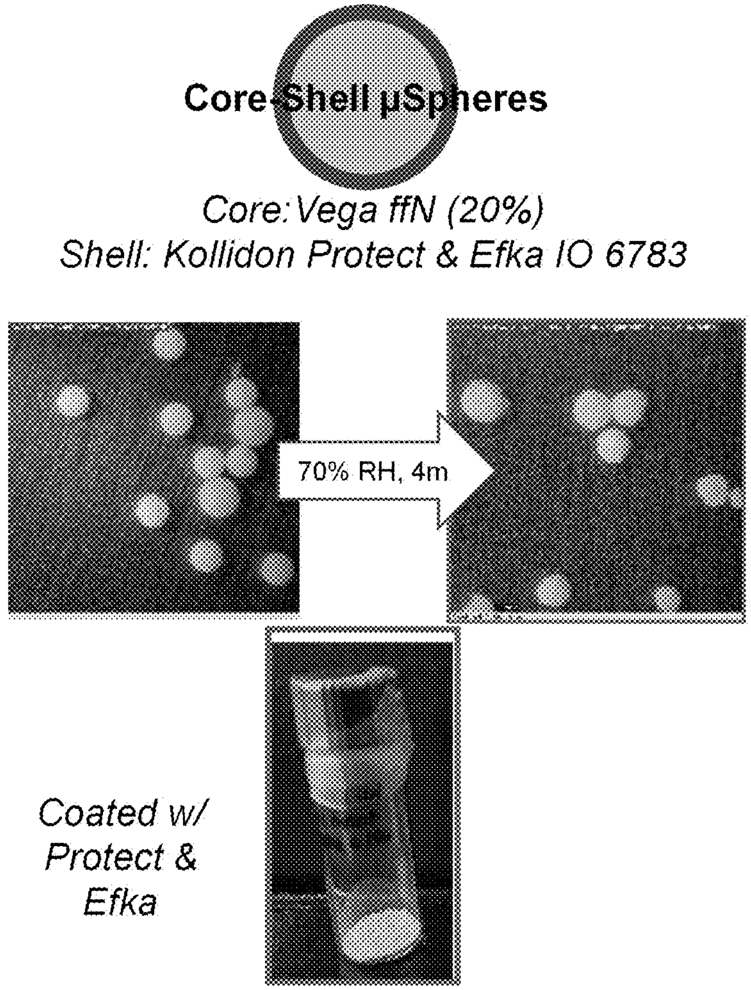
Figure 19:
FIG. 19 show results of freund-vector trial.

Results of spraying SBS-relevant microspheres in Wurster configuration are further shown in FIG. 16. Physical data for various encapsulated microspheres that were encapsulated using the methods described herein are described in FIG. 17 and Tables 3A and 3B. Shell encapsulation using the methods described herein improves moisture barrier and mitigates static. See FIGS. 18A-18C. Matrix encapsulation is limited to static mitigation, whereas core shells address both. Results of freund-vector trial are shown in FIG. 19 and Table 4.

TABLE 3A

| | ffN | | | |
|---|---|---|---|---|
| Coating | Formulation A | Formulation B | Formulation C | Formulation D |
| Yield (%) | 95 | 80 | 100 | 100 |
| Loss on drying | 3.77 | 3.91 | 5.99 | 5.12 |
| Res. Moisture (% RH) | 0.90 | 0.42 | 0.51 | 0.35 |

TABLE 3A-continued

| | ffN | | | |
|---|---|---|---|---|
| Coating | Formulation A | Formulation B | Formulation C | Formulation D |
| Foam | Foam, dissipates by 1 mins | Foam, dissipates by 3.5 mins | Foam, dissipates by 1.5 mins | Foam, dissipates by 3 mins |
| Precipitates | No | No | No | No |
| Size distribution (0.5, μm) | 414.6 | 392.5 | 268.2 | 367.9 |

TABLE 3B

| | Recombinase/Bovine Serum Albumin (BSA) | |
|---|---|---|
| Coating | Formulation A | Formulation C |
| Yield (%) | 94 | 88 |
| Loss on drying | 2.76 | 3.03 |
| Res. Moisture (% RH) | 0.72 | 0.34 |
| Rehydration | Instant | Instant |
| Foam | Foam, dissipates by 30 seconds | No foam |
| Precipitates | No | dissolves <30 s |
| Size distribution (0.5, μm) | 378.6 | 362.5 |

TABLE 4

| | Run 1 | Run 2 | Run 3 | Run 4 |
|---|---|---|---|---|
| Core microspheres | Fluorescein | ffN | ffN | ffN |
| Technique | Wurster | Wurster | Top Spray | Wurster |
| Coating formulation | A | A | A | C |
| Batch size (g) | 30 | 50 | 35 | 35 |
| Run time (min) | 255 | 115.4 | 125 | 297 |
| Failure mode | High attrition during preheat | Poor fluidization after 30 min, external agitation required | Coating completed (less attrition), but agglomeration | High attrition after 60 min having a detrimental impact on fluidization |
| Loss on Drying (%) | 5.15 | 6.29 | 6.25 | 2.78 |
| Particle size (D90, μm) | 622 | 423 | 2548 | 427 |

Figure 21A:
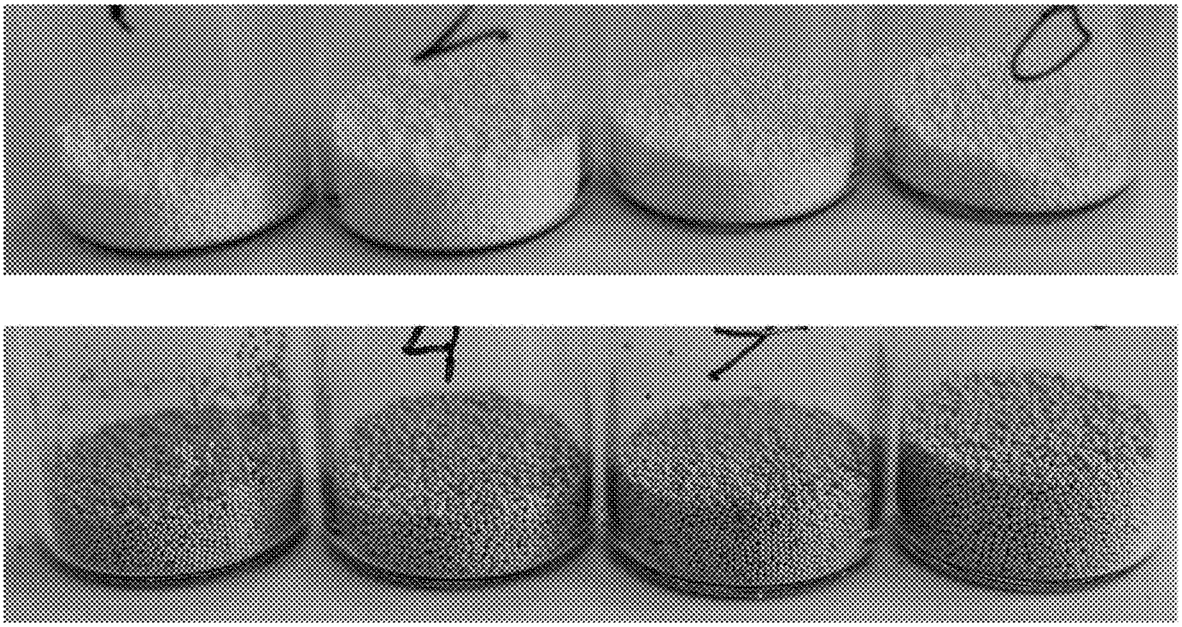
FIGS. 21A and 21B show exemplary formulations of encapsulated microspheres prepared using the methods described herein.
Figure 21B:
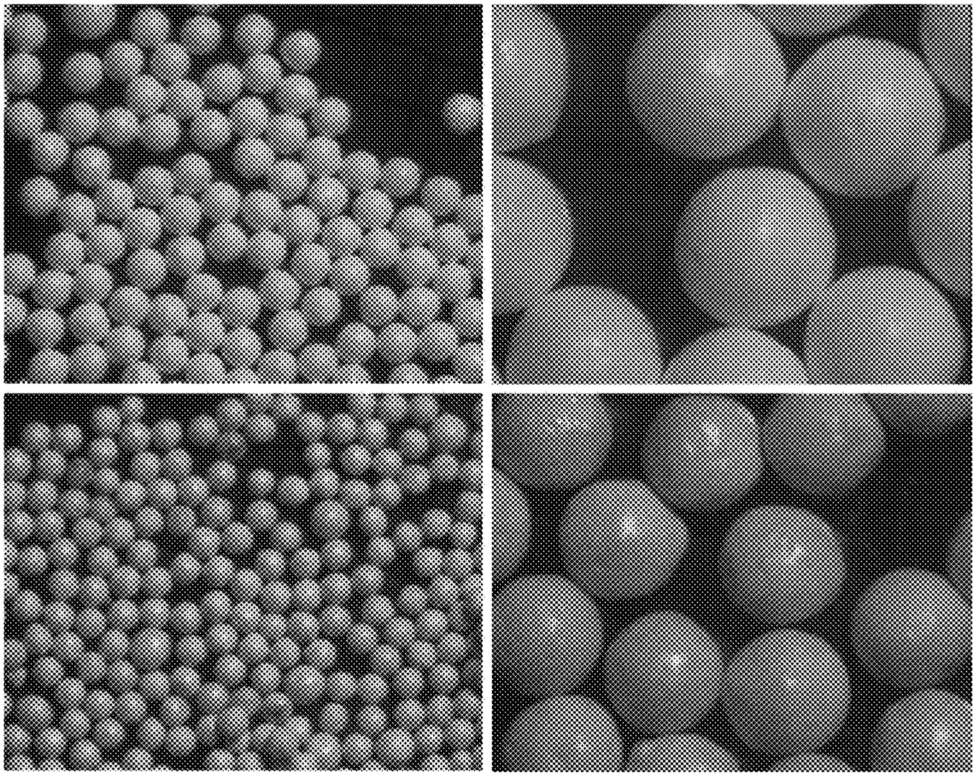
Figure 22:
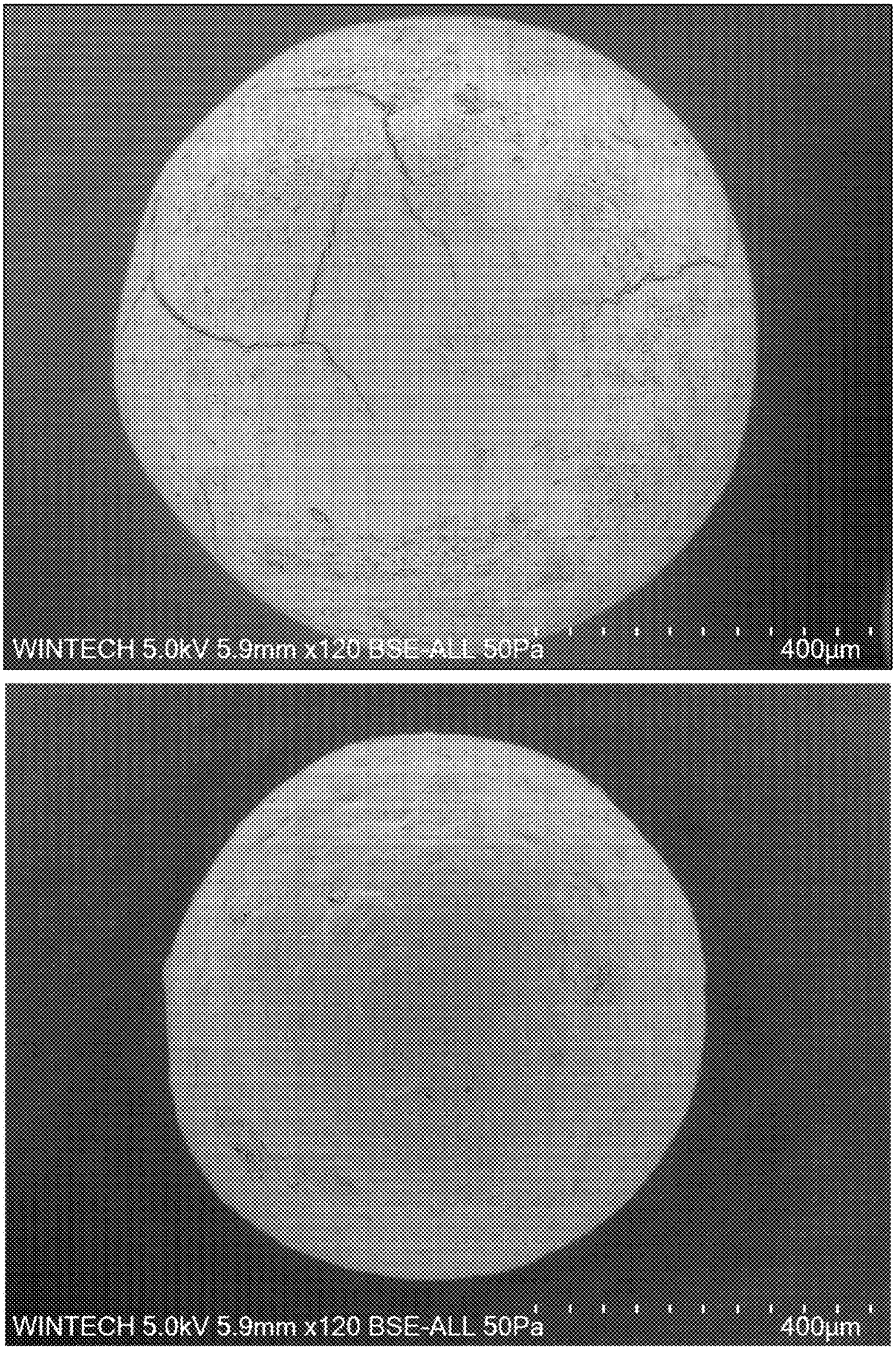
FIG. 22 shows images of encapsulated microspheres that were prepared in accordance with the methods described herein.
Figure 23:
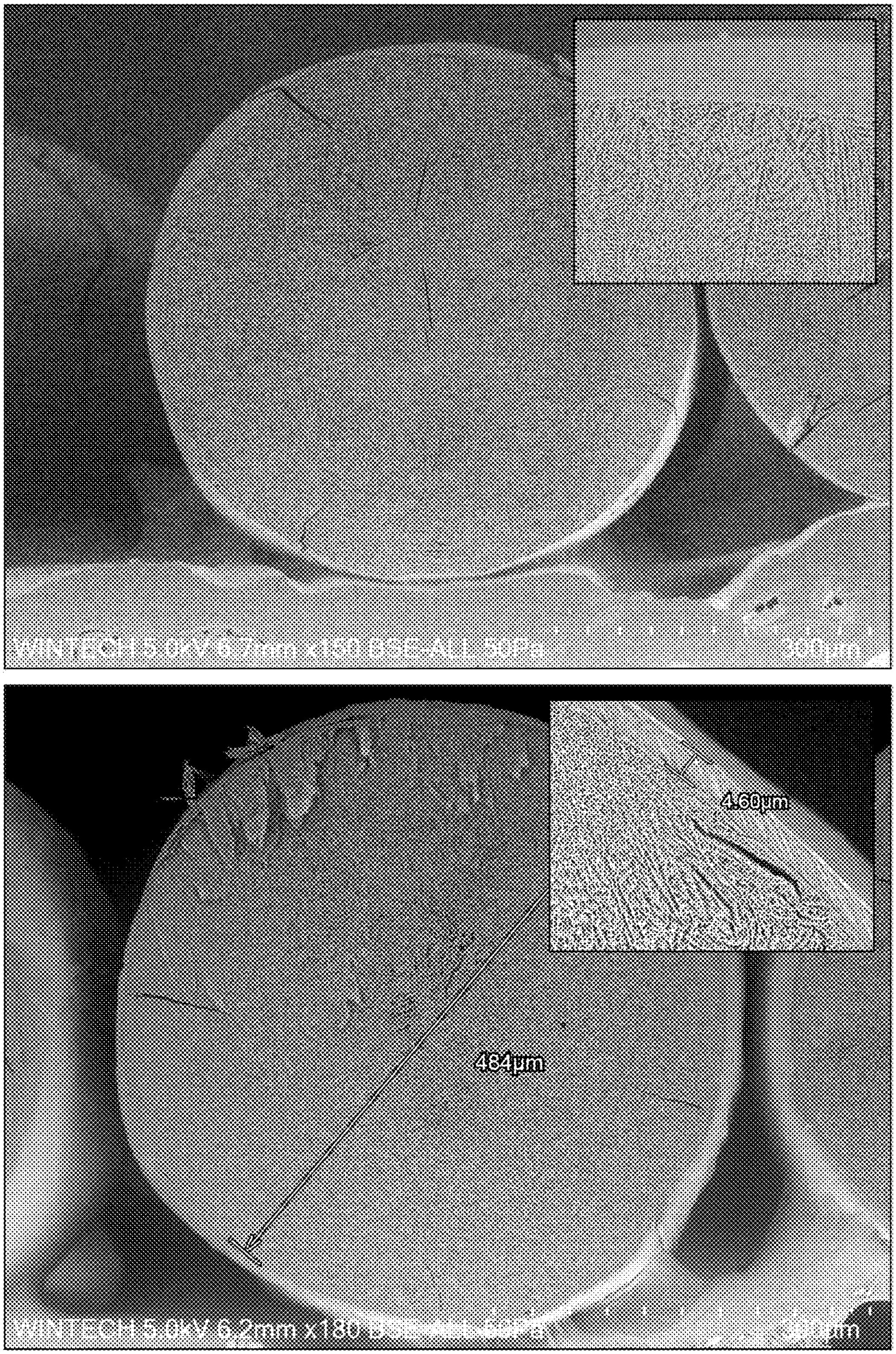
FIG. 23 shows images of encapsulated microspheres that were prepared in accordance with the methods described herein.
Figure 24:
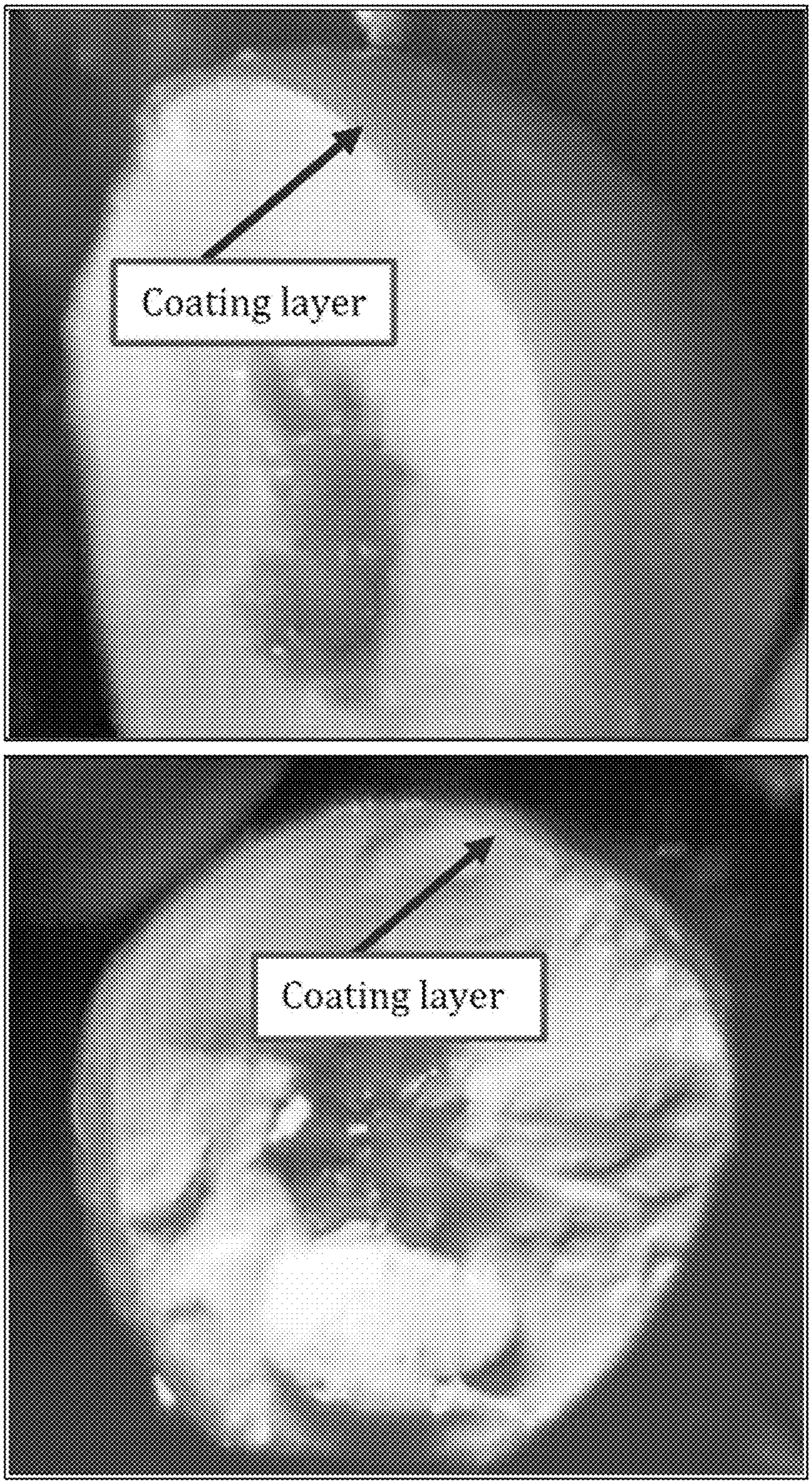
FIG. 24 depicts images of cross-sections of coated particles encapsulated using the methods described herein. Incomplete drying was found, but coating was clearly visible and in a thin layer.

Exemplary formulations of encapsulated microspheres prepared using the methods described herein are shown in FIGS. 21A and 21B. Images of encapsulated microspheres that were prepared in accordance with the methods described herein are shown in FIGS. 22-24. FIG. 21A shows microspheres of two different cores (yellow, on top, and blue, on bottom) of two different sizes for each compared before and after fluidization showing no detrimental impact on the integrity of the microspheres. FIGS. 21B and 22 show homogeneous coating around the microspheres coated in accordance with aspects of the present disclosure.

FIG. 23 shows a cross sectional SEM image of a 5 um coating of a microsphere, coated in accordance with aspects of the present disclosure, without detrimental impact on the nanoscopic architecture of the microsphere. FIG. 24 is a cross-sectional image showing the coating layer around microspheres.

Figure 25A:
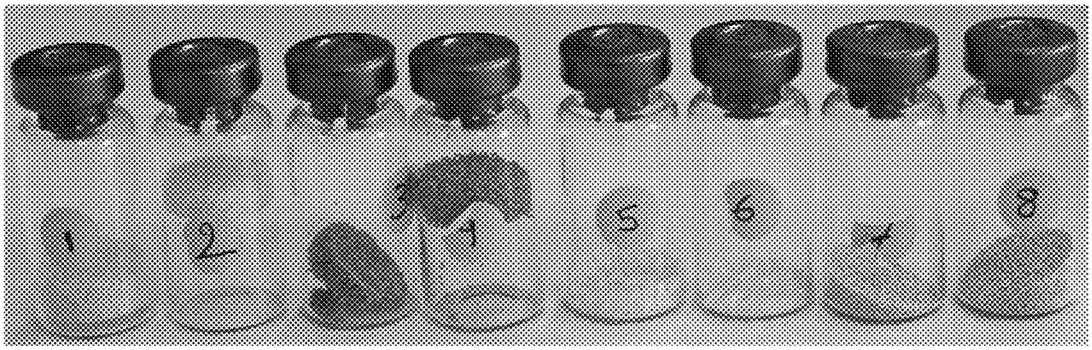
FIGS. 25A and 25B show residual moisture measurements.
Figure 25B:
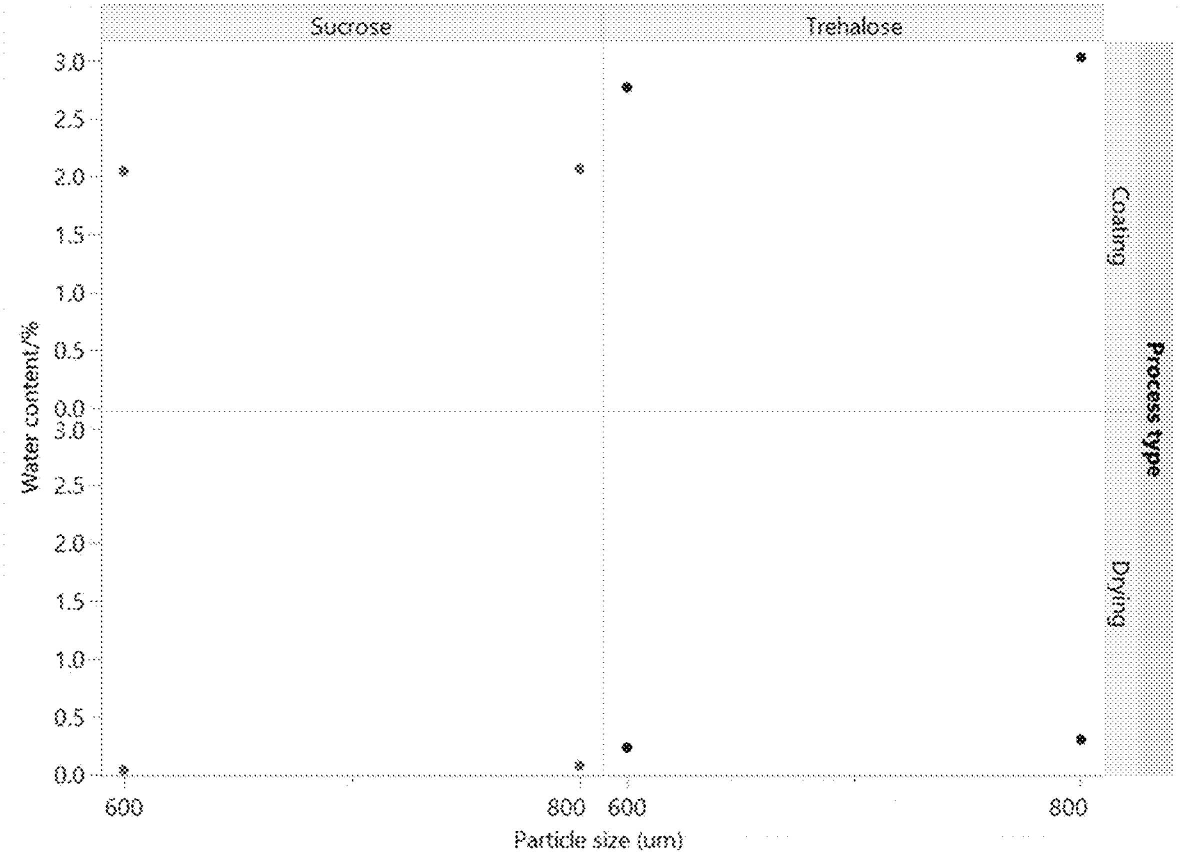

Residual moisture measurements of encapsulated microspheres prepared in accordance with the methods described herein are shown and described in FIGS. 25A, 25B, and Table 5. FIGS. 25A and Table 5 show microspheres post exposure to high temperature where shells have melted and created cakes.

TABLE 5

| | Uncoated | Coated |
|---|---|---|
| 600 μm, Tre/Sucr FL | 5 | 2 |
| 800 μm, Sucr/FL | 6 | 1 |
| 600 μm, Tre/Meth BL | 7 | 3 |
| 800 μm, Tre/Meth BL | 8 | 4 |

Figure 26:
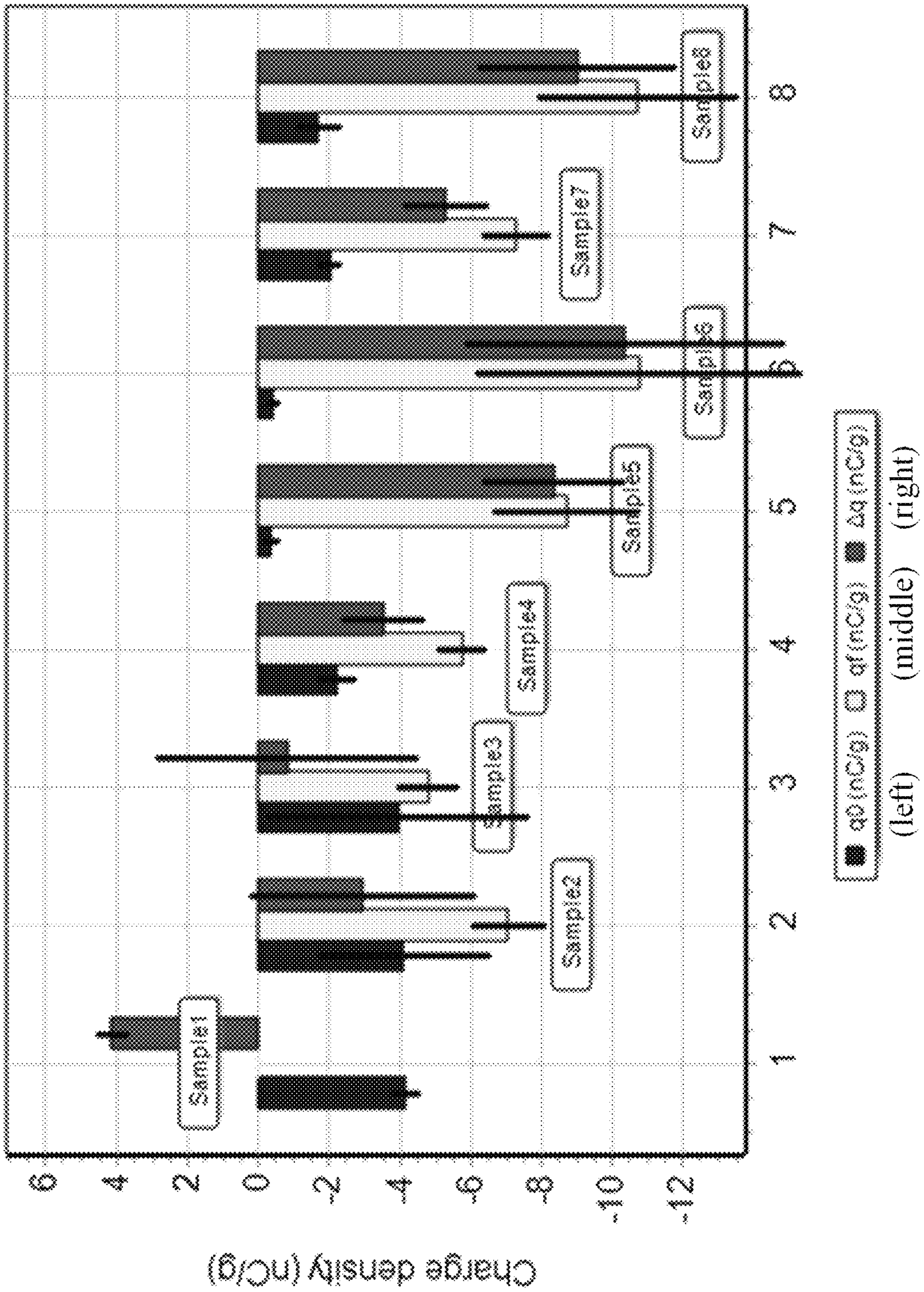
FIG. 26 shows charge density of encapsulated microspheres prepared in accordance with the methods described herein.
Figure 27A:
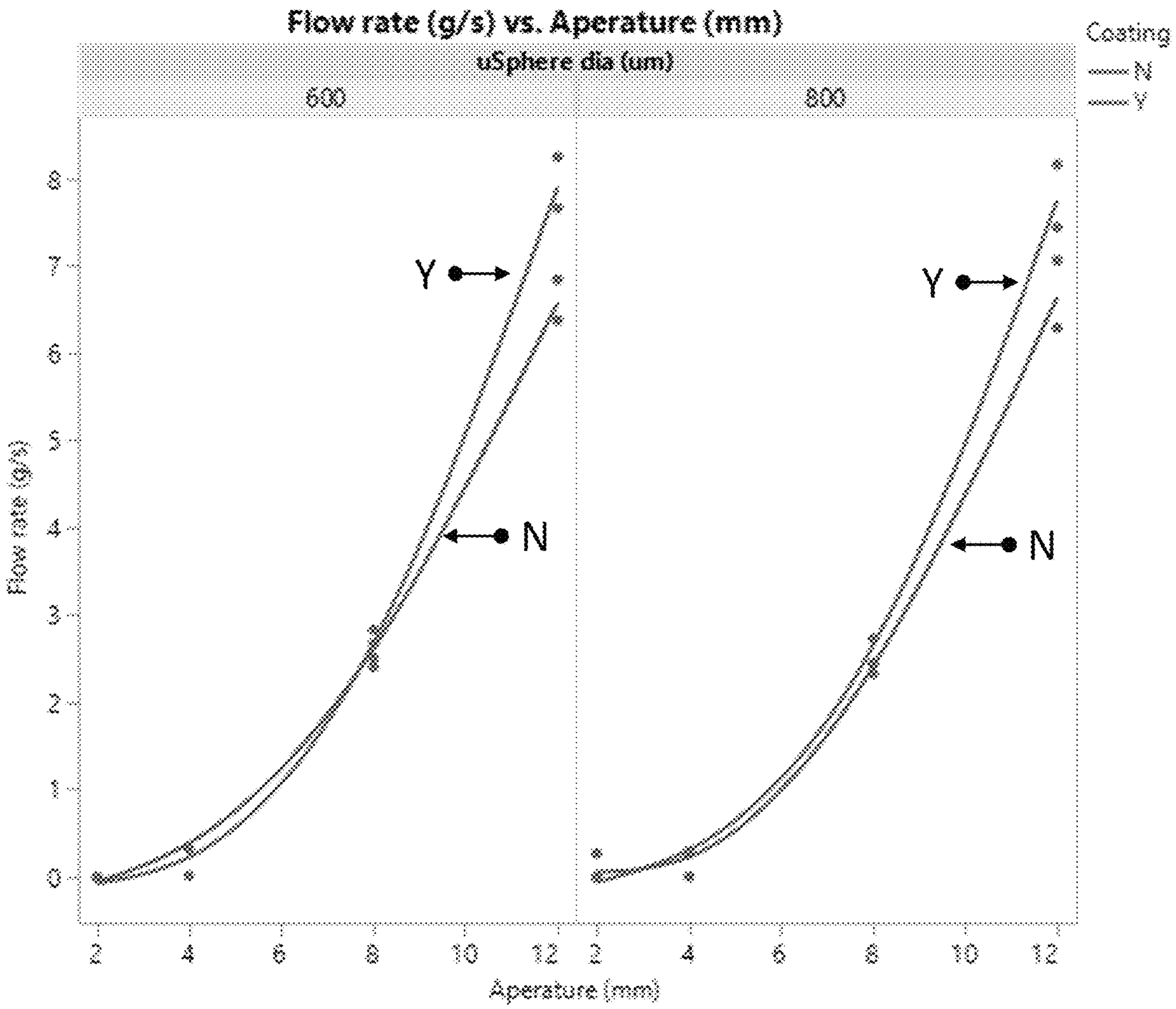
FIGS. 27A and 27B show flowability of microspheres that are encapsulated using the methods described herein is improved over uncoated microspheres.
Figure 27B:
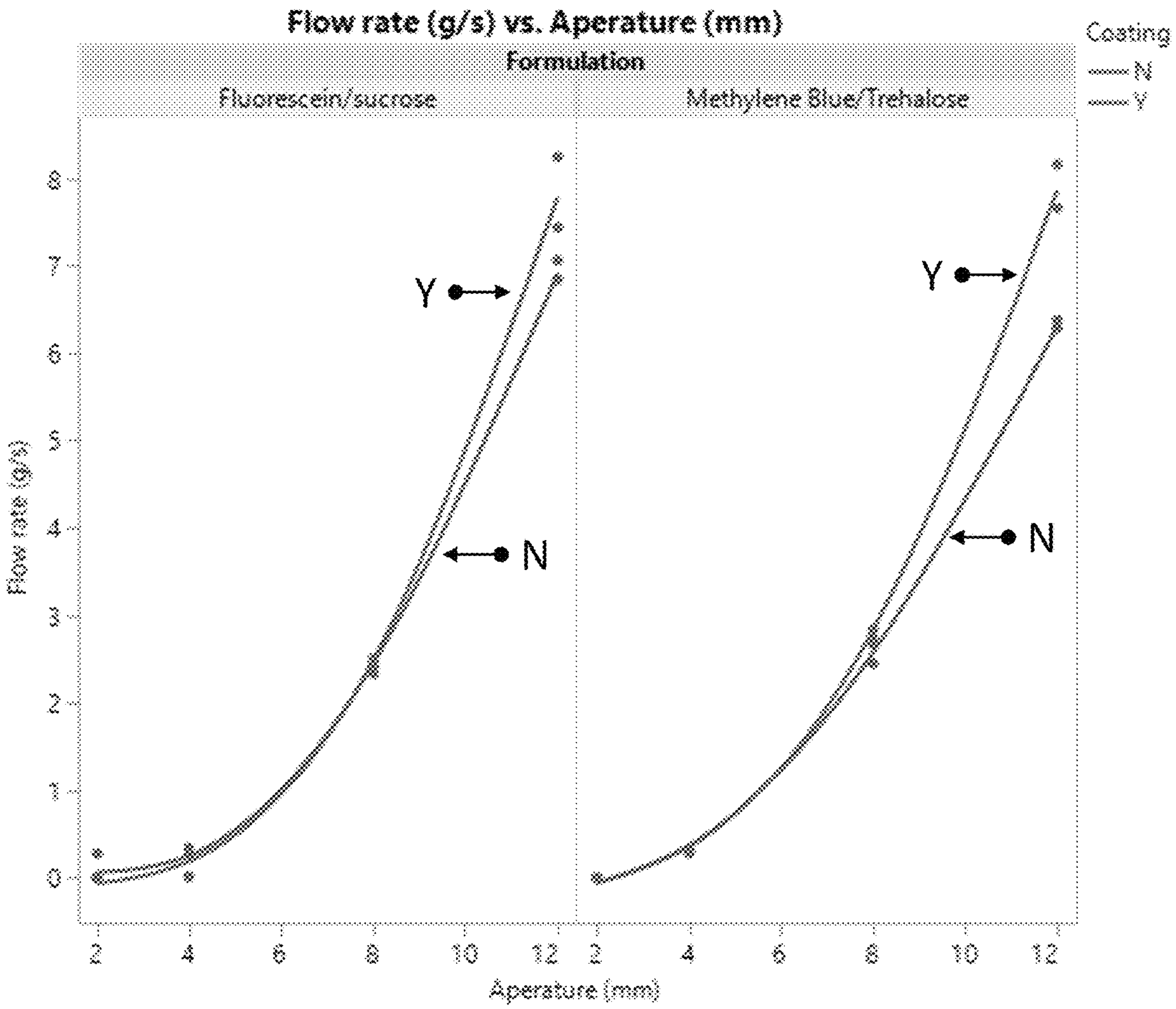

FIG. 25B shows results of a Karl Fischer titration showing that through the process used an increased exposure to humidity occurred which led to an increased percent relative humidity post fluidization. FIG. 26 is a bar graph showing charge densities of coated (Samples 1-4) and uncoated (sampled 5-8) microspheres. Far left bar shows initial charge (q0 (nC/g)), the middle bar shows final charge (qf (nC/g), and the right bar shows the change in charge (Δq (Cn/g)). The smaller magnitude of Δq for coated samples 1-4 reflects their lower tribocharging affinity compared to the uncoated control samples 5-8. FIGS. 27A and 27B illustrate that flowability of microspheres that are encapsulated in accordance with aspects of the present disclosure is favorably increased compared to uncoated microspheres, due to coated microspheres' lower tribocharging affinity.

Figure 28A:
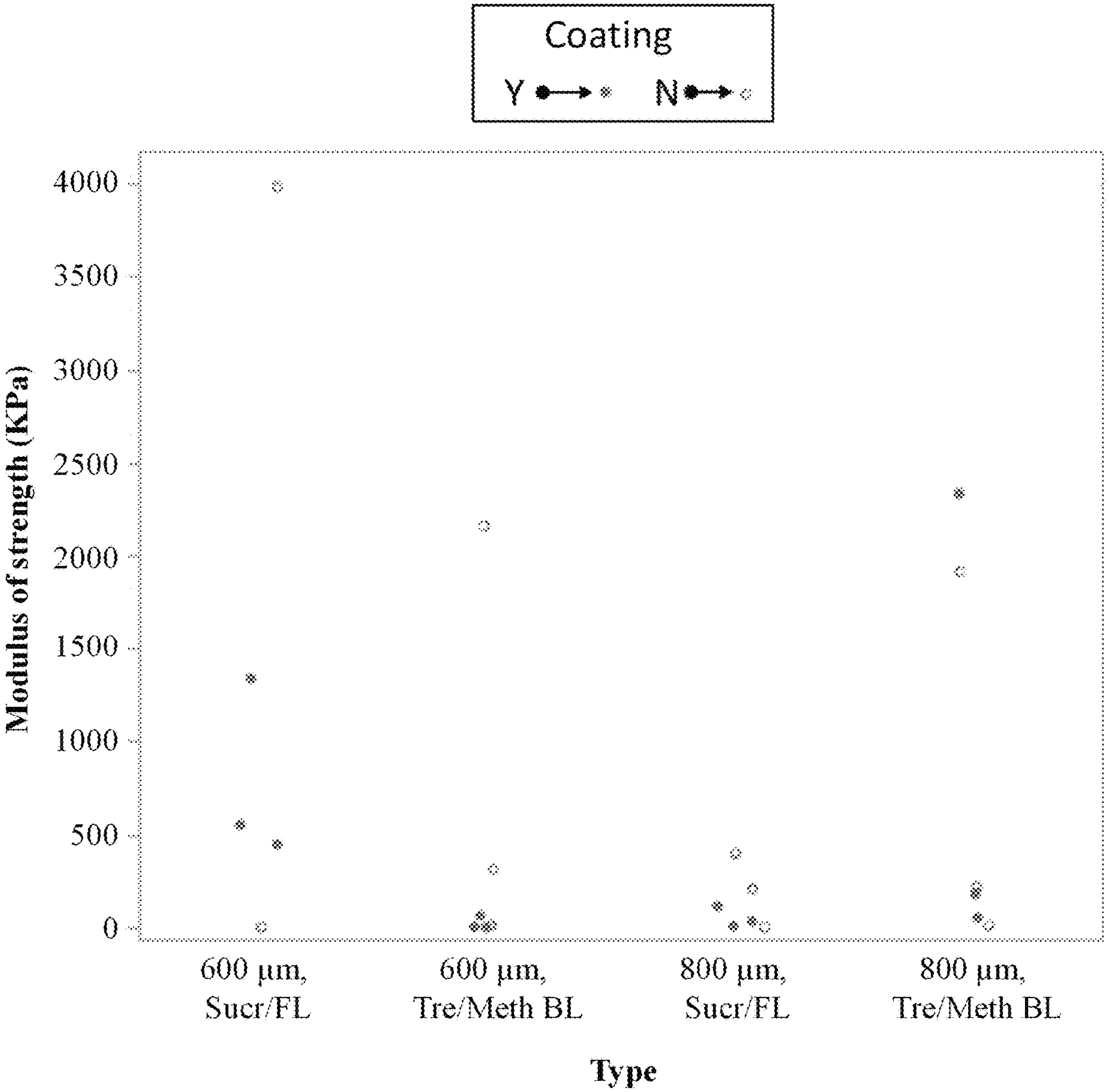
FIG. 28A shows microsphere diameter versus flow rate.
Figure 28B:
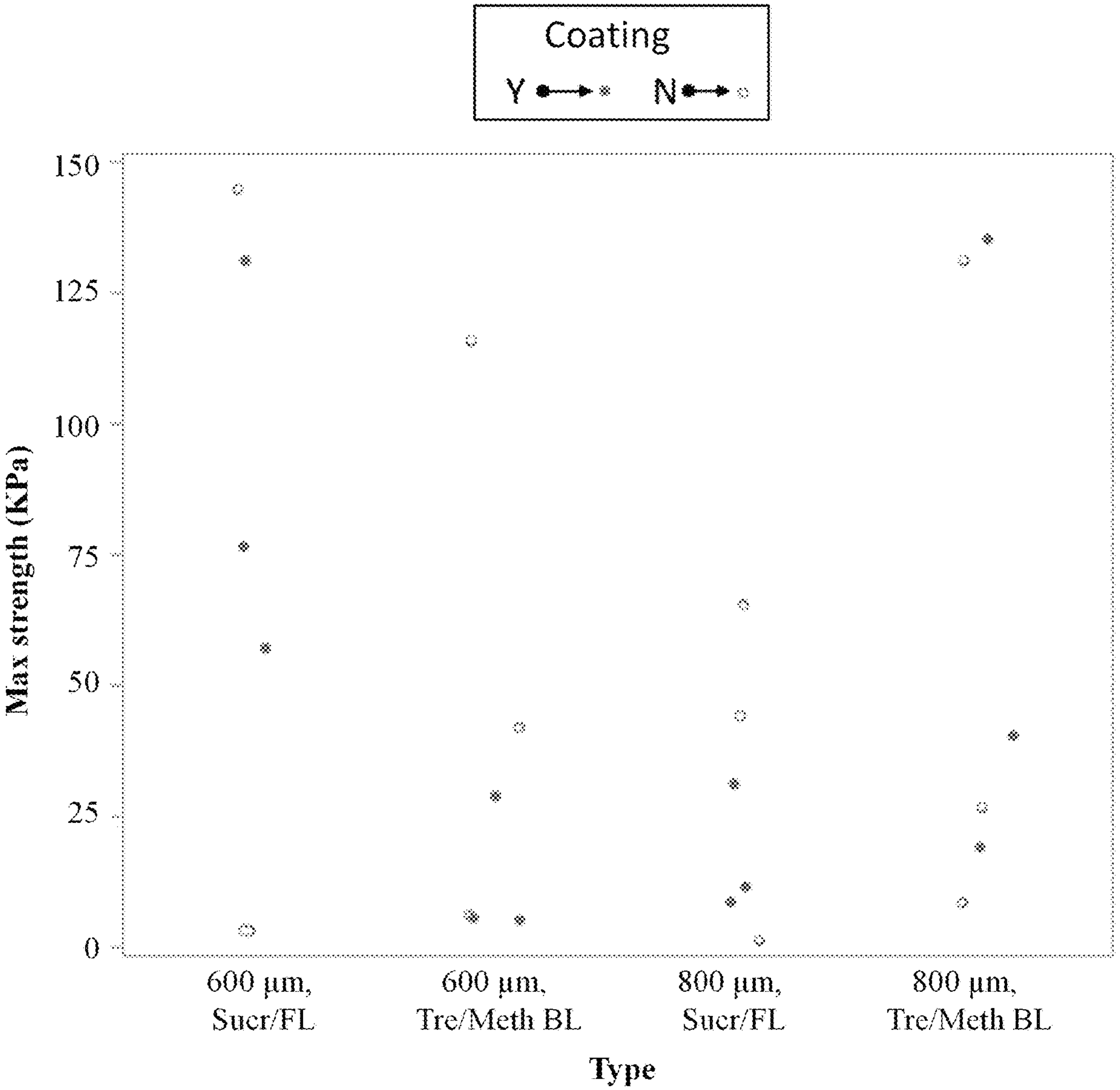
FIG. 28B shows aperture versus flow rate.

Mechanical strength of microspheres that are encapsulated using the methods described herein are shown in FIGS. 28A and 28B. Mechanical strength of the microspheres did not differ significantly through the encapsulation process.

Figure 29A:
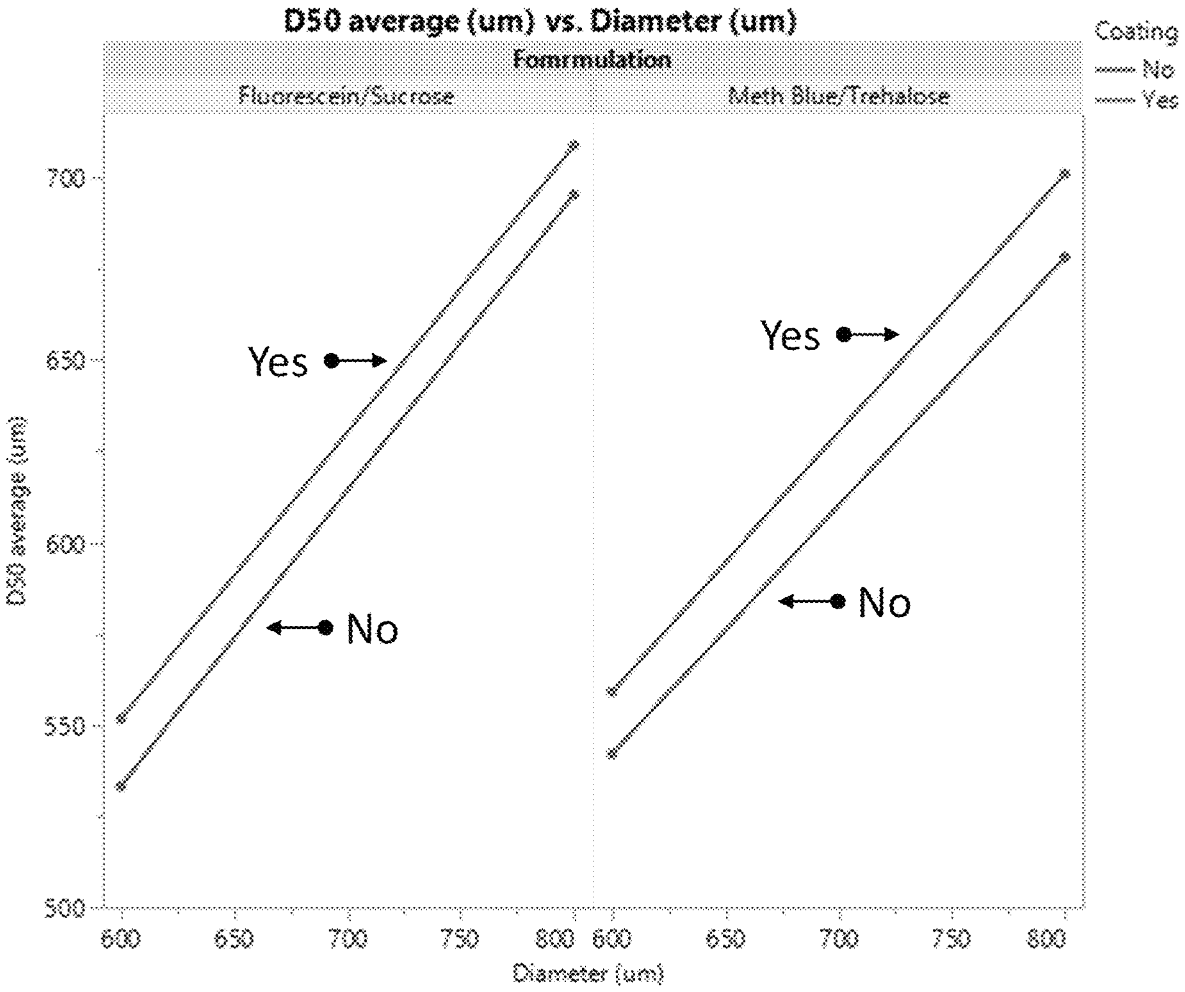
FIGS. 29A and 29B show size distribution of microspheres that are encapsulated using the methods described herein.
Figure 29B:
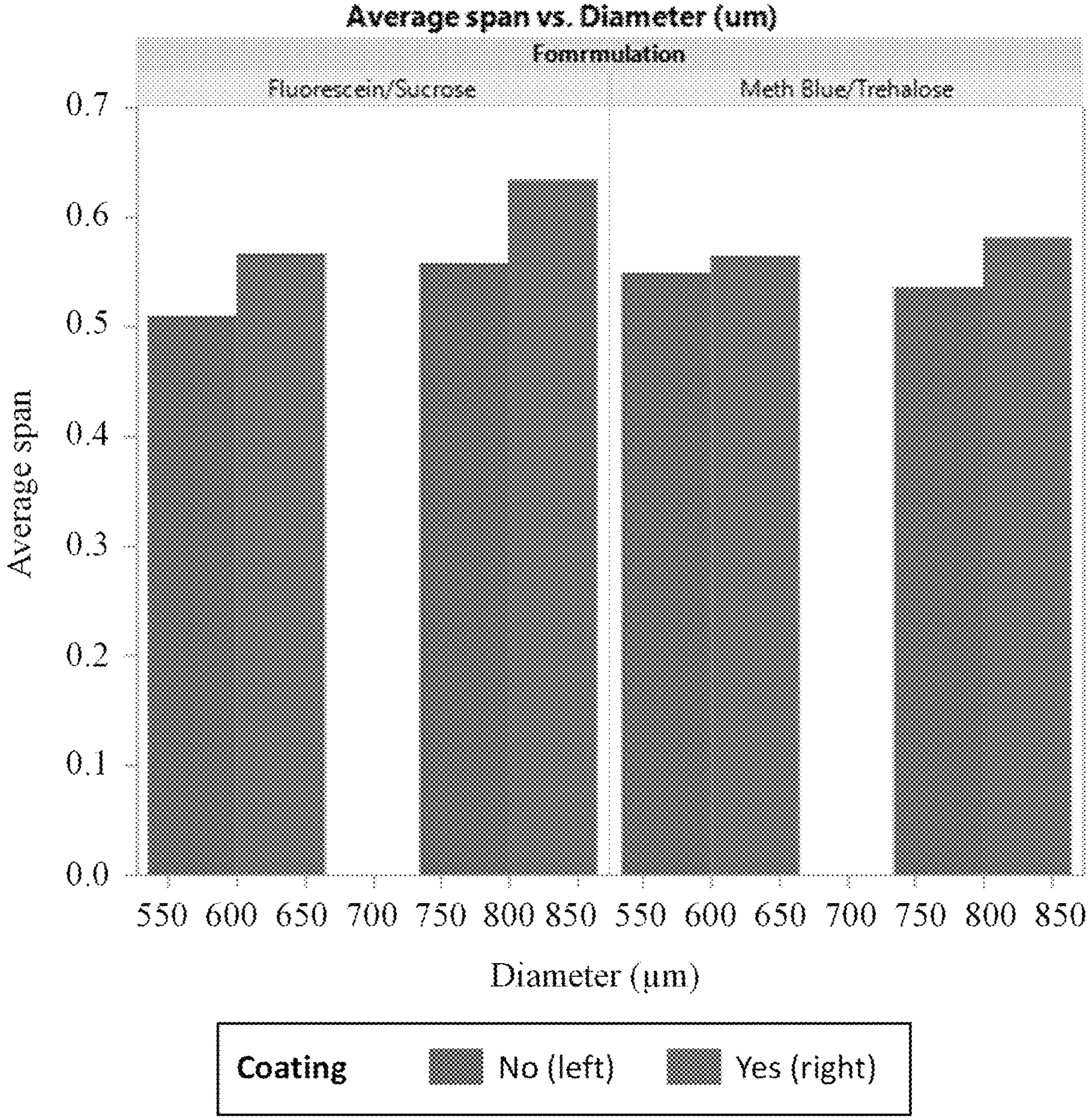

FIGS. 29A and 29B show a larger size of the encapsulated microspheres compared to non-encapsulated microspheres.

Figure 30:
FIG. 30 shows that rehydration of the encapsulated microspheres prepared in accordance with the methods described herein are not impacted by volume of rehydration; turbidity is generated.
Figure 30:
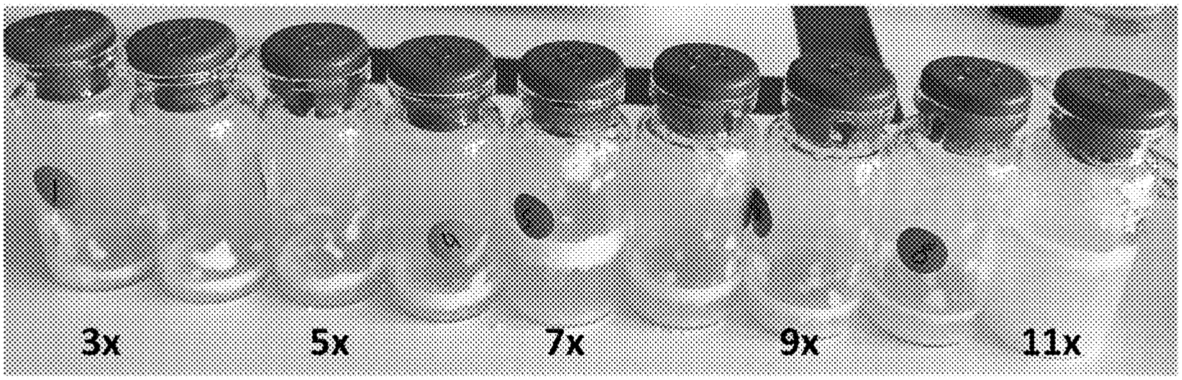
Figure 31:
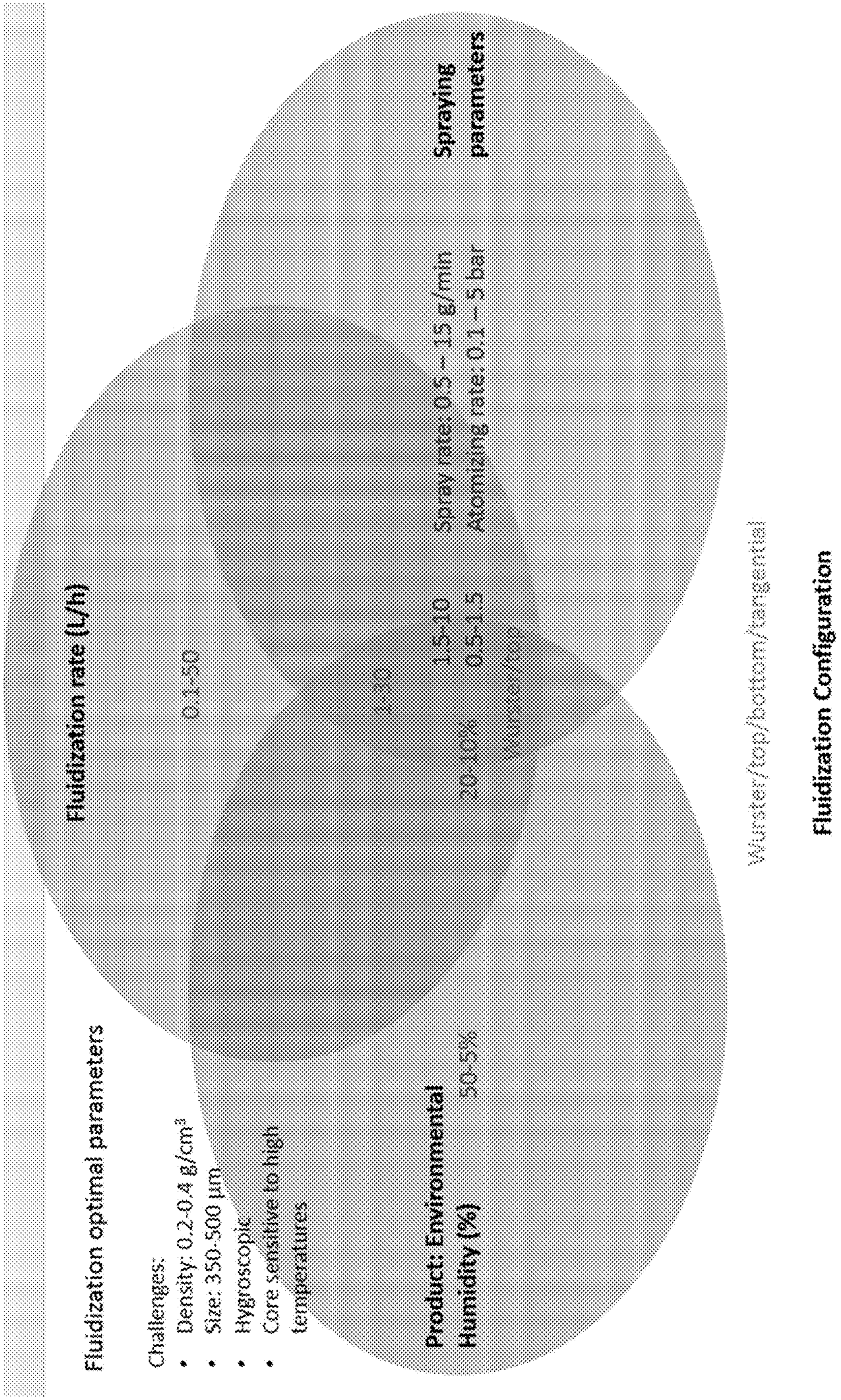
FIG. 31 shows examples of optimized conditions that are suitable for use in the methods and systems described herein.

Rehydration of the encapsulated microspheres prepared in accordance with the methods described herein are not impacted or minimally impacted by volume of rehydration, turbidity is generated, as shown in FIG. 30.

Example 2— Coating of Spray Freeze-Dried Particles

An initially intended formulation for the core material with 50% solid dry matter (to maximize mechanical stability) and 0.5% dye content could not be freeze dried, probably caused by too low Tg' and limited vapor diffusion. Due to this the 2 formulations were changed to 35% solid dry matter with 0.05% dye content. These particles could be spray freeze dried in two sizes without difficulties, even though a cross section of the particles showed a partially collapsed center, which hints at too early interruption of the drying step, which was not relevant for the study. The obtained particles could then be film coated in a fluid bed equipment with a 3"Wurster insert, using standard film coating material. A build-up of static charging had to be prevented by addition of water in the organic solvent spraying solution. The functionality of the polymer film on the particles could be shown.

Trial Targets— A set of 4 spray freezing trials with subsequent coating were set-up with the goal to show functional coating of spray freeze-dried particles. For the tests, 2 different dyes are chosen (Fluorescein vs. Methylenblue) in two different formulations (Sucrose vs. Trehalose as bulking agent).

TABLE 6

Overview of Trials.

| batch number | Type of process | Product | Particle Size |
|---|---|---|---|
| 21-062 | Freezing | Formulation 1; | 600 μm |
| 21-063 | Drying | With Sucrose and Fluorescein | |
| 21-064 | Freezing | Formulation 1: | 800 μm |
| 21-065 | Drying | With Sucrose and Fluorescein | |
| 21-066 | Freezing | Formulation 2: | 600 μm |
| 21-067 | Drying | With Trehalose and Methylenblue | |
| 21-068 | Freezing | Formulation 2; | 800 μm |
| 21-069 | Drying | With Trehalose and Methylenblue | |
| 21-077 | Coating | Formulation 1: With Sucrose and Fluorescein | 800 μm |
| 21-078 | Coating | Formulation 2: With Trehalose and Methylenblue | 600 μm |
| 21-079 | Coating | Formulation 2: With Trehalose and Methylenblue | 800 μm |
| 21-084 | Coating | Formulation 1: With Sucrose and Fluorescein | 600 μm |

Description of the SprayCon750— The spray freezing tower to congeal the droplets. This tower has a height of ca. 3 m and an inner diameter of 0.7 m. The walls of the tower are double walled and are used to cool to cryogenic temperatures by using a mixture of gaseous and liquid nitrogen. The inner wall of the tower is used as a heat exchanger and cools the gas atmosphere in the tower. Product dependent, temperatures of −110 to 130° C. are used. The temperatures in the tower are recorded by 3 temperature sensors in different height positions and used for process control.

One nozzle is used to generate droplets out of the solution in the freezing column. The droplet generation principle is based on the controlled laminar jet break up principle. A gas jet system below the nozzle deflects the droplet jet in different directions. The frozen product is collected in a stainless-steel vessel, which is positioned below the freezing column in a −60° C. freezer.

Rotary Freeze Dryer— 4 trials of the dynamic freeze-drying processes were performed in a LyoMotion 30. The drum of the dryer is able to receive 301 of bulk product. The equipment allows to work with a single walled drum, only with the IR heater as a heating source, or with a double walled drum with a silicone oil circuit in order to control the surface temperature. Even in the configuration with the double walled drum, the IR heater can be used as an additional heating source. Furthermore, a vacuum control of the equipment is possible by using a commercial bleed valve in combination with a PID control.

The precooling of the dryer is performed by cooling the wall of the dryer with a mixture of liquid and gaseous nitrogen and a setpoint of −100° C. and cooling of the silicon oil circuit. At a temperature of −45° C. on the temperature sensor for the product temperature the dryer is ready for charging and the pre-weighted product is filled subsequently. For this the heater flange is opened and the product in filled in the drum manually. The cooling of the chamber wall is now switched off. Vacuum is pulled to low vacuum levels (approx. 100 μbar within 15 min). The double walled drum provides heat for the ice sublimation during the primary and secondary drying step. A temperature probe is located on the surface on the drum with a metal contact to measure the drum temperature. A second temperature probe is mounted in a distance to the drum and gets in contact to the product without any influence of the drum surface temperature and is called "product temperature". Both temperature sensors are rotating together with the drum. After finalisation of the drying the drum rotation direction is reversed and the product is removed out of the drum by discharge scoops. This procedure is performed under vacuum condition and could be used for sampling during the process in a kind of vacuum lock as well.

A part of the freeze-dried products was filled in a tabletop fluid bed apparatus. As a product vessel a 3" Wurster insert with bottom spray and inner partition was used. In this Wurster partition the particles are moving upwards (up bed) by a specific perforation of the distributor plate and by the venturi forces of the nozzle during spraying. A binary nozzle is spraying the coating solution on the particles in the upbed. The residual moisture is removed during fluidization, supported by some slight fluidisation in the downbed (the area around the wurster partition). A specific perforation of the distributor plate in the downbed ensures some fluidisation in this area and reduces the formation of agglomerates. In the expansion zone the particles are returning in the downbed. Blow off filters on the top of the equipment are preventing the product leaving the fluid bed.

Spray freezing formulation— A high solid dry matter may be chosen in order to achieve a high mechanical stability of the products. For the same reason, Dextran 40 may be added to the formulation. Two formulations were tested.

TABLE 7

Formulation 1.
Formulation 1 (21-062; 21-064):

| Component | Fraction (w/w) |
|---|---|
| Sucrose | 33% |
| Dextran 40 | 2% |
| Fluorescein | 0.05% |
| DI-water | 65% |

TABLE 8

Formulation 2.
Formulation 2 (21-066; 21-068)

| Component | Fraction (w/w) |
|---|---|
| Trehalose | 33% |
| Dextran 40 | 2% |
| Methylene blue | 0.05% |
| DI-water | 65% |

TABLE 9

Freezing parameters No. of nozzles.

| Batch # or name | Frequency [Hz] | Nozzle orifice [μm] | Targeted particle size [μm] | Spray rate [g/min] | Deflection pressure [bar] |
|---|---|---|---|---|---|
| 21-062 | 4050 | 300 | 570 | 25.5 | 0.30 |
| 21-064 | 2090 | 400 | 756 | 30.0 | 0.22 |
| 21-066 | 2850 | 300 | 570 | 18.3 | 0.30 |
| 21-068 | 1720 | 400 | 756 | 24.2 | 0.30 |

Description of process setup—The initial solutions were prepared and moved to the top of the spray freezing tower. The spray freezing tower was precooled. Afterwards the frequency for the droplet formation was adjusted and the spray freezing was started.

TABLE 10

Spray Freezing Temperatures.

| Product | Batch # | Temperature Start of Spray freezing Top | Mid | Ground | Temperature End of spray freezing Top | Mid | Ground |
|---|---|---|---|---|---|---|---|
| Sucrose/Dextran/Fluorescein//600 μm | 21-062 | −133.4 | −143.5 | −145.8 | −131.2 | −135.2 | −136.3 |
| Sucrose/Dextran/Fluorescein//800 μm | 21-064 | −142.3 | −144.7 | −151.8 | −132.7 | −136.8 | −138.0 |
| Trehalose/Dextran/Methylenblue//600 μm | 21-066 | −138.5 | −147.0 | −148.3 | −134.9 | −139.4 | −140.5 |
| Trehalose/Dextran/Methylenblue//600 μm | 21-068 | −133.2 | −138.7 | −140.9 | −147.1 | −148.3 | −148.0 |

Observation and remarks—Free flowing products was achieved for all solutions. Due to the high solid dry matter and high amount of the dye, the viscosity was higher than expected. Due to this the intended spray rates of the formulation with Methylenblue could not be achieved due to the choice of too small tubing. Larger tubing may enable higher spray rates.

TABLE 11

Yield Calculation of the Spray Freezing.

| Name of reagent | Meridion Batch # | Sprayed [g] | Absolute yield [g] | Relative yield [%] |
|---|---|---|---|---|
| Sucrose/Dextran/Fluorescein//600 μm | 21-062 | 6138.1 | 5980.0 | 97.5 |
| Sucrose/Dextran/Fluorescein//800 μm | 21-064 | 6811.2 | 6718.3 | 98.6 |
| Trehalose/Dextran/Methylenblue//600 μm | 21-066 | 7450.9 | 6907.5 | 92.7 |
| Trehalose/Dextran/Methylenblue//600 μm | 21-068 | 6945.5 | 6857.7 | 98.7 |

Freeze drying—The product was filled in the precooled pilot scale dryer and the freeze-drying cycle was started. A long secondary drying was programmed to achieve a low residual moisture content of the products.

The drying of the product was possible without difficulties. No sticking or static charging of the product was observed. The cross section of one particle showed a collapsed core. A more conservative end of primary drying or secondary drying may prevent this. Some very minor attrition could be observed, and very good yields were achieved.

TABLE 12

Yield Calculation.

| Batch # or name of product | Charged material [g] | Absolute yield [g] | Solid content [%] | Relative Yield [%] |
|---|---|---|---|---|
| 21-063 | 5996.2 | 2073.0 | 35.05 | 98.8 |
| 21-065 | 6722.6 | 2357.5 | 35.05 | 100.0 |
| 21-067 | 6909.2 | 2399.9 | 35.05 | 99.2 |
| 21-069 | 6862.5 | 2232.0 | 35.05 | 93.0 |

Bulk density— A 500 ml graduated cylinder was used. The cylinder was tared. The freeze-dried product was filled in the cylinder via a funnel until the cylinder was filled between 400-500 ml. Afterwards the weight of the filled product was noted.

TABLE 13

Bulk Density.

| Batch # | Bulk volume [$cm^3$] | Weight [g] | Bulk density [$g/cm^3$] |
|---|---|---|---|
| 21-063 | 475 | 146.3 | 0.3084 |
| 21-065 | 465 | 144.3 | 0.3103 |
| 21-067 | 445 | 144.6 | 0.3250 |
| 21-069 | 470 | 150.8 | 0.3209 |

Drying time and moisture— A residual moisture determination was done by Karl-Fischer titration. The material was dissolved in a mixture of Formamide/Methanol 1:4. Once a clear solution is achieved the titration is started. The drying time is calculated as the time between evacuation and finalization of the secondary drying. The discharging and breaking of the vacuum requires approximately 20 min.

TABLE 14

Residual Moisture %.

| Batch # or name of product | Drying time [h] | Residual moisture [%] Determination 1 | Determination 2 |
|---|---|---|---|
| 21-063 | 33:38 | 0.15 | 0.16 |
| 21-065 | 31:52 | 0.42 | 0.44 |

TABLE 14-continued

Residual Moisture %.

| Batch # or name of product | Drying time [h] | Residual moisture [%] Determination 1 | Determination 2 |
|---|---|---|---|
| 21-067 | 33:48 | 0.24 | 0.25 |
| 21-069 | 34:02 | 0.34 | 0.37 |

TABLE 15

Coating Configuration.

| Fluid bed equipment | Midi Glatt PN18184 |
|---|---|
| Distributor plate | 1-122-00132-2 |
| Mesh on distributor plate | 100 μm |
| Nozzle | type 950 (Schlick) |
| Nozzle liquid insert | 0.5 mm |
| Wurster partition height above distributor plate | 25 mm |
| Diameter of Wurster partition | 45 mm |
| Peristaltic pump | Watson Marlow 530S |
| Peristatic pump head | 505 L |
| Silicone tubing in pump | Double-Y-Tubing set Di = 1.2 mm; Dw = 2.4 mm |
| Silicone tubing downstream | 1.2 × 2.4 |
| Silicone tubing upstream | 1.2 × 2.4 |

TABLE 16

Spraying Solution.

| Component | Fraction |
|---|---|
| Eudragit L100-55 (Polymer) | 3.5% |
| Triethylcitrate (softening reagent/plasticizer) | 0.35% (10% of polymer) |
| Mg Stearate (Anti-Sticking reagent) | 1.23% (35% of polymer) |
| Acetone | 32.3% (34% of liquid fraction) |
| Isopropanol | 48.4% (51% of liquid fraction) |
| Water | 14.2% (15% of liquid fraction) |

Spraying solution preparation—Acetone and Isopropanol are mixed. 50% of this mixture is separated and will be used later. The first half of the organic solvent fraction is stirred vigorously, and the preweighted amount of Eudragit L100-55 polymer is added carefully to the organic solvent mixture and stirred for approx. 60 min until all polymer is completely dissolved and a clear solution is visible.

Triethylcitrate and Mg stearate are added to the second half of the organic solvent mixture and stirred for 5 minutes.

After the Eudragit solution is clear, the Triethycitrate/Mg stearate suspension is added and stirred shortly. Afterwards the water is added carefully while mixing the suspension. Afterwards the suspension is stirred for 5 min and sieved through a 100 μm mesh. If the sieving stops, the suspension on the sieve has to be carefully stirred with the spoon. During the spraying duration, the suspension is stirred continuously with a magnet stirrer.

Process Parameters. Filling height of product vessel—Approx. 375 g of product was filled in the 3" Wurster.

TABLE 17

Recipe Parameters.

| Parameter description | Value |
|---|---|
| Temperature Inlet | 40° C. |
| Inlet nitrogen volume | 25-30 $Nm^3/h$ |
| Compressed nitrogen pressure nozzle | 1.2 bar (0.7 bar in the first 5 min) |
| Spray rate | ~7 g/min (8.8 ml/min) |
| Pump rotation speed | 11 rpm |

Approximately half of the spraying solution was applied on the product. Afterwards the equipment was completely cleaned, and the remaining spraying liquid was sprayed. This intermediate cleaning was done to ensure that any eventually remaining dye from the surfaces of the equipment was removed, which was deposited due to attrition in the beginning of the process. It was considered, that after spraying half of the spraying liquid a continuous thin film was applied on the product and act as a kind of 'seal coat'. Further attrition was regarded as not contaminated by the dye anymore.

TABLE 18

Amount of Spraying Liquid Applied on the Product.

| Batch # | Filled product [g] | Spraying solution [g] | Sprayed solution in first step | Solid sprayed | Product weight after 1$^{st}$ spraying | Weight gain 1$^{st}$ step [%] | Sprayed solution in second step | Solid sprayed [g] | Weight after 2$^{nd}$ spraying | Weight gain 2$^{nd}$ step | Total weight gain [%] |
|---|---|---|---|---|---|---|---|---|---|---|---|
| 21-084 | 375.1 | 1200 | 580 | 29.46 | 413.3 | 102.0 | 620 | 31.50 | 425.4 | 95.6 | 97.6 |
| 21-077 | 379.0 | 1200 | 700 | 35.56 | 409.0 | 98.7 | 500 | 25.40 | 427.4 | 98.4 | 97.1 |

TABLE 18-continued

Amount of Spraying Liquid Applied on the Product.

| Batch # | Filled product [g] | Spraying solution [g] | Sprayed solution in first step | Solid sprayed | Product weight after 1st spraying | Weight gain 1st step [%] | Sprayed solution in second step | Solid sprayed [g] | Weight after 2nd spraying | Weight gain 2nd step | Total weight gain [%] |
|---|---|---|---|---|---|---|---|---|---|---|---|
| 21-078 | 375.1 | 1420 | 920 | 46.74 | 420.1 | 99.6 | 500 | 25.40 | 442.1 | 99.2 | 98.9 |
| 21-079 | 375.4 | 1500 | 850 | 43.18 | 454.1 | 108.0* | 650 | 33.02 | 485.4 | 99.6 | 107.5* |

*Eventually a high amount of residual organic solvent was entrapped in the product. The particles appeared "softer" compared to the other products.

Observations and remarks—The product has a high tendency to build up static charging in the beginning of the process. Due to this, the spraying of the spray liquid may be started directly after fluidisation. In order to achieve this, following measures were taken: 1. The equipment was preheated without product; 2. The product was filled in the product container; 3. The spray tubing was filled with spray liquid and connected to the nozzle; and 4. The fluidisation gas was switched, and the spraying was started subsequently. Furthermore, water was added to a certain extent (15%) in the spraying liquid.

In the beginning, relatively "wet" conditions were chosen (lower spraying pressure and lower gas volume) to prevent any static charging. After approximately 5 min more dry conditions could be chosen. A spray pressure below 1.0 bar led to some agglomeration with the given conditions. Due to this, just pressures above this level are chosen, but have to be regarded in conjunction to the liquid feed rate to the nozzle (e.g., a higher feed rate would eventually require higher spraying pressure as well in order to keep the droplet size, which is created by the nozzle, constant).

The amount of water should be reduced for optimized film properties. In certain aspects, 15% of water is the upper limit of the water content in the spraying solution, and may lead to a higher film porosity.

Test of film functionality— After coating, each of the products was checked for film functionality. In certain aspects, the polymer may dissolve at pH values larger than 5.5.

Following test was performed. A 10% citric acid solution and a 3% sodium hydroxide solution were prepared. A coated sample of the particles (~1-2 g) was added to each of these solutions in a beaker.

The test was considered to be successful, if the particles in the sodium hydroxide solution dissolve withing 5 min, while the particles in the citric acid solution remain intact and no colouring of the surrounding solution is visible. This was the case for all products.

Summary and conclusion— The initially intended formulations with 50% solid dry matter and a dye content of 0.5% was not successful. The spray freezing was possible but the freeze-drying of the formulation ended up in a completely collapsed product. Either the drying conditions were too progressive or the Tg' of the formulation was too low due to the high amount of Na-Fluorescein salt. Meanwhile preliminary experiments in the fluid bed (which were performed in parallel) already had shown, that even lower solid dry matter concentrations will allow for a coating of the particles, which are able to withstand the mechanical forces in the fluid bed. Due to this the solid dry matter was reduced from 50% to in total 35% and the dye content was reduced from 0.5% to 0.05%. The result was a product, which could be spray frozen and freeze dried without difficulties.

The cross section of cut particles after coating showed partially collapsed products in the center of the spheres. It was not systematically checked, whether this was the case at all particles. Most probable the drying conditions at the end of primary drying were too progressive for this formulation either. Due to the small size of the pores, the residual moisture eventually could not evaporate fast enough while the temperatures are already increasing at the end of primary drying. To avoid this meltback in the center of the particles an optimization of the formulation or the process conditions may be required. Nevertheless, the properties of the particles for coating were identical to particles which would have been dried without collapsed cores.

During coating initial experiments showed a strong tendency for static charging if no water is present in the process. Due to this, the coating solution was adapted containing a certain fraction of water (15% of the liquid phase). Furthermore particle fluidization without spraying (for e.g. prewarming of the equipment) should be avoided as well. The tendency for static charging was created by the particles itself, but later on as well by the coating film. An optimization of the coating formulation may be required, if static charging should be avoided during processing without spraying. With specific process conditions, even aqueous coating formulations might be considered.

The functionality of the polymer film on the particles was shown for all products. Due to this it could be concluded that it is possible to coat freeze dried particles in a way, that their properties can be modified by coating, such that they can get protected against moisture, and that a dissolution could be externally triggered (e.g., pH change).

The shell may include an anti-tacking agent. In one implementation, the anti-tacking agent is present in an amount of at least 5% dry content of the shell, with the formulation containing at least 0.5 wt. % PEG40 stearate. For example, the anti-tacking agent may be present in an amount of about 5% to about 60% dry content of the shell, including all ranges, subranges, and values therein. For example, the formulation may contain about 0.5-3.5 wt. % PEG40 stearate.

The coating may include an anti-tacking agent. In one implementation, the anti-tacking agent is present in the liquid formulation in an amount of at least about 10%, with the coating containing about 0.5-3.5 wt. % PEG40 stearate. In another implementation, the anti-tacking agent is present in the solid phase formulation in an amount of at least about 6%, with the coating containing about 0.5-3.5 wt. % PEG40 stearate. For example, the anti-tacking agent may be present in an amount of about 10% to about 30% in the liquid formulation, including all ranges, subranges, and values therein.

Figure 32:
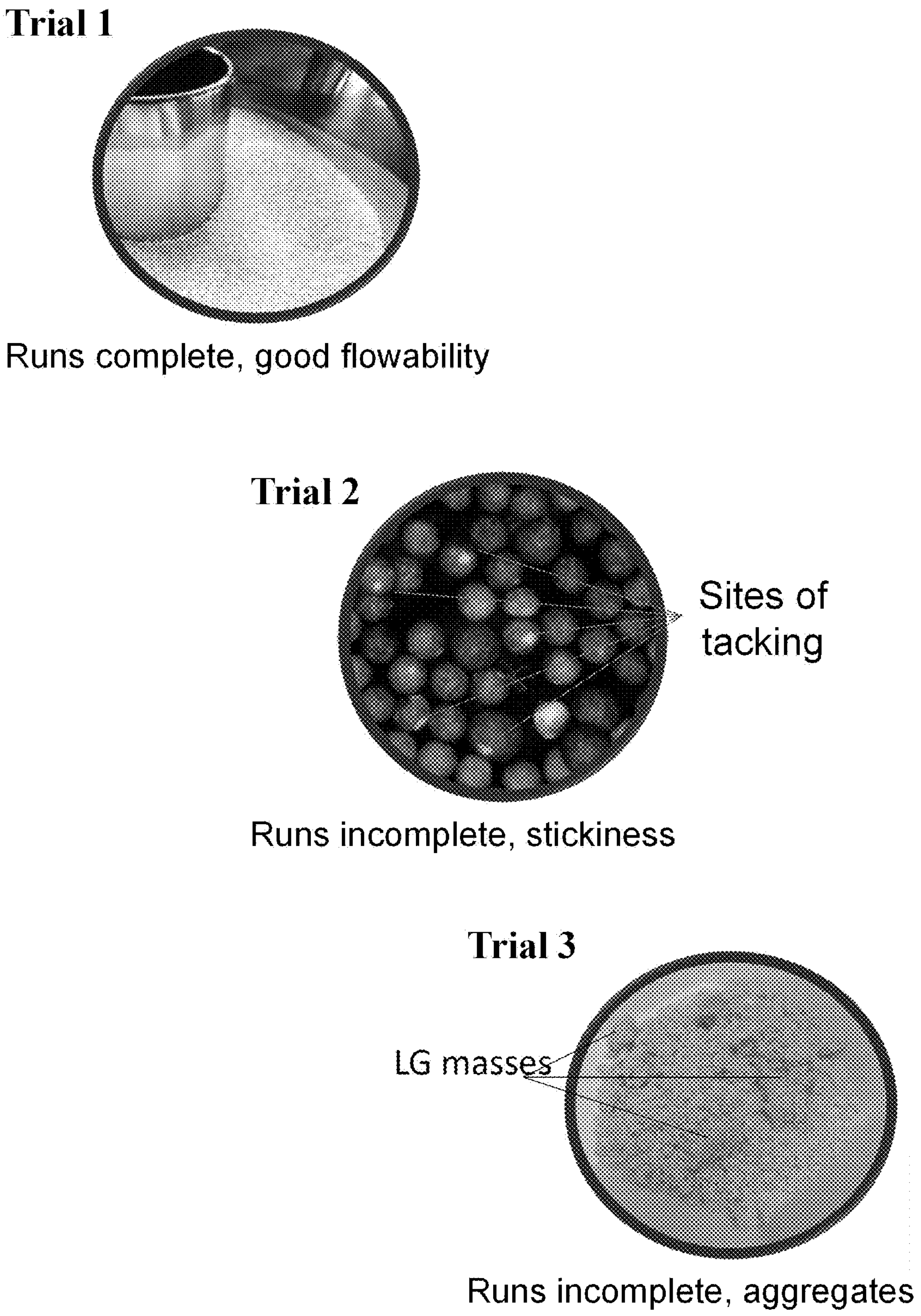
FIG. 32 shows images of encapsulated microspheres with different shell formulations.

Now referring to FIG. 32, the effect of using different shell formulations on coating is shown by Trials 1, 2, and 3. Trial 1 depicts a complete run with good flowability. The shell formulation in Trial 1 comprises Mg stearate (anti-static agent), triethylcitrate (plasticizer), eudragit (polymer), and Mg stearate (anti-tacking agent). Trial 2 depicts an incomplete run with sticky, partially coated lyophilised microspheres. The shell formulation in Trial 2 comprises Efka (anti-static agent), Makkon (plasticizer), and polymers Protect and VA64. Trial 3 depicts an incomplete run with large masses of aggregates of the lyophilised microspheres. The shell formulation in Trial 3 comprises Efka (anti-static agent), Makkon (plasticizer), and polymers CA & hydroxypropyl methylcellulose (HPMC).

Figure 33:
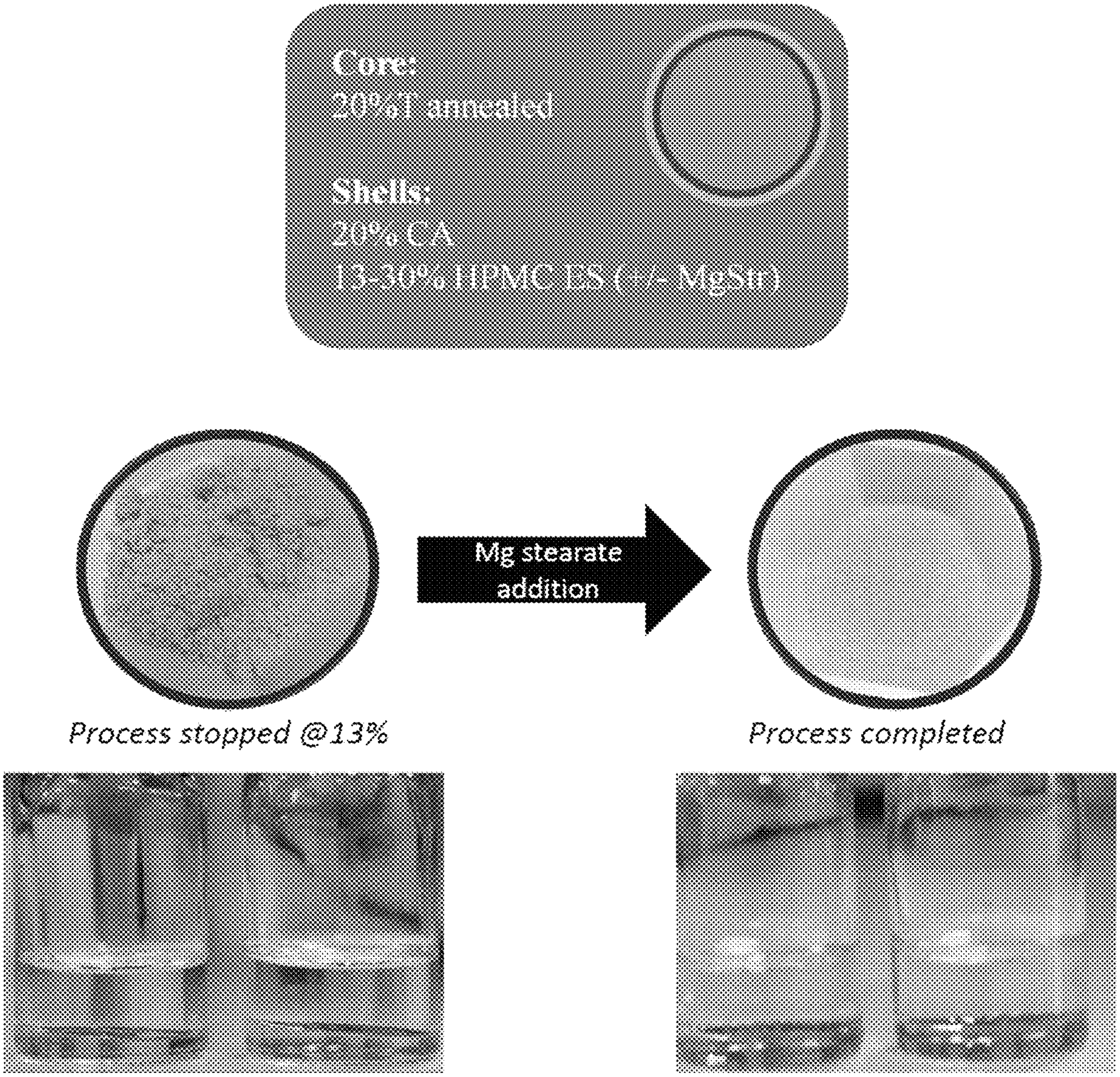
FIG. 33 shows encapsulated microspheres before and after the addition of Mg stearate.

FIG. 33 shows a non-limiting example of the difference between including and not including an anti-tacking agent. In this example, the addition of Mg stearate (as an anti-tacking agent) results in a complete process without aggregates. An additional, non-limiting example of an anti-tacking agent is PEG stearate, such as PEG40 stearate and PEG100 stearate.

Figure 34A:
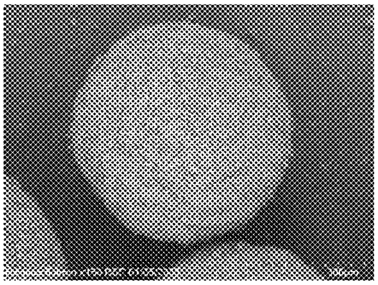
FIGS. 34A-34E show images of encapsulated microspheres with no coating (FIG. 34A) or 1% Mg Stearate (FIG. 34B), 0.6% Gly Stearate (FIG. 34C), 3.5% PEG40 Stearate (FIG. 34D), or 7.9% PEG100 Stearate (FIG. 34E) in the coating formulation.
Figure 34B:
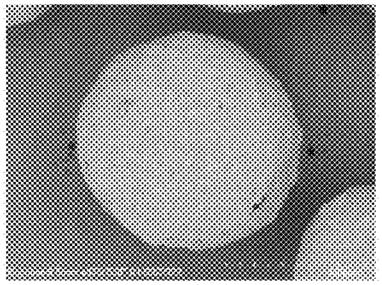
Figure 34C:
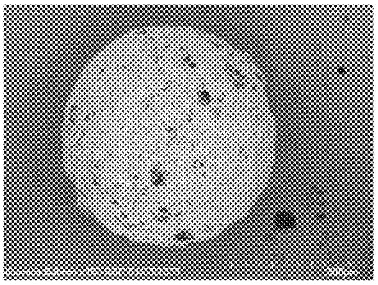
Figure 34D:
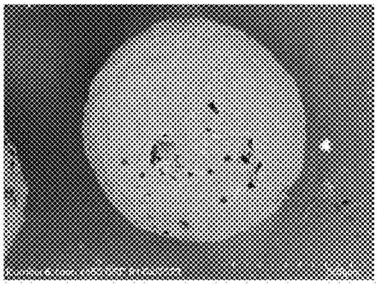
Figure 34E:
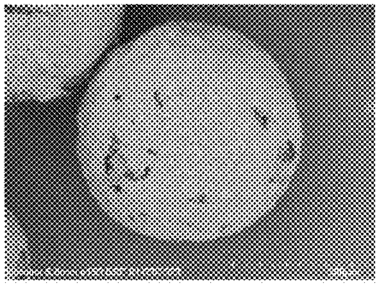

PEG stearate may be included in the shell or coating formulation as an anti-tacking agent. Non-limiting examples of the anti-tacking effect of PEG stearate is shown in FIGS. 34A through 34E. For example, an uncoated lyophilised microsphere is shown in FIG. 34A and coated or partially coated lyophilised microspheres are shown in FIGS. 34B through F34E. In FIG. 34B, the formulation includes the anti-tacking agent Mg stearate at 1% and the lyophilised microsphere is fully coated. In FIG. 34C, the formulation includes Gly stearate, which is not anti-tacking, at 0.6% and the lyophilised microsphere is partially coated. In FIG. 34D, the formulation includes 3.5% PEG40 stearate and the lyophilised microsphere is partially coated, though the coating is greater than when Gly stearate was used in FIG. 34C. In FIG. 34E, the formulation includes 7.9% PEG100 stearate and the lyophilised microsphere is partially coated, though the coating is greater than when Gly stearate was used in FIG. 34C.

Figure 35:
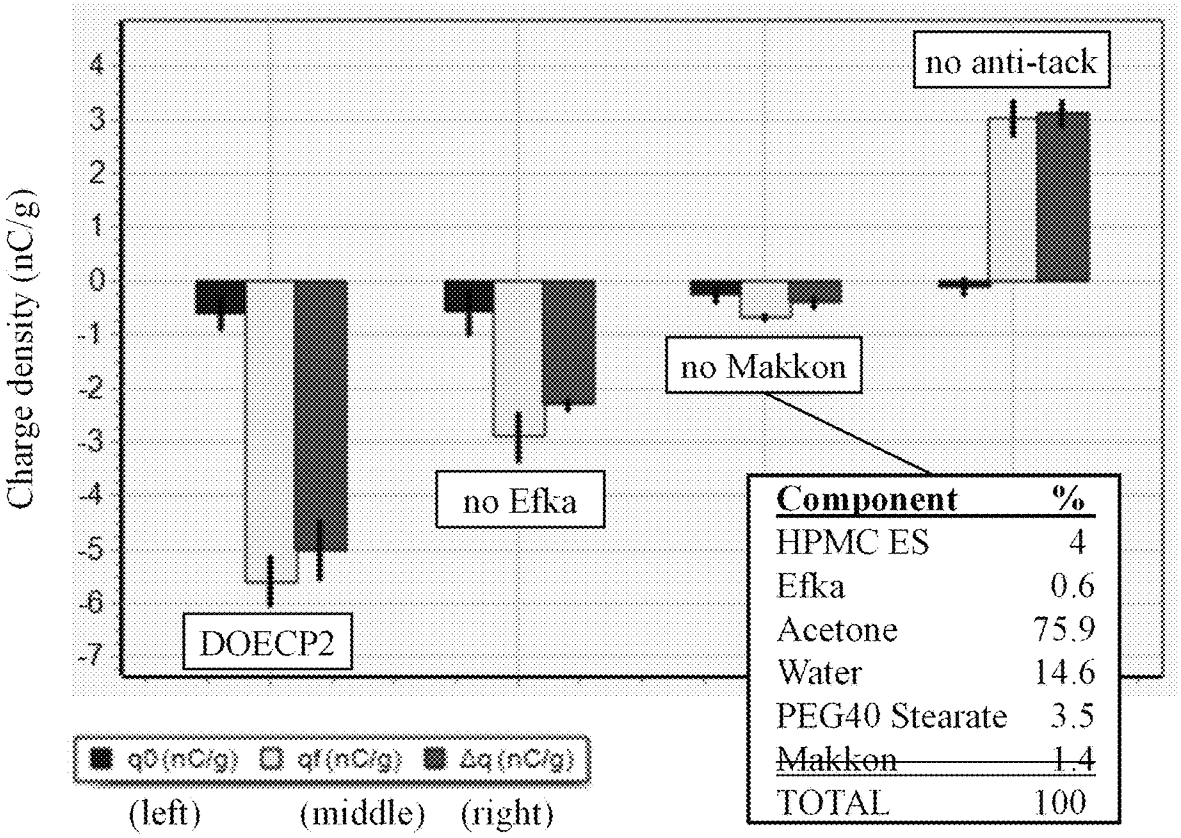
FIG. 35 shows charge density of encapsulated microspheres prepared in accordance with the methods described herein.
Figure 36A:
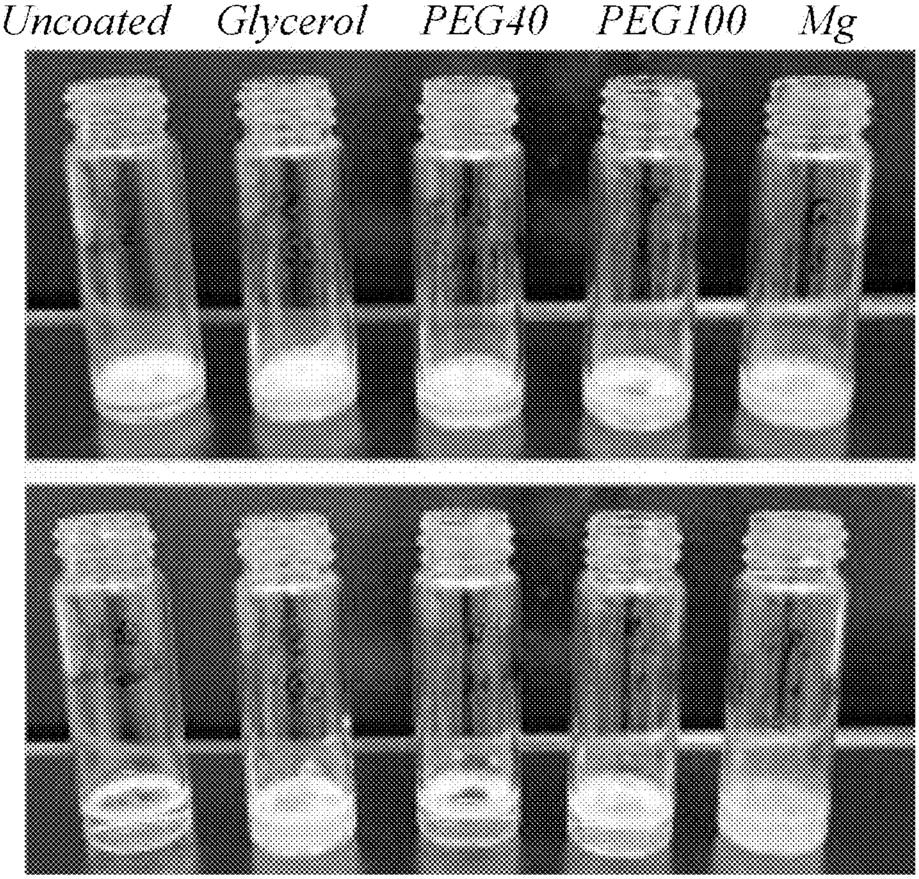
FIGS. 36A and 36B show images of different coating formulations (FIG. 36A) and encapsulated microspheres (FIG. 36B).
Figure 36B:
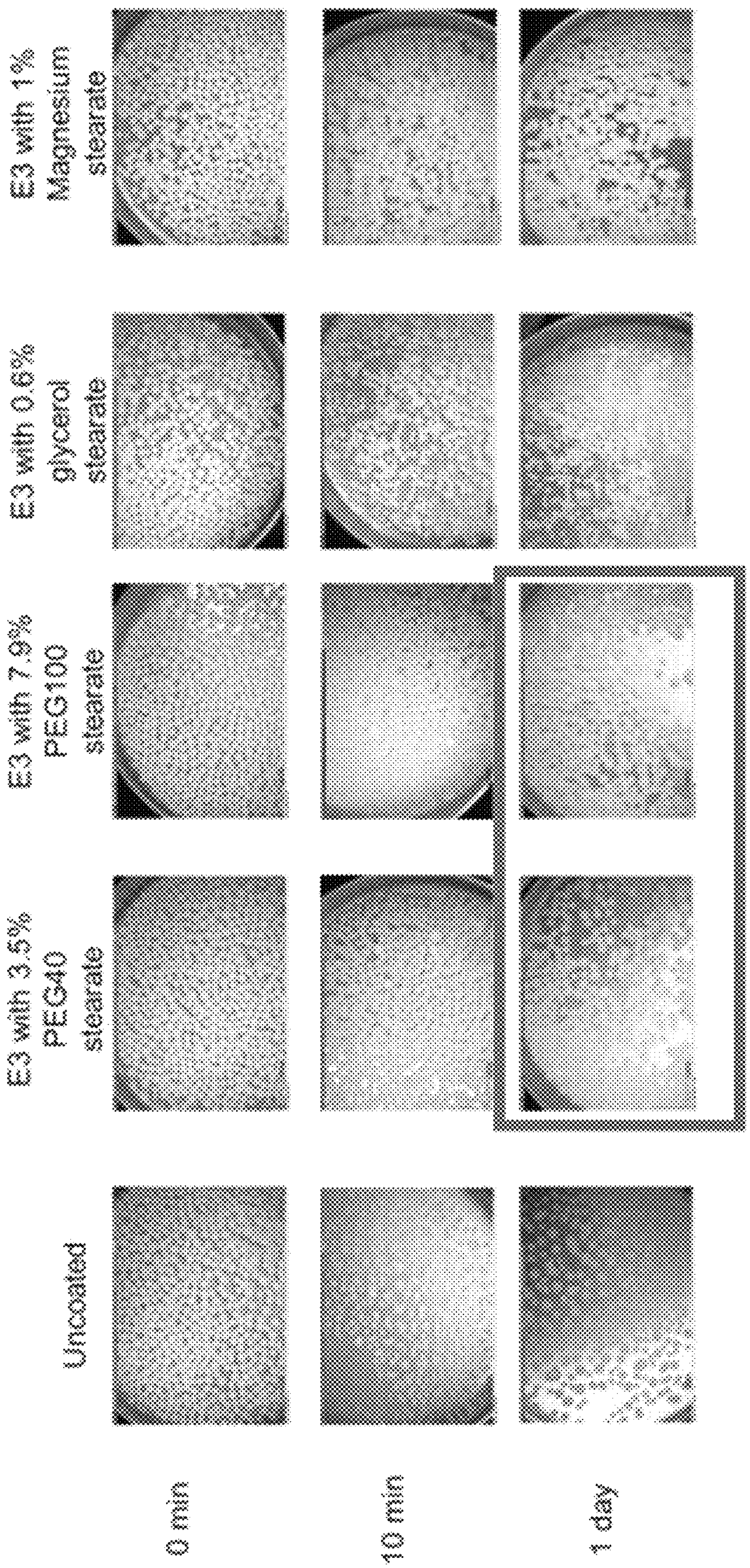

In an example, PEG40 stearate may act as a plasticizer and thereby replace Makkon to lower tribocharging affinity (FIG. 35). PEG40 stearate may cause foaming (FIG. 36A). Anti-foaming agents may be added to the shell formulation to mitigate foaming created by PEG40 stearate. In addition, PEG40 stearate may provide a moisture barrier (FIG. 36B). In another example, PEG40 stearate may provide a moisture barrier.

Figure 37A:
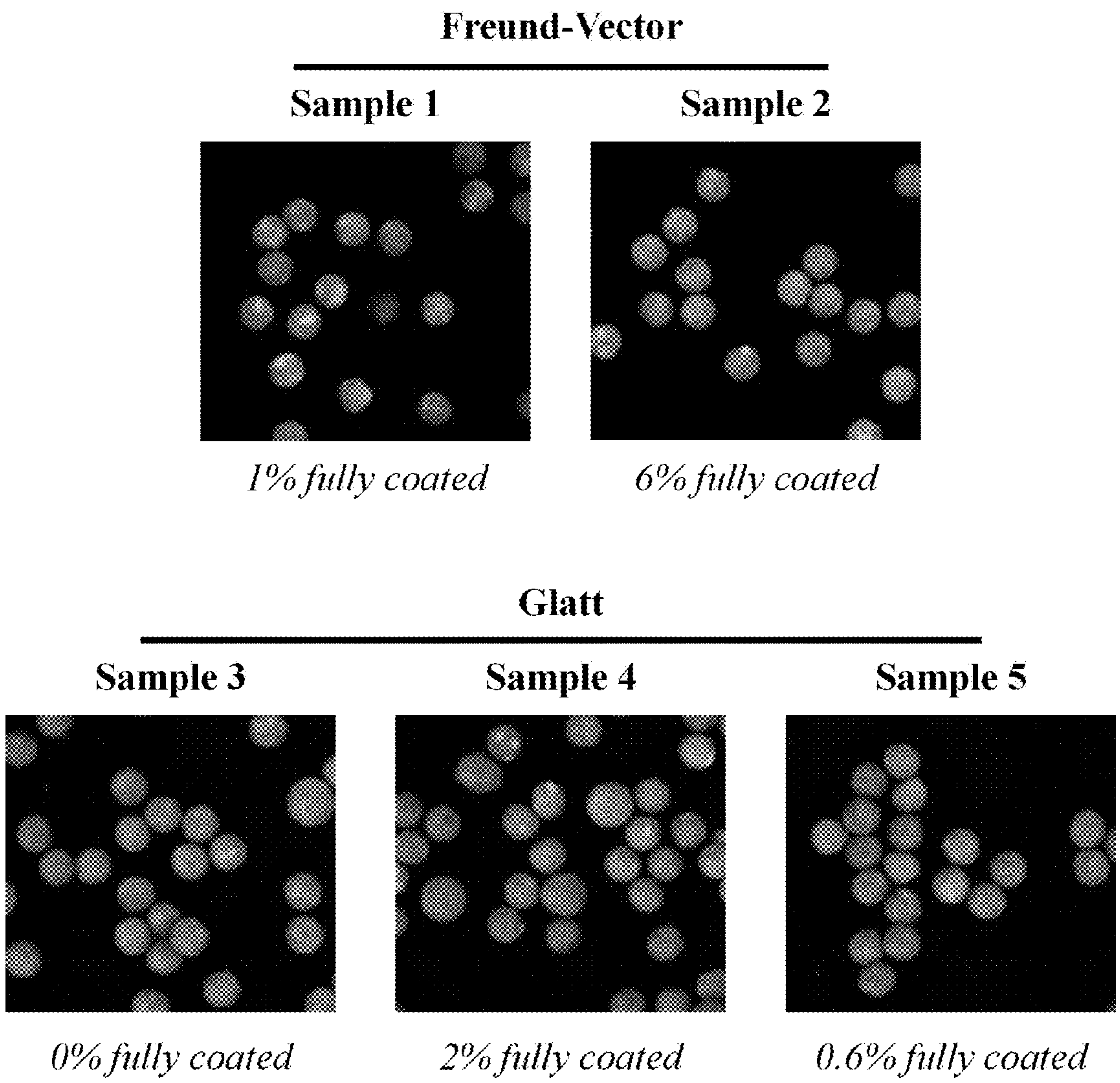
FIGS. 37A-37F show examples of encapsulated microspheres prepared in accordance with methods described herein (FIG. 37A), including SEM images and Camsizer data (37B-37F).
Figure 37B:
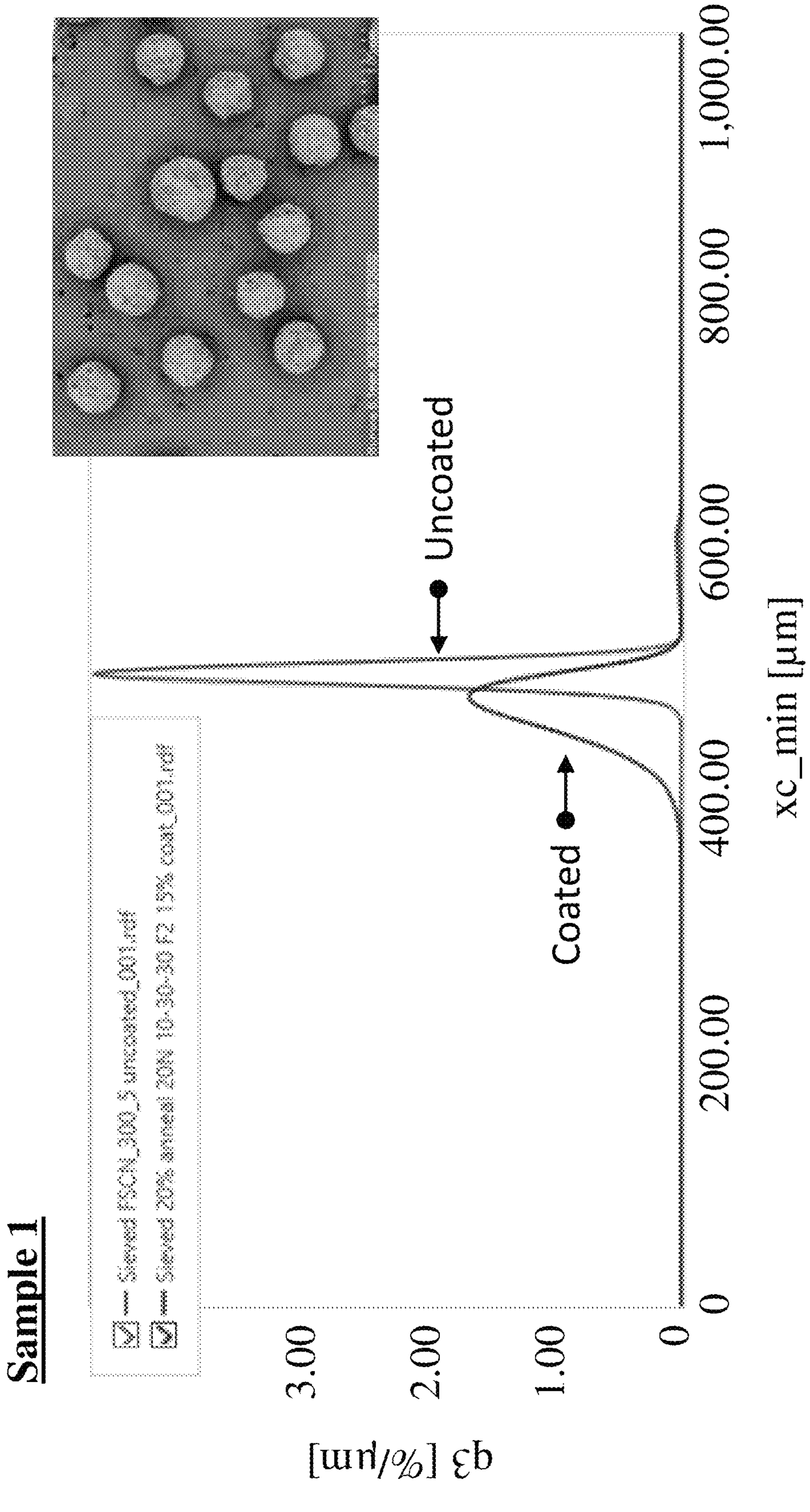
Figure 37C:
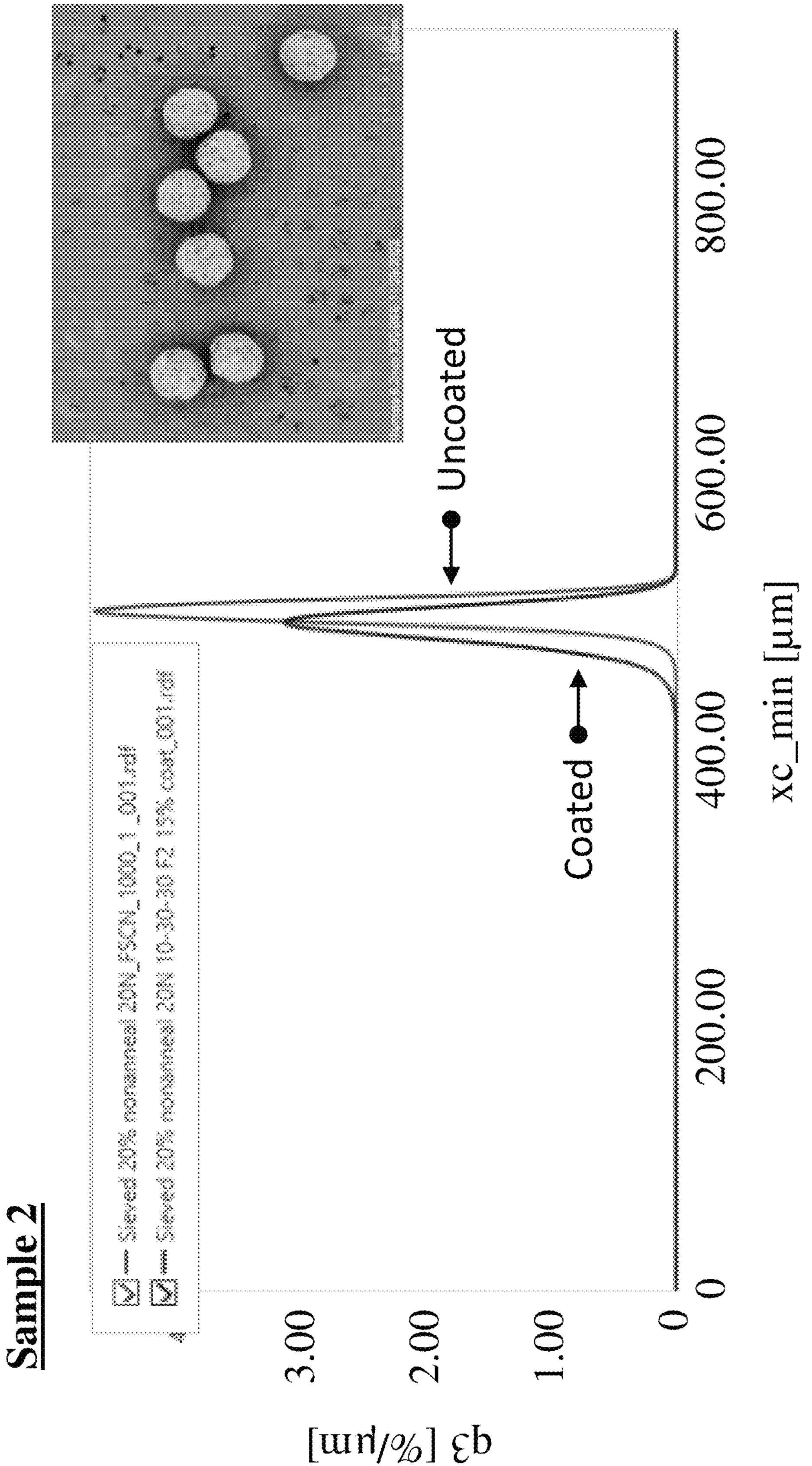
Figure 37D:
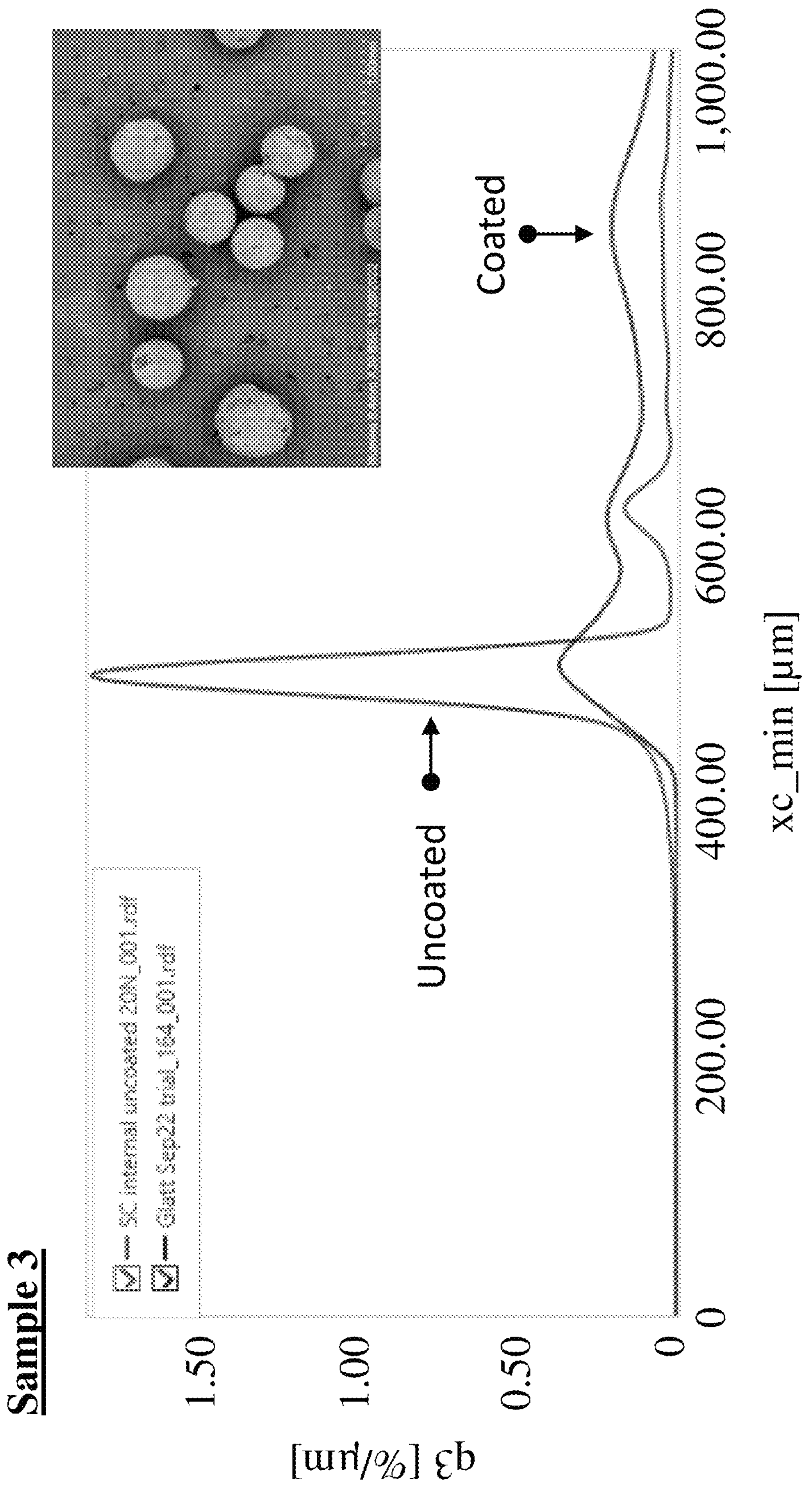
Figure 37E:
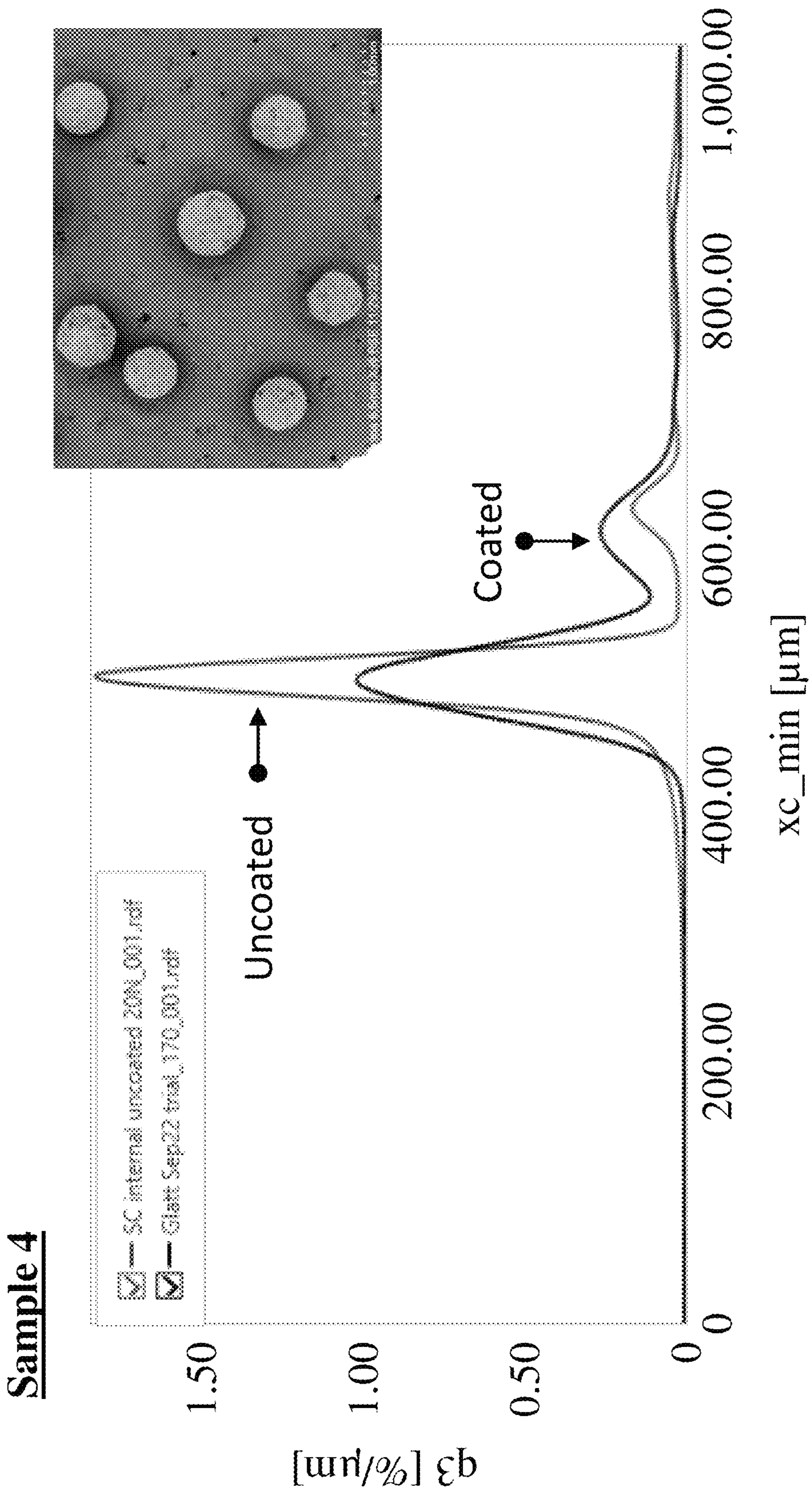
Figure 37F:
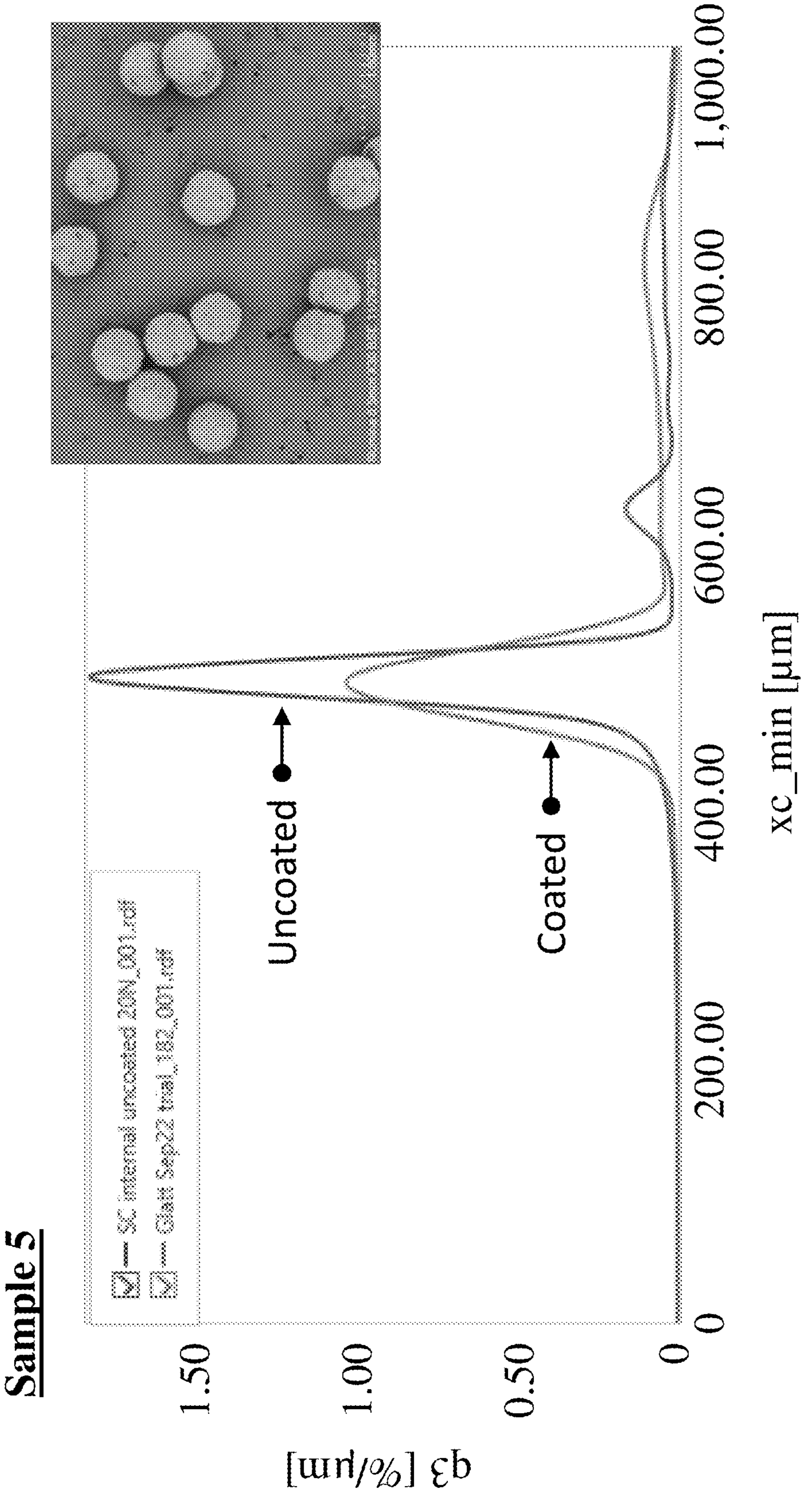

Now referring to FIGS. 37A through 37F, shown are the results from example processes of coating lyophilised microspheres as disclosed herein. In an example, lyophilised microspheres were coated using a top-spray configuration (Samples 1 and 2; FIGS. 37A through 37C). In another example, lyophilised microspheres were coated using a Wurster configuration (Samples 3 through 5; FIGS. 37A and 37D through 37F). FIG. 37A shows images of lyophilised microspheres from Samples 1 through 5 with varying degrees of coating, from 0% to 6% coating. FIGS. 37B through 37F show SEM images and Camsizer data of coating and uncoated lyophilised microspheres for each of Samples 1 through 5.

Example 3— Conditions for Fluidization

Fluidization as described herein was configured in a manner to promote improved encapsulation and/or coating of lyophilised microspheres, as shown in FIG. 32.

There are various challenges that need to be addressed when encapsulating and/or coating lyophilised microspheres, including, but not limited to the physical characteristics of the lyophilised microsphere such as having a density of between 0.2-0.4 g/cm$^3$, having a size of between 350-500 μm, their hygroscopic nature, and their core sensitivity to high temperatures. Accordingly, various parameters and conditions in fluidization where optimized to overcome such challenges. For example, the fluidization rate may be between 0.1 L/h and 50 L/h and further optimized to between 1 L/h and 30 L/h. The spraying parameters may likewise be optimized to improve results. For example, the spray rate may be between 0.5 g/min and 15 g/min, or more particularly optimized to between 1.5 g/min and 10 g/min. Similarly, the atomizing rate may be between 0.1 bar and 5 bar, or more particularly, between 0.5 bar and 1.5 bar. The environmental humidity may similarly be optimized to between 5% and 50%, but more particularly between 10% and 20%. The fluidization configuration may be Wurster, top, bottom, or tangential, but may be particularly optimized to a Wurster or top configuration. In one implementation, the conditions are optimized to have a fluidization rate of between 1 L/h and 30 L/hr, a spray rate of between 1.5 g/min and 10 g/min, an atomizing rate of between 0.5 bar and 1.5 bar, an environmental humidity of between 10% and 20%, and a Wurster or top spray fluidization configuration.

Substrate material needs to be heated for solvents in coating solution to evaporate in process. The material cannot be fluidized to achieve this as in the absence of spraying coating solution static charges will build up. Spraying cannot be initiated without heat for fear of nozzle clogging. The solution discovered herein includes preheating the instrument before adding substrate, then adding substrate rapidly keeping heat and immediately initiate spraying.

Table 14 describes examples of fluidization parameters as described herein.

TABLE 19

Examples of Fluidization Parameters.

| | Coating parameters | | | Bed Geometry | | |
|---|---|---|---|---|---|---|
| | Spray rate (g/min) | Atomization Rate (bar) | Fluid rate (m$^3$/h) | Nozzle diameter (mm) | Drum Diameter (mm) (top/bottom) | Fill height (mm) |
| Mini | 3-5 | 0.5-1 | 10-15 | 0.5 | 160/65 | 120 (height of product container) |
| Midi | 7 | 0.7-1.2 | 25-30 | 0.5 | 200/85 | 185 (height of product container) |
| FV | 1.7-3 | 0.7 | 1.5 | 0.5 | 130/45 | 100 (based on yellow 2ON fill height) 60 mm (based on sugar beads) |

Although preferred implementations have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

Various non-limiting implementations of this disclosure are described below:

[Implementation A] A method comprising: providing one or more lyophilised microspheres in a mixing vessel at a first temperature; and generating a fluidized bed of the one or more lyophilised microspheres in the mixing vessel, wherein the fluidized bed has a fluidization rate of between about 1 cubic meters per hour ($m^3$/h) and about 30 $m^3$/h, under conditions effective to encapsulate the one or more lyophilised microspheres with a coating formulation.

[Implementation B] A method according to Implementation [A] above, or according to other Implementations of the disclosure, wherein the fluidized bed has an environmental humidity of between about 10% and about 20%.

[Implementation C] A method according to Implementation [A] or [B] above, or according to other Implementations of the disclosure, wherein the coating formulation comprises a water content of between about 0.1 wt. % and about 5 wt. %.

[Implementation D] A method according to any one of Implementations [A]-[C] above, or according to other Implementations of the disclosure, wherein the encapsulated lyophilised microspheres comprise a water content of below about 5 wt. %.

[Implementation E] A method according to any one of Implementations [A]-[D] above, or according to other Implementations of the disclosure, wherein the coating formulation is applied by at least one spray nozzle.

[Implementation F] A method according to Implementation [E] above, or according to other Implementations of the disclosure, wherein the at least one spray nozzle has a diameter of between about 0.1 mm and about 1.5 mm.

[Implementation G] A method according to any one of Implementations [A]-[F] above, or according to other Implementations of the disclosure, wherein the coating formulation is sprayed on the one or more lyophilised microspheres in the fluidized bed.

[Implementation H] A method according to Implementation [G] above, or according to other Implementations of the disclosure, wherein the coating formulation is applied at a spray rate of between about 1.5 grams per minute (g/min) and about 10 g/min.

[Implementation I] A method according to Implementation [G] or [H] above, or according to other Implementations of the disclosure, wherein the coating formulation is applied at an atomizing rate of between about 0.5 bar and about 1.5 bar.

[Implementation J] A method according to Implementation [A] above, or according to other Implementations of the disclosure, wherein generating the fluidized bed comprises: elevating the first temperature in the mixing vessel to a second temperature; and supplying air in the mixing vessel under conditions effective to float the one or more lyophilised microspheres in the air.

[Implementation K] A method according to any one of Implementations [A]-[J] above, or according to other Implementations of the disclosure, wherein the mixing vessel comprises a single open vessel.

[Implementation L] A method according to any one of Implementations [A]-[K] above, or according to other Implementations of the disclosure, wherein the mixing vessel comprises one or more cylindrical draft tube which is disposed in the mixing vessel.

[Implementation M] A method according to any one of Implementations [A]-[L] above, or according to other Implementations of the disclosure, wherein the mixing vessel comprises an outer circumference.

[Implementation N] A method according to Implementation [M] above, or according to other Implementations of the disclosure, wherein the one or more cylindrical draft tube is between about 25 mm and about 500 mm away from the outer circumference of the mixing vessel.

[Implementation O] A method according to any one of Implementations [A]-[N] above, or according to other Implementations of the disclosure, wherein the air is supplied by an air supply unit.

[Implementation P] A method according to any one of Implementations [A]-[O] above, or according to other Implementations of the disclosure, wherein the fluidized bed is in a Wurster configuration, a top spray configuration, or a combination thereof.

[Implementation Q] A method according to Implementation [P] above, or according to other Implementations of the disclosure, wherein the fluidized bed is in a Wurster configuration.

[Implementation R] A method according to Implementation [P] above, or according to other Implementations of the disclosure, wherein the fluidized bed is in a top configuration.

[Implementation S] A method according to any one of Implementations [A]-[R] above, or according to other Implementations of the disclosure, wherein the first temperature comprises a temperature at or below about 30° C.

[Implementation T] A method according to any one of Implementations [K]-[S] above, or according to other Implementations of the disclosure, wherein the second temperature comprises a temperature above about 40° C.

[Implementation U] A method according to any one of Implementations [A]-[T] above, or according to other Implementations of the disclosure, wherein the mixing vessel has a diameter of between about 25 mm and about 500 mm.

[Implementation V] A method according to any one of Implementations [A]-[U] above, or according to other Implementations of the disclosure, wherein at least two lyophilised microspheres are provided.

[Implementation W] A method according to any one of Implementations [A]-[V] above, or according to other Implementations of the disclosure, wherein the at least one lyophilised microsphere comprises one or more reagent.

[Implementation X] A method according to Implementation [W] above, or according to other Implementations of the disclosure, wherein the one or more reagent comprises at least a first reagent and a second reagent.

[Implementation Y] A method according to Implementation [X] above, or according to other Implementations of the disclosure, wherein the first reagent and the second reagent are different.

[Implementation Z] A method according to any one of Implementations [W]-[Y] above, or according to other Implementations of the disclosure, wherein the at least one reagent is selected from one or more enzyme, salt, surfactant, buffering agent, enzyme inhibitor, primer, nucleotide, organic osmolite, magnetic bead, molecular probe, crowding agent, small molecule, labelled-nucleotide, a fluorophore, or any combination thereof.

[Implementation AA] A method according to any one of Implementations [W]-[Z] above, or according to other Implementations of the disclosure, wherein the at least one reagent is a polymerase.

[Implementation AB] A method comprising: providing one or more lyophilised microspheres in a mixing vessel at a first temperature; and generating a fluidized bed of the one or more lyophilised microspheres in the mixing vessel, wherein the fluidized bed has an environmental humidity of between about 10% and about 20%, under conditions effective to encapsulate the one or more lyophilised microspheres with a coating formulation.

[Implementation AC] A method according to Implementation [AB] above, or according to other Implementations of the disclosure, wherein the fluidized bed has a fluidization rate of between about 1 cubic meters per hour ($m^3$/h) and about 30 $m^3$/h.

[Implementation AD] A method according to Implementation [AB] or [AC], or according to other Implementations of the disclosure, wherein the coating formulation comprises a water content of between about 0.1 wt. % and about 5 wt. %.

[Implementation AE] A method according to any one of Implementations [AB]-[AD] above, or according to other Implementations of the disclosure, wherein the encapsulated lyophilised microspheres comprise a water content of below about 5 wt. %.

[Implementation AF] A method according to any one of Implementations [AB]-[AE] above, or according to other Implementations of the disclosure, wherein the coating formulation is applied by at least one spray nozzle.

[Implementation AG] A method according to Implementation [AF] above, or according to other Implementations of the disclosure, wherein the at least one spray nozzle has a diameter of between about 0.1 mm and about 1.5 mm.

[Implementation AH] A method according to any one of Implementations [AB]-[AG] above, or according to other Implementations of the disclosure, wherein the coating formulation is sprayed on the one or more lyophilised microspheres in the fluidized bed.

[Implementation AI] A method according to Implementation [AH] above, or according to other Implementations of the disclosure, wherein the coating formulation is applied at a spray rate of between about 1.5 grams per minute (g/min) and about 10 g/min.

[Implementation AJ] A method according to Implementations [AH] or [AI] above, or according to other Implementations of the disclosure, wherein the coating the coating formulation is applied at an atomizing rate of between about 0.5 bar and about 1.5 bar.

[Implementation AK] A method according to Implementation [AB] above, or according to other Implementations of the disclosure, wherein generating the fluidized bed comprises: elevating the first temperature in the mixing vessel to a second temperature; and supplying air in the mixing vessel under conditions effective to float the one or more lyophilised microspheres in the air.

[Implementation AL] A method according to any one of Implementations [AB]-[AKK] above, or according to other Implementations of the disclosure, wherein the mixing vessel comprises a single open vessel.

[Implementation AM] A method according to any one of Implementations [AB]-[AL] above, or according to other Implementations of the disclosure, wherein the mixing vessel comprises one or more cylindrical draft tube which is disposed in the mixing vessel.

[Implementation AN] A method according to any one of Implementations [AB]-[AM] above, or according to other Implementations of the disclosure, wherein the mixing vessel comprises an outer circumference.

[Implementation AO] A method according to Implementation [AN] above, or according to other Implementations of the disclosure, wherein the one or more cylindrical draft tube is between about 25 mm and about 500 mm away from the outer circumference of the mixing vessel.

[Implementation AP] A method according to any one of Implementations [AB]-[AO] above, or according to other Implementations of the disclosure, wherein the air is supplied by an air supply unit.

[Implementation AQ] A method according to any one of Implementations [AB]-[AP] above, or according to other Implementations of the disclosure, wherein the fluidized bed is in a Wurster configuration, a top spray configuration, or a combination thereof.

[Implementation AR] A method according to Implementation [AQ] above, or to other Implementations to around the corner, wherein the fluidized bed is in a Wurster configuration.

[Implementation AS] A method according to Implementation [AQ] above, or to other Implementations to around the corner, wherein the fluidized bed is in a top configuration.

[Implementation AT] A method according to any one of Implementations [AB]-[AS] above, or according to other Implementations of the disclosure, wherein the first temperature comprises a temperature at or below about 30° C.

[Implementation AU] A method according to any one of Implementations [AK]-[AT] above, or according to other Implementations of the disclosure, wherein the second temperature comprises a temperature above about 40° C.

[Implementation AV] A method according to any one of Implementations [AB]-[AU] above, or according to other Implementations of the disclosure, wherein the mixing vessel has a diameter of between about 25 mm and about 500 mm.

[Implementation AW] A method according to any one of Implementations [AB]-[AV] above, or according to other Implementations of the disclosure, wherein at least two lyophilised microspheres are provided.

[Implementation AX] A method according to any one of Implementations [AB]-[AW] above, or according to other Implementations of the disclosure, wherein the at least one lyophilised microsphere comprises one or more reagent.

[Implementation AY] A method according to Implementation [AX] above, or to other Implementations to around the corner, wherein the one or more reagent comprises at least a first reagent and a second reagent.

[Implementation AZ] A method according to Implementation [AY] above, or to other Implementations to around the corner, wherein the first reagent and the second reagent are different.

[Implementation BA] A method according to Implementation [AX] or [AZ] above, or to other Implementations to around the corner, wherein the at least one reagent is selected from one or more enzyme, salt, surfactant, buffering agent, enzyme inhibitor, primer, nucleotide, organic osmolite, magnetic bead, molecular probe, crowding agent, small molecule, labelled-nucleotide, a fluorophore, or any combination thereof.

[Implementation BB] A method according to any one of Implementations [AB]-[BA] above, or according to other Implementations of the disclosure, wherein the at least one reagent is a polymerase.

[Implementation BC] A method comprising: providing one or more lyophilised microspheres in a mixing vessel at a first temperature; and generating a fluidized bed of the one or more lyophilised microspheres in the mixing vessel, wherein the coating formulation is applied at a spray rate of between about 1.5 grams per minute (g/min) and about 10 g/min, under conditions effective to encapsulate the one or more lyophilised microspheres with a coating formulation.

[Implementation BD] A method according to Implementation [BC] above, or according to other Implementations of the disclosure, wherein the fluidized bed has a fluidization rate of between about 1 cubic meters per hour ($m^3$/h) and about 30 $m^3$/h.

[Implementation BE] A method according to Implementation [BC] or [BD] above, or to other Implementations of the disclosure, wherein the fluidized bed has an environmental humidity of between about 10% and about 20%.

[Implementation BF] A method according to any one of Implementations [BC]-[BE] above, or according to other Implementations of the disclosure, wherein the coating formulation comprises a water content of between about 0.1 wt. % and about 5 wt. %.

[Implementation BG] A method according to any one of Implementations [BC]-[BF] above, or according to other Implementations of the disclosure, wherein the encapsulated lyophilised microspheres comprise a water content of below about 5 wt. %.

[Implementation BH] A method according to any one of Implementations [BC]-[BG] above, or according to other Implementations of the disclosure, wherein the coating formulation is applied by at least one spray nozzle.

[Implementation BI] A method according to Implementation [BH] above, or according to other Implementations of the disclosure, wherein the at least one spray nozzle has a diameter of between about 0.1 mm and about 1.5 mm.

[Implementation BJ] A method according to any one of Implementations [BC]-[BI] above, or according to other Implementations of the disclosure, wherein the coating formulation is sprayed on the one or more lyophilised microspheres in the fluidized bed.

[Implementation BK] A method according to any one of Implementations [BC]-[BJ] above, or according to other Implementations of the disclosure, wherein the coating formulation is applied at an atomizing rate of between about 0.5 bar and about 1.5 bar.

[Implementation BL] A method according to any one of Implementations [BC]-[BK] above, or according to other Implementations of the disclosure, wherein generating the fluidized bed comprises: elevating the first temperature in the mixing vessel to a second temperature; and supplying air in the mixing vessel under conditions effective to float the one or more lyophilised microspheres in the air.

[Implementation BM] A method according to any one of Implementations [BC]-[BL] above, or according to other Implementations of the disclosure, wherein the mixing vessel comprises a single open vessel.

[Implementation BN] A method according to any one of Implementations [BC]-[BM] above, or according to other Implementations of the disclosure, wherein the mixing vessel comprises one or more cylindrical draft tube which is disposed in the mixing vessel.

[Implementation BO] A method according to any one of Implementations [BC]-[BN] above, or according to other Implementations of the disclosure, wherein the mixing vessel comprises an outer circumference.

[Implementation BP] A method according to Implementation [BO] above, or according to other Implementations of the disclosure, wherein the one or more cylindrical draft tube is between about 25 mm and about 500 mm away from the outer circumference of the mixing vessel.

[Implementation BQ] A method according to any one of Implementations [BC]-[BP] above, or according to other Implementations of the disclosure, wherein the air is supplied by an air supply unit.

[Implementation BR] A method according to any one of Implementations [BC]-[BQ] above, or according to other Implementations of the disclosure, wherein the fluidized bed is in a Wurster configuration, a top spray configuration, or a combination thereof.

[Implementation BS] A method according to Implementation [BR] above, or according to other Implementations of the disclosure, wherein the fluidized bed is in a Wurster configuration.

[Implementation BT] A method according to Implementation [BR] above, or according to other Implementations of the disclosure, wherein the fluidized bed is in a top configuration.

[Implementation BU] A method according to any one of Implementations [BC]-[BT] above, or according to other Implementations of the disclosure, wherein the first temperature comprises a temperature at or below about 30° C.

[Implementation BV] A method according to any one of Implementations [BL]-[BU] above, or according to other Implementations of the disclosure, wherein the second temperature comprises a temperature above about 40° C.

[Implementation BW] A method according to any one of Implementations [BC]-[BV] above, or according to other Implementations of the disclosure, wherein the mixing vessel has a diameter of between about 25 mm and about 500 mm.

[Implementation BX] A method according to any one of Implementations [BC]-[BW] above, or according to other Implementations of the disclosure, wherein at least two lyophilised microspheres are provided.

[Implementation BY] A method according to any one of Implementations [BC]-[BX] above, or according to other Implementations of the disclosure, wherein the at least one lyophilised microsphere comprises one or more reagent.

[Implementation BZ] A method according to Implementation [BY] above, or according to other Implementations of the disclosure, wherein the one or more reagent comprises at least a first reagent and a second reagent.

[Implementation CA] A method according to Implementation [BZ] above, or according to other Implementations of the disclosure, wherein the first reagent and the second reagent are different.

[Implementation CB] A method according to any one of Implementations [BY]-[CA] above, or according to other Implementations of the disclosure, wherein the at least one reagent is selected from one or more enzyme, salt, surfactant, buffering agent, enzyme inhibitor, primer, nucleotide, organic osmolite, magnetic bead, molecular probe, crowding agent, small molecule, labelled-nucleotide, a fluorophore, or any combination thereof.

[Implementation CC] A method according to any one of Implementations [BY]-[CB] above, or according to other Implementations of the disclosure, wherein the at least one reagent is a polymerase.

[Implementation CD] A method comprising: providing one or more lyophilised microspheres in a mixing vessel at a first temperature; and generating a fluidized bed of the one or more lyophilised microspheres in the mixing vessel, wherein the coating formulation is applied at an atomizing rate of between about 0.5 bar and about 1.5 bar, under conditions effective to encapsulate the one or more lyophilised microspheres with a coating formulation.

[Implementation CE] A method according to Implementation [CD] above, or according to other Implementations of the disclosure, wherein the fluidized bed has a fluidization rate of between about 1 cubic meters per hour ($m^3/h$) and about 30 $m^3/h$.

[Implementation CF] A method according to Implementation [CD] or [CE] above, or according to other Implementations of the disclosure, wherein the fluidized bed has an environmental humidity of between about 10% and about 20%.

[Implementation CG] A method according to any one of Implementations [CD]-[CF] above, or according to other Implementations of the disclosure, wherein the coating formulation comprises a water content of between about 0.1 wt. % and about 5 wt. %.

[Implementation CH] A method according to any one of Implementations [CD]-[CG] above, or according to other Implementations of the disclosure, wherein the encapsulated lyophilised microspheres comprise a water content of below about 5 wt. %.

[Implementation CI] A method according to any one of Implementations [CD]-[CH] above, or according to other Implementations of the disclosure, wherein the coating formulation is applied by at least one spray nozzle.

[Implementation CJ] A method according to Implementation [CI] above, or according to other Implementations of the disclosure, wherein the at least one spray nozzle has a diameter of between about 0.1 mm and about 1.5 mm.

[Implementation CK] A method according to any one of Implementations [CD]-[CJ] above, or according to other Implementations of the disclosure, wherein the coating formulation is sprayed on the one or more lyophilised microspheres in the fluidized bed.

[Implementation CL] A method according to Implementation [CJ] above, or according to other Implementations of the disclosure, wherein the coating formulation is applied at a spray rate of between about 1.5 grams per minute (g/min) and about 10 g/min.

[Implementation CM] A method according to Implementation [CK] or [CL] above, or according to other Implementations of the disclosure, wherein the coating formulation is applied at an atomizing rate of between about 0.5 bar and about 1.5 bar.

[Implementation CN] A method according to any one of Implementations [CD]-[CM] above, or according to other Implementations of the disclosure, wherein generating the fluidized bed comprises: elevating the first temperature in the mixing vessel to a second temperature; and supplying air in the mixing vessel under conditions effective to float the one or more lyophilised microspheres in the air.

[Implementation CO] A method according to any one of Implementations [CD]-[CN] above, or according to other Implementations of the disclosure, wherein the mixing vessel comprises a single open vessel.

[Implementation CP] A method according to any one of Implementations [CD]-[CO] above, or according to other Implementations of the disclosure, wherein the mixing vessel comprises one or more cylindrical draft tube which is disposed in the mixing vessel.

[Implementation CQ] A method according to any one of Implementations [CD]-[CP] above, or according to other Implementations of the disclosure, wherein the mixing vessel comprises an outer circumference.

[Implementation CR] A method according to Implementation [CQ] above, or according to other Implementations of the disclosure, wherein the one or more cylindrical draft tube is between about 25 mm and about 500 mm away from the outer circumference of the mixing vessel.

[Implementation CS] A method according to any one of Implementations [CD]-[CR] above, or according to other Implementations of the disclosure, wherein the air is supplied by an air supply unit.

[Implementation CT] A method according to any one of Implementations [CD]-[CS] above, or according to other Implementations of the disclosure, wherein the fluidized bed is in a Wurster configuration, a top spray configuration, or a combination thereof.

[Implementation CU] A method according to Implementation [CT] above, or according to other Implementations of the disclosure, wherein the fluidized bed is in a Wurster configuration.

[Implementation CV] A method according to Implementation [CT] above, or according to other Implementations of the disclosure, wherein the fluidized bed is in a top configuration.

[Implementation CW] A method according to any one of Implementations [CD]-[CV] above, or according to other Implementations of the disclosure, wherein the first temperature comprises a temperature at or below about 30° C.

[Implementation CX] A method according to Implementation [CN] or [CW] above, or according to other Implementations of the disclosure, wherein the second temperature comprises a temperature above about 40° C.

[Implementation CY] A method according to any one of Implementations [CD]-[CX] above, or according to other Implementations of the disclosure, wherein the mixing vessel has a diameter of between about 25 mm and about 500 mm.

[Implementation CZ] A method according to any one of Implementations [CD]-[CY] above, or according to other Implementations of the disclosure, wherein at least two lyophilised microspheres are provided.

[Implementation DA] A method according to any one of Implementations [CD]-[CZ] above, or according to other Implementations of the disclosure, wherein the at least one lyophilised microsphere comprises one or more reagent.

[Implementation DB] A method according to Implementation [DA] above, or according to other Implementations of the disclosure, wherein the one or more reagent comprises at least a first reagent and a second reagent.

[Implementation DC] A method according to Implementation [DB] above, or according to other implementations of this disclosure, wherein the first reagent and the second reagent are different.

[Implementation DD] A method according to any one of Implementations [DA]-[DC] above, or according to other Implementations of the disclosure, wherein the at least one reagent is selected from one or more enzyme, salt, surfactant, buffering agent, enzyme inhibitor, primer, nucleotide, organic osmolite, magnetic bead, molecular probe, crowding agent, small molecule, labelled-nucleotide, a fluorophore, or any combination thereof.

[Implementation DE] A method according to any one of Implementations [DA]-[DD] above, or according to other Implementations of the disclosure, wherein the at least one reagent is a polymerase.

[Implementation DF] A method comprising: providing one or more lyophilised microspheres in a mixing vessel at a first temperature; and generating a fluidized bed of the one or more lyophilised microspheres in the mixing vessel, wherein the fluidized bed is in a Wurster configuration, a top spray configuration, or a combination thereof, under conditions effective to encapsulate the one or more lyophilised microspheres with a coating formulation.

[Implementation DG] A method according to Implementation [DF] above, or according to other Implementations of the disclosure, wherein the fluidized bed has a fluidization rate of between about 1 cubic meters per hour ($m^3/h$) and about 30 $m^3/h$.

[Implementation DH] A method according to Implementation [DF] or [DG] above, or according to other Implementations of the disclosure, wherein the fluidized bed has an environmental humidity of between about 10% and about 20%.

[Implementation DI] A method according to any one of Implementations [DF]-[DH] above, or according to other Implementations of the disclosure, wherein the coating formulation comprises a water content of between about 0.1 wt. % and about 5 wt. %.

[Implementation DJ] A method according to any one of Implementations [DF]-[DI] above, or according to other Implementations of the disclosure, wherein the encapsulated lyophilised microspheres comprise a water content of below about 5 wt. %.

[Implementation DK] A method according to any one of Implementations [DF]-[DJ] above, or according to other Implementations of the disclosure, wherein the coating formulation is applied by at least one spray nozzle.

[Implementation DL] A method according to Implementation [DK] above, or according to other Implementations of the disclosure, wherein the at least one spray nozzle has a diameter of between about 0.1 mm and about 1.5 mm.

[Implementation DM] A method according to Implementation [DK] or [DL] above, or according to other Implementations of the disclosure, wherein the coating formulation is sprayed on the one or more lyophilised microspheres in the fluidized bed.

[Implementation DN] A method according to Implementation [DL] or [DM] above, or according to other Implementations of the disclosure, wherein the coating formulation is applied at a spray rate of between about 1.5 grams per minute (g/min) and about 10 g/min.

[Implementation DO] A method according to any one of Implementations [DF]-[DN] above, or according to other Implementations of the disclosure, wherein the coating formulation is applied at an atomizing rate of between about 0.5 bar and about 1.5 bar.

[Implementation DP] A method according to any one of Implementations [DF]-[DO] above, or according to other Implementations of the disclosure, wherein generating the fluidized bed comprises: elevating the first temperature in the mixing vessel to a second temperature; and supplying air in the mixing vessel under conditions effective to float the one or more lyophilised microspheres in the air.

[Implementation DQ] A method according to any one of Implementations [DF]-[DP] above, or according to other Implementations of the disclosure, wherein the mixing vessel comprises a single open vessel.

[Implementation DR] A method according to any one of Implementations [DF]-[DQ] above, or according to other Implementations of the disclosure, wherein the mixing vessel comprises one or more cylindrical draft tube which is disposed in the mixing vessel.

[Implementation DS] A method according to any one of Implementations [DF]-[DR] above, or according to other Implementations of the disclosure, wherein the mixing vessel comprises an outer circumference.

[Implementation DT] A method according to Implementation [DS] above, or according to other Implementations of the disclosure, wherein the one or more cylindrical draft tube is between about 25 mm and about 500 mm away from the outer circumference of the mixing vessel.

[Implementation DU] A method according to any one of Implementations [DF]-[DT] above, or according to other Implementations of the disclosure, wherein the air is supplied by an air supply unit.

[Implementation DV] A method according to any one of Implementations [DF]-[DU] above, or according to other Implementations of the disclosure, wherein the coating formulation is applied at an atomizing rate of between about 0.5 bar and about 1.5 bar.

[Implementation DW] A method according to Implementation [DV] above, or according to other Implementations of the disclosure, wherein the one or more cylindrical draft, wherein the fluidized bed is in a Wurster configuration.

[Implementation DX] A method according to Implementation [DW] above, or according to other Implementations of the disclosure, wherein the fluidized bed is in a top configuration.

[Implementation DY] A method according to any one of Implementations [DF]-[DX] above, or according to other Implementations of the disclosure, wherein the first temperature comprises a temperature at or below about 30° C.

[Implementation DZ] A method according to any one of Implementations [DP]-[DY] above, or according to other Implementations of the disclosure, wherein the second temperature comprises a temperature above about 40° C.

[Implementation EA] A method according to any one of Implementations [DF]-[DZ] above, or according to other Implementations of the disclosure, wherein the mixing vessel has a diameter of between about 25 mm and about 500 mm.

[Implementation EB] A method according to any one of Implementations [DF]-[EA] above, or according to other Implementations of the disclosure, wherein at least two lyophilised microspheres are provided.

[Implementation EC] A method according to any one of Implementations [DF]-[EB] above, or according to other Implementations of the disclosure, wherein the at least one lyophilised microsphere comprises one or more reagent.

[Implementation ED] A method according to Implementation [EC] above, or according to other Implementations of the disclosure, wherein the one or more reagent comprises at least a first reagent and a second reagent.

[Implementation EE] A method according to Implementation [EC] or [ED] above, or according to other Implementations of the disclosure, wherein the first reagent and the second reagent are different.

[Implementation EF] A method according to any one of Implementations [ED]-[EE] above, or according to other Implementations of the disclosure, wherein the at least one reagent is selected from one or more enzyme, salt, surfactant, buffering agent, enzyme inhibitor, primer, nucleotide, organic osmolite, magnetic bead, molecular probe, crowding agent, small molecule, labelled-nucleotide, a fluorophore, or any combination thereof.

[Implementation EG] A method according to any one of Implementations [EC]-[EF] above, or according to other Implementations of the disclosure, wherein the at least one reagent is a polymerase.

[Implementation EH] A according to any one of Implementations [A]-[EG] above, or according to other Implementations of the disclosure, wherein one or more of: the fluidized bed has a fluidization rate of between about 1 cubic meters per hour ($m^3/h$) and about 30 $m^3/h$; the fluidized bed has an environmental humidity of between about 10% and about 20%, the coating formulation is applied at a spray rate of between about 1.5 grams per minute (g/min) and about 10 g/min; the coating formulation is applied at an atomizing rate of between about 0.5 bar and about 1.5 bar; the fluidized bed is in a Wurster configuration, a top spray configuration, or a combination thereof; and any combination of two or more of the foregoing.

[Implementation EI] A system comprising: one or more lyophilised microspheres; a mixing vessel configured for holding the one or more lyophilised microspheres; a mixer for generating a fluidized bed of the one or more lyophilised microspheres in the mixing vessel at a location; and at least one spray nozzle configured to introduce a shell formulation into the mixing vessel at the location.

What is claimed is:

1. A method comprising:

providing one or more lyophilised microspheres in a mixing vessel at a first temperature, where the lyophilised microspheres comprise a nucleic acid sequencing reagent;

generating a fluidized bed of the one or more lyophilised microspheres in the mixing vessel, wherein the fluidized bed has a fluidization rate of between about 1 L/h and about 30 L/h; and encapsulating the one or more lyophilised microspheres with a coating formulation.

2. The method of claim 1, wherein the fluidized bed has an environmental humidity of between about 10% and about 20%.

3. The method of claim 1, wherein the coating formulation is applied by at least one spray nozzle and the at least one spray nozzle has a diameter of between about 0.1 mm and about 1.5 mm.

4. The method of claim 3, wherein the coating formulation is applied to the one or more lyophilized microspheres in the fluidized bed at one or more of:

(i) a spray rate of between about 1.5 grams per minute (g/min) and about 10 g/min; and (ii) an atomizing rate of between about 0.5 bar and about 1.5 bar.

5. The method of claim 1, wherein generating the fluidized bed comprises:

elevating the first temperature in the mixing vessel to a second temperature; and supplying air in the mixing vessel under conditions effective to float the one or more lyophilised microspheres in the air.

6. The method of claim 1, wherein the mixing vessel comprises:

one or more cylindrical draft tube which is disposed in the mixing vessel; and an outer circumference;

wherein the one or more cylindrical draft tube is between about 25 mm and about 500 mm away from the outer circumference of the mixing vessel.

7. The method of claim 1, wherein the fluidized bed is in a Wurster configuration, a top spray configuration, or a combination thereof.

8. The method of claim 1, wherein the first temperature comprises a temperature at or below about 30° C.

9. The method of claim 5, wherein the second temperature comprises a temperature above about 40°° C.

10. The method of claim 1, wherein the nucleic acid sequencing reagent comprises at least a first reagent and a second reagent.

11. The method of claim 1, wherein the nucleic acid sequencing reagent is selected from one or more enzyme, salt, surfactant, buffering agent, enzyme inhibitor, primer, nucleotide, organic osmolyte osmolite, magnetic bead, molecular probe, crowding agent, small molecule, labelled-nucleotide, or fluorophore, or any combination thereof.

12. The method of claim 1, wherein the nucleic acid sequencing reagent is a polymerase.

* * * * *